US012577712B2

(12) United States Patent
Fukuda

(10) Patent No.: US 12,577,712 B2
(45) Date of Patent: Mar. 17, 2026

(54) COLORED NON-WOVEN FABRIC

(71) Applicant: KAO CORPORATION, Tokyo (JP)

(72) Inventor: Teruyuki Fukuda, Wakayama (JP)

(73) Assignee: KAO CORPORATION, Tokyo (JP)

( * ) Notice: Subject to any disclaimer, the term of this patent is extended or adjusted under 35 U.S.C. 154(b) by 608 days.

(21) Appl. No.: 17/787,894

(22) PCT Filed: Dec. 22, 2020

(86) PCT No.: PCT/JP2020/048006

§ 371 (c)(1),
(2) Date: Jun. 21, 2022

(87) PCT Pub. No.: WO2021/132264

PCT Pub. Date: Jul. 1, 2021

(65) Prior Publication Data

US 2023/0043070 A1 Feb. 9, 2023

(30) Foreign Application Priority Data

Dec. 23, 2019 (JP) ................................ 2019-232101

(51) Int. Cl.

*D04H 1/4382* (2012.01)
*A61K 8/02* (2006.01)
*D04H 1/728* (2012.01)

(52) U.S. Cl.

CPC ......... *D04H 1/4382* (2013.01); *A61K 8/0208* (2013.01); *D04H 1/728* (2013.01)

(58) Field of Classification Search

CPC ...... D04H 1/4382; D04H 1/728; A45D 44/22; A61K 8/0208; A61K 8/29; A61K 8/8158; A61K 8/892; A61Q 1/00; A61Q 1/02; A61Q 19/08; A61Q 9/70; A61F 13/51496; A61F 13/51478; A61F 2013/51452

USPC ................................................ 424/401, 442

See application file for complete search history.

(56) References Cited

U.S. PATENT DOCUMENTS

| | | | |
|---|---|---|---|
| 2009/0151849 | A1 | 6/2009 | MacDonald et al. |
| 2013/0142852 | A1 | 6/2013 | Tojo et al. |

FOREIGN PATENT DOCUMENTS

| | | | |
|---|---|---|---|
| CN | 102958505 | * | 3/2013 |
| JP | 61-111993 | U | 7/1986 |
| JP | 63-50586 | A | 3/1988 |
| JP | 6-189942 | A | 7/1994 |
| JP | 11-169390 | A | 6/1999 |
| JP | 2000-102522 | A | 4/2000 |
| JP | 2001-278739 | A | 10/2001 |

(Continued)

OTHER PUBLICATIONS

Extended European Search Report issued on Nov. 30, 2023 in European Patent Application No. 20908174.4, 7 pages.

(Continued)

*Primary Examiner* — Camie S Thompson

(74) *Attorney, Agent, or Firm* — Oblon, McClelland, Maier & Neustadt, L.L.P.

(57) ABSTRACT

A colored nonwoven fabric that contains a colorant and nanofibers, in which the colored nonwoven fabric has an uneven shape on at least part of a surface thereof, and an $L^*_1$ value of convex portions of the uneven shape is higher than an $L^*_2$ value of concave portions of the uneven shape; a colored nonwoven fabric set; and a process for producing the colored nonwoven fabric.

18 Claims, 6 Drawing Sheets

(56) References Cited

FOREIGN PATENT DOCUMENTS

| | | | | |
|---|---|---|---|---|
| JP | 2002-371478 | A | | 12/2002 |
| JP | 2005-34424 | A | | 2/2005 |
| JP | 2006-230703 | A | | 9/2006 |
| JP | 2006-328562 | A | | 12/2006 |
| JP | 101182650 | A | | 5/2008 |
| JP | 2010248645 | | * | 11/2010 |
| JP | 2011-173851 | A | | 9/2011 |
| JP | 2012-12337 | A | | 1/2012 |
| JP | 2012-12339 | A | | 1/2012 |
| JP | 102691176 | A | | 9/2012 |
| JP | 2013-136550 | A | | 7/2013 |
| JP | 2016-190825 | A | | 11/2016 |
| JP | 2019-44294 | A | | 3/2019 |
| KR | 10-1415885 | B1 | | 7/2014 |

OTHER PUBLICATIONS

International Search Report issued on Mar. 16, 2021 in PCT/JP2020/048006 filed on Dec. 22, 2020, 2 pages.

Zhuang Guokang, "Integrative Chinese and Western Medicine Clinical Practice in Dermatology," Ocean Press, Aug. 2011, 16 pages (with English machine translation).

* cited by examiner

COLORED NON-WOVEN FABRIC

CROSS-REFERENCE TO RELATED APPLICATIONS

The present application is a 35 U.S.C. § 371 national stage application of International patent application PCT/JP2020/048006, filed Dec. 22, 2020, which is based on and claims the benefit of priority to Japanese Application No. 2019-232101, filed Dec. 23, 2019. The entire contents of these applications are incorporated herein by reference.

FIELD OF THE INVENTION

The present invention relates to a colored nonwoven fabric, a colored nonwoven fabric set, and a process for producing the colored nonwoven fabric.

BACKGROUND OF THE INVENTION

In recent years, as a means for simply performing makeup or tattooing on a body surface (skin), a foundation tape or a tattoo seal has now been commercially available.

The foundation tape has been used in the applications for hiding various scars, such as gash, burn scars, bruises, operation scars, etc., which can be hardly concealed merely by a concealer or a foundation.

On the other hand, the tattoo seal aims at temporally applying decorations, such as patterns, characters, tattoos, etc., to the skin. In this case, the skin can be returned to its original appearance by removing the tattoo seal from the skin, and therefore the tattoo seal has been often used to easily enjoy face painting or body painting upon sports invents, etc.

For example, JP 2016-190825A (Patent Literature 1) discloses a skin seal that is attached to a human skin for hiding tattoos, scars, bruises or spots (blemishes), and includes a base material, a separator, a matte layer disposed on the base material, a release agent layer disposed on the matte layer, an adhesive layer disposed on the separator, a resilient layer disposed between the release agent layer and the adhesive layer and an ink layer disposed between the release agent layer and the adhesive layer.

In addition, JP 2012-12339A (Patent Literature 2) aims at providing a sheet-like cosmetic material for makeup which has a high sense of unity with a skin in appearance when attached thereto and a high effect of diminishing fine unevenness of a skin surface, such as fine wrinkles and pores, etc., and further exhibits a high effect of concealing skin color unevenness, such as spots, etc., and discloses a sheet-like cosmetic material for makeup which includes a nanofiber sheet formed of a polymer compound containing a coloring pigment, and the like.

SUMMARY OF THE INVENTION

The present invention relates to a colored nonwoven fabric that contains a colorant and nanofibers, in which the colored nonwoven fabric has an uneven shape on at least part of a surface thereof, and an $L^*_1$ value of convex portions of the uneven shape is higher than an $L^*_2$ value of concave portions of the uneven shape.

DETAILED DESCRIPTION OF THE INVENTION

Figure 1:
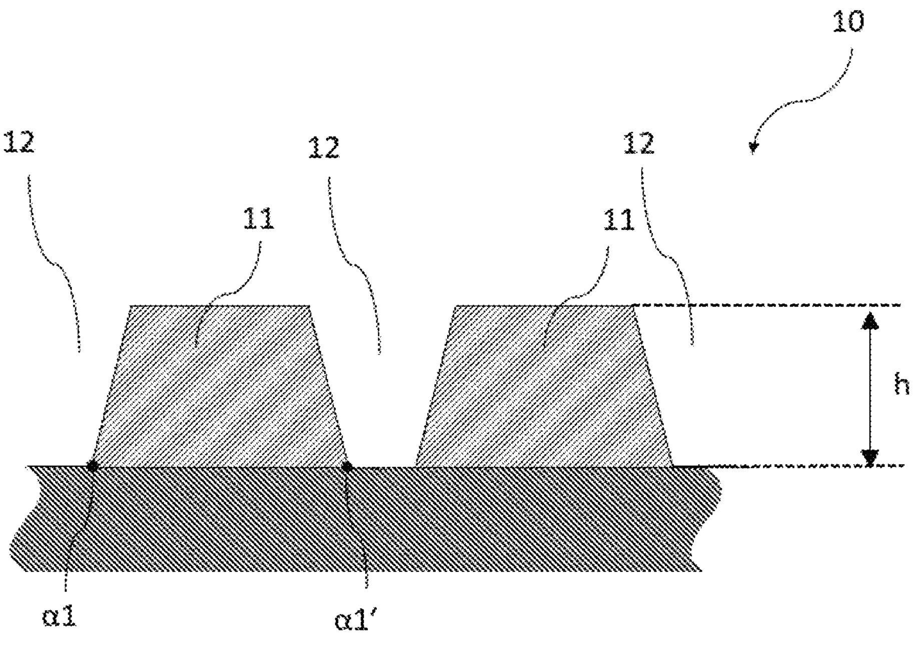
FIG. 1 is a vertical cross-sectional view showing one example of a colored nonwoven fabric.

An appearance of skin is an important factor for humans to give a good impression to another person.

To improve the appearance of skin, when applying makeup, e.g., a base makeup, such as a foundation, a concealer, etc., or a point makeup, such as an eye shadow, a blush, etc., to the skin, various color cosmetics or various kinds of cosmetics have been applied over and over to the skin to adjust width or shading of the cosmetics applied, whereby it has been attempted to create a harmonized texture of the skin though it looks to be uneven at a glance, and thereby produce a good impression against another person.

In addition, makeup may be applied to the skin to correct a degree of gloss or color unevenness, etc., on a whole portion of the skin. However, a human face or body tends to undergo slight change in shade and difference in gloss due to density of blood vessels or capillaries in a subcutaneous tissue, skin spots (deposition of pigment) owing to exposure to ultraviolet irradiation, dullness or the like depending upon regions thereof. Therefore, even in such a case, it has been required to apply makeup so as to impart a natural impression with a good harmony though it looks to be uneven at a glance.

However, such a complicate precise makeup is hardly created by simple and uniform application of makeup cosmetics, and therefore requires a great deal of time and effort.

In addition, the unevenness of a surface of a human skin is classified into 5 stages, i.e., 1st to 5th stages of a concavo-convex shape (relief) according to fineness thereof. Among them, the appearance of the skin largely depends upon the 5th relief as a condition of a texture of the skin and the 2nd relief as a condition of a horny cell structure of the skin.

The 5th relief is constituted of skin grooves (sulcus cutis) and skin hills (crista cutis) which are generally called as a texture of the skin, and it is known that the difference in the skin texture between individuals becomes more remarkable owing to change in age or skin condition. Along with increase of the age, the skin grooves and the skin hills become unclear, and the number of the skin grooves is reduced, so that the shape of the respective skin hills divided by the skin grooves is distorted, which results in a rough texture of the skin. It is known that in particular, in 25 to 35 years old persons called ages of "a turning point of skin", etc., the rate of reduction in number of the skin grooves relative to the age is increased to a highest level among the whole ages. Thus, it is considered that the number of the skin grooves and the shape of the skin hills constituting the 5th relief have a close relation to aging feel in appearance.

In addition, although the 2nd relief is formed of horny cells discharged by metabolic turnover of a skin tissue, the shape of the 2nd relief tends to be distorted by adverse influence of the humidity or the time required for the metabolic turnover, etc. In particular, in the case where end portions of the horny cells accumulated on a horny layer (stratum corneum) are dried and suffer from roughness and warpage, scattering of light tends to be caused on the surface of the horny layer, so that the skin tends to lose a transparent feel.

Furthermore, it is known that when collagen fibers forming a dermis are reduced with aging, the skin loses elasticity. If the skin loses elasticity, a resilient feel of a whole portion of a face is lost, so that deterioration in skin due to aging, such as sagging, wrinkles, etc., tends to become noticeable. For this reason, it has also been required that the resilient feel of skin is improved for well controlling a skin age.

On the other hand, in the skin seal described in the Patent Literature 1, the skin can be artificially reproduced by printing the ink layer and the resilient layer on a resin film having releasing properties as the base material by ordinary printing methods, such as screen printing, etc., to form predetermined images thereon. The skin seal is used by attaching the ink layer and the resilient layer to portions of the skin on which scars, etc., to be concealed are present, through the adhesive layer. However, the color shade of the human skin varies between individuals, and therefore even in the same person, conditions of the color shade of the skin are different from each other every region or portion of a human face or body according to spots or dullness caused by exposure to ultraviolet irradiation, etc.

In addition, a gloss feel of the skin due to a texture or cuticle of the skin varies depending upon a region or portion of a human face or body even in the same person as well as age, so that a resilient feel of the skin tends to be deteriorated with age.

However, in the case of using the aforementioned skin seal having a simple uniform color, the difference in appearance between the portion to which the skin seal is attached and the other surrounding portions, in particular, a boundary therebetween, tends to become remarkable. As a result, even though scars on the skin are concealed by the skin seal, it will be difficult to hide such a fact that the skin seal is attached to the skin, or suppress deterioration in elasticity of the skin with age and improve a resilient feel of the skin.

In the Patent Literature 2, when the sheet for makeup is attached to a human skin, it is possible to improve a sense of unity of the sheet with the skin in appearance and the effect of concealing the skin color unevenness, such as spots, etc. However, the Patent Literature 2 is concerned merely with the technology of enhancing the effect of making fine skin unevenness less discernible. Therefore, the sheet for makeup described in the Patent Literature 2 still has much room for improvement in providing a natural impression. In addition, as to the sheet for makeup, it has also been required to improve its rub fastness that makes the sheet hardly undergo occurrence of breakage or deformation even when rubbing the skin surface with fingers, etc., by which a gloss feel close to that of a human skin can be maintained.

The present invention relates to a colored nonwoven fabric that is excellent in rub fastness, can exhibit a gloss feel and a transparent feel close to those of a human skin, and further is excellent in a sense of unity with the skin in appearance when attached thereto and can improve a resilient feel of the skin for well controlling a skin age; a colored nonwoven fabric set; and a process for producing the colored nonwoven fabric.

The present inventors have noticed that in order to make a physical shape and optical characteristics of the surface of a colored nonwoven fabric close to a surface configuration of an actual human skin, by forming a configuration of the surface of the colored nonwoven fabric into an uneven shape and making a lightness of convex portions of the uneven shape higher than a lightness of concave portions of the uneven shape, optical characteristics of the resulting colored nonwoven fabric, such as a gloss feel, a transparent feel, etc., owing to the uneven shape of the colored nonwoven fabric and the difference in lightness between the concave portions and the convex portions of the uneven shape of the colored nonwoven fabric become similar to those of a real human skin, and furthermore the colored nonwoven fabric can be improved in rub fastness. As a result, the present inventors have found that with such a knowledge, it is possible to obtain a colored nonwoven fabric that is excellent in rub fastness, can exhibit a gloss feel and a transparent feel close to those of a human skin, and further is excellent in a sense of unity with the skin in appearance when attached thereto and can improve a resilient feel of the skin for well controlling a skin age.

That is, the present invention relates to the following aspects [1] to [3].

[1] A colored nonwoven fabric that contains a colorant and nanofibers,
- in which the colored nonwoven fabric has an uneven shape on at least part of a surface thereof, and an $L^*_1$ value of convex portions of the uneven shape is higher than an $L^*_2$ value of concave portions of the uneven shape.

[2] A colored nonwoven fabric set containing two or more colored nonwoven fabrics respectively according to the above aspect [1], in which:
- the two or more colored nonwoven fabrics have respective uneven shapes that are different in an average height or average maximum cross-sectional area of the convex portions from each other.

[3] A process for producing a colored nonwoven fabric that contains a colorant and nanofibers in which a surface of the colored nonwoven fabric is at least partially formed into an uneven shape, said process including the following steps of:
- an electrospinning step: injecting a polymer compound A by an electrospinning method to deposit the nanofibers on a surface of a collector; and
- an L* value adjusting step: coloring the nanofibers such that an $L^*_1$ value of convex portions of the resulting colored nonwoven fabric is higher than an $L^*_2$ value value of concave portions thereof.

In accordance with the present invention, it is possible to provide a colored nonwoven fabric that is excellent in rub fastness, can exhibit a gloss feel and a transparent feel close to those of a human skin, and further is excellent in a sense of unity with the skin in appearance when attached thereto and can improve a resilient feel of the skin for well controlling a skin age; a colored nonwoven fabric set; and a process for producing the colored nonwoven fabric.

[Colored Nonwoven Fabric and Colored Nonwoven Fabric Set]

The colored nonwoven fabric of the present invention contains a colorant and nanofibers, in which:
- the colored nonwoven fabric has an uneven shape on at least part of a surface thereof and an $L^*_1$ value of convex portions of the uneven shape is higher than an $L^*_2$ value of concave portions of the uneven shape.

The "L* value" as used in the present invention represents a lightness in the CIE 1976 (L*a*b*) color space. In addition, the term "colored" as used in the present invention means the state of exhibiting a color derived from a colorant which is a concept includes a white color and may be either a chromatic color or an achromatic color.

The colored nonwoven fabric of the present invention contains at least a colorant and nanofibers. The nanofibers are formed of the below-mentioned polymer compound A.

The colored nonwoven fabric of the present invention contains the colorant, and is therefore tinted into a color derived from the colorant.

The reason why the aforementioned advantageous effects can be attained by the present invention is considered as follows, though it is not clearly determined yet.

That is, the colored nonwoven fabric of the present invention has the uneven shape on the surface thereof, and therefore can be formed into a surface configuration close to a physical shape of the skin in which the convex portions of the uneven shape are portions corresponding to skin hills, whereas the concave portions of the uneven shape are portions corresponding to skin grooves. In addition, the breakage of the colored nonwoven fabric owing to excessive stress occurring when rubbing the surface of the colored nonwoven fabric tends to be caused from the aforementioned portions corresponding to the skin hills as a starting point. However, since the portions corresponding to the skin hills are surrounded by the portions corresponding to the skin grooves, it is considered that the breakage of the colored nonwoven fabric occurring at the portions corresponding to the skin hills is prevented from propagating to the other portions corresponding to the skin hills, so that the resulting colored nonwoven fabric can be improved in rub fastness.

Also, the colored nonwoven fabric of the present invention has the uneven shape on the surface thereof, and an $L^*_1$ value of the convex portions of the uneven shape is higher than an $L^*_2$ value of the concave portions of the uneven shape. Therefore, it is considered that the colored nonwoven fabric can be well controlled in light scattering intensity. In particular, it is considered that by suitably adjusting sizes and shapes of the concave portions and convex portions as well as the degree of the L* values thereof, it is possible to suppress light scattering on the surface of the colored nonwoven fabric, and thereby obtain the colored nonwoven fabric that can exhibit a gloss feel and a transparent feel close to those of a human skin, and further can be enhanced in a sense of unity with the skin in appearance when attached thereto and can improve a resilient feel of the skin for well conditioning a skin age.

<Uneven Shape>

The uneven shape of the colored nonwoven fabric of the present invention is preferably such an uneven shape as to imitate a surface configuration of the skin, from the viewpoint of improving rub fastness of the resulting colored nonwoven fabric, allowing the colored nonwoven fabric to exhibit a good sense of unity with the skin in appearance, a good gloss feel and a good transparent feel, and further improving a resilient feel of skin and a skin age.

More concretely, the surface configuration of the skin as used herein means visible unevenness of the skin due to wrinkles or pores, microscopic unevenness along respective skin grooves and skin hills, and the like. Among them, from the same viewpoint as described above, as the uneven shape of the colored nonwoven fabric of the present invention, more preferred is an uneven shape imitating unevenness along respective skin grooves and skin hills, and even more preferred is an uneven shape capable of reproducing the aforementioned 5th relief or an uneven shape capable of reproducing the aforementioned 2nd relief.

When attaching the colored nonwoven fabric having the uneven structure capable of reproducing the 5th relief, to the skin, it is possible to control a frequency of occurrence of the skin hills and the skin grooves which have an influence on dullness of the skin.

The average height of the convex portions as the uneven shape capable of reproducing the 5th relief is preferably not less than 10 μm, more preferably not less than 15 μm and even more preferably not less than 20 μm, and is also preferably not more than 250 μm, more preferably not more than 200 μm, even more preferably not more than 150 μm, further even more preferably not more than 100 μm and still further even more preferably not more than 50 μm.

The average maximum cross-sectional area of the convex portions as the uneven shape capable of reproducing the 5th relief is preferably not less than 0.005 mms, more preferably not less than 0.007 $mm^2$ and even more preferably not less than 0.01 $mm^2$, and is also preferably not more than 0.25 $mm^2$, more preferably not more than 0.20 $mm^2$, even more preferably not more than 0.15 $mm^2$, further even more preferably not more than 0.10 $mm^2$ and still further even more preferably not more than 0.05 mms.

In this case, as shown in FIG. 1, the "height of the convex portion" of the uneven shape as used in the present invention means a distance h between an uppermost portion of the convex portion and a lowermost portion of the concave portion.

Also, the "maximum cross-sectional area of the convex portion" of the uneven shape means a maximum value of a cross-sectional area of the convex portion obtained by cutting the convex portion along a horizontal plane. More specifically, in FIG. 1, the maximum cross-sectional area of the convex portion is a cross-sectional area obtained by cutting the convex portion by the line ($\alpha 1$-$\alpha 1'$) connecting a point $\alpha 1$ and a point $\alpha 1'$.

The average height and the average maximum cross-sectional area of the convex portions of the colored nonwoven fabric may be measured by the methods described in Examples below. These items are also hereinafter defined in the same way.

When the colored nonwoven fabric having the uneven shape capable of reproducing the 2nd relief is attached to the skin, it is possible to reproduce a frequency of occurrence of the horny cell structure which has an influence on a transparent feel of the skin.

The average height of the convex portions as the uneven shape capable of reproducing the 2nd relief is preferably not less than 0.5 μm, more preferably not less than 1 μm, even more preferably not less than 2 μm and further even more preferably not less than 3 μm, and is also preferably not more than 7 μm, more preferably not more than 6 μm and even more preferably not more than 5 μm.

The average maximum cross-sectional area of the convex portions as the uneven shape capable of reproducing the 2nd relief is preferably not less than 40 $\mu m^2$, more preferably not less than 100 $\mu m^2$, even more preferably not less than 500 $\mu m^2$ and further even more preferably not less than 700 $\mu m^2$, and is also preferably not more than 3,600 $\mu m^2$, more preferably not more than 3,000 $m^2$, even more preferably not more than 2,000 $\mu m^2$, further even more preferably not more than 1,700 $\mu m^2$ and still further even more preferably not more than 1,300 $\mu m^2$.

The uneven shape of the colored nonwoven fabric of the present invention may have such a shape in which a secondary uneven shape reproducing the 2nd relief is further formed on a surface of the convex portion of a primary uneven shape reproducing the 5th relief. With such an uneven shape, the shape that imitates a human skin can be imparted to the resulting nonwoven fabric to reproduce a texture and a transparent feel inherent to the human skin thereon with a high accuracy, whereby it is possible to allow the resulting colored nonwoven fabric to exhibit a good sense of unity with the skin in appearance, a good gloss feel and good a transparent feel, and further improve a resilient feel of the skin and a skin age.

The preferred ranges of the average height and the average maximum cross-sectional area of the convex portions in the primary uneven shape are the same as the preferred ranges of the average height and the average maximum cross-sectional area of the convex portions in the uneven shape capable of reproducing the aforementioned 5th relief.

The preferred ranges of the average height and the average maximum cross-sectional area of the convex portions in the secondary uneven shape are the same as the preferred ranges of the average height and the average maximum cross-sectional area of the convex portions in the uneven shape capable of reproducing the aforementioned 2nd relief.

In the case where the uneven shape of the colored nonwoven fabric of the present invention includes the aforementioned uneven shape capable of reproducing the 5th relief or the aforementioned uneven shape capable of reproducing the 2nd relief, as the plan view shape of the respective convex portions as viewed from the Z-axis direction that is the direction of a thickness of the colored nonwoven fabric, there may be mentioned a circular shape, a semicircular shape, an elliptical shape, and a generally circular shape similar thereto, as well as a polygonal shape, such as a triangular shape, a quadrangular shape, a pentagonal shape, a hexagonal shape, etc., and a generally polygonal shape similar thereto, and the like. Among these shapes, from the viewpoint of improving rub fastness of the resulting colored nonwoven fabric, allowing the colored nonwoven fabric to exhibit a good sense of unity with the skin in appearance, a good gloss feel and a good transparent feel, and further improving a resilient feel of the skin and a skin age, preferred are a polygonal shape, such as an equilateral triangular shape, an isosceles right triangular shape, and a generally triangular shape similar thereto; a square shape, a rectangular shape, a rhombic shape, a parallelogram shape, a trapezoidal shape, and a generally quadrangular shape similar thereto; a pentagonal shape, a hexagonal shape, etc., as well as a generally polygonal shape similar thereto.

These kinds of plan view shapes of the respective convex portions may be used alone or in combination of any two or more thereof.

The plan view shape of the respective convex portions in the primary uneven shape is preferably at least one shape selected from the group consisting of an equilateral triangular shape, an isosceles right triangular shape, and a generally triangular shape similar thereto; a square shape, a rectangular shape, a rhombic shape, a parallelogram shape, a trapezoidal shape, and a generally quadrangular shape similar thereto; a regular hexagonal shape, and a generally hexagonal shape similar thereto, more preferably at least one shape selected from the group consisting of a generally triangular shape, a generally rhombic shape and a generally hexagonal shape, and even more preferably at least one shape selected from the group consisting of an equilateral triangular shape, a rhombic shape and a regular hexagonal shape.

The plan view shape of the respective convex portions in the secondary uneven shape is preferably a quadrangular or higher polygonal shape or a generally polygonal shape similar thereto, and more preferably a hexagonal shape or a generally hexagonal shape similar thereto.

The combination of the plan view shape of the respective convex portions in the primary uneven shape and the plan view shape of the respective convex portions in the secondary uneven shape is preferably a combination of at least one shape selected from the group consisting of a generally triangular shape, a generally rhombic shape and a generally hexagonal shape as the plan view shape of the respective convex portions in the primary uneven shape, and a quadrangular or higher polygonal shape or a generally polygonal shape similar thereto as the plan view shape of the respective convex portions in the secondary uneven shape; more preferably a combination of a generally triangular shape as the plan view shape of the respective convex portions in the primary uneven shape, and a generally hexagonal shape as the plan view shape of the respective convex portions in the secondary uneven shape; and even more preferably a combination of a generally regular triangular shape as the plan view shape of the respective convex portions in the primary uneven shape, and a generally hexagonal shape as the plan view shape of the respective convex portions in the secondary uneven shape.

The average length of the plan view shapes of the convex portions as the uneven shape capable of reproducing the aforementioned 5th relief is preferably not less than 30 μm, more preferably not less than 50 μm and even more preferably not less than 100 μm, and is also preferably not more than 750 μm, more preferably not more than 500 μm, even more preferably not more than 300 μm and further even more preferably not more than 200 μm.

The average length of the plan view shapes of the convex portions as the uneven shape capable of reproducing the aforementioned 2nd relief is preferably not less than 1 μm, more preferably not less than 5 μm, even more preferably not less than 10 μm and further even more preferably not less than 15 μm, and is also preferably not more than 60 μm, more preferably not more than 50 μm, even more preferably not more than 40 μm and further even more preferably not more than 30 μm.

The average length of the plan view shapes of the convex portions as used herein means an average value of diameters thereof in the case where the shape as viewed from the Z-axis direction that is the direction of a thickness of the colored nonwoven fabric is a circular shape, a semicircular shape or a shape similar thereto, an average value of a major axis diameter and a minor axis diameter thereof in the case where the shape as viewed from the Z-axis direction is an elliptical shape or a shape similar thereto, and an average value of lengths of sides of a polygonal shape in the case where the shape as viewed from the Z-axis direction is a generally polygonal shape.

Among them, from the same viewpoint as described above, the uneven shape of the colored nonwoven fabric of the present invention is preferably such a shape in which the plan view shape of the respective convex portions is a generally triangular shape or a generally quadrangular shape, the average height of the convex portions is not less than 10 μm and not more than 250 μm, and the average maximum cross-sectional area of the convex portions is not less than 0.01 $mm^2$ and not more than 0.25 $mm^2$.

In the present invention, from the viewpoint of improving rub fastness of the resulting colored nonwoven fabric, allowing the colored nonwoven fabric to exhibit a good sense of unity with the skin in appearance, a good gloss feel and a good transparent feel, and further improving a resilient feel of the skin and a skin age, the colored nonwoven fabric may be a colored nonwoven fabric including two or more kinds of uneven shapes that are different in average height or average maximum cross-sectional area of the convex portions thereof from each other, and a colored nonwoven fabric set may be a colored nonwoven fabric set containing the two or more kinds of colored nonwoven fabrics of the present invention in which the two or more kinds of colored nonwoven fabrics include respective uneven shapes that are different in average height or average maximum cross-sectional area of the convex portions thereof from each other. The average height and average maximum cross-sectional area of the convex portions of each of the two or more kinds of uneven shapes as well as coloration thereof can be well designed to impart a three-dimensional feel to the face.

For example, as one of methods of enhancing a visual impression by applying makeup, there is known a method utilizing an optical illusion effect. As a method of using the optical illusion effect in makeup, there is used the method in which slightly dark color foundation is put on an outside of a cheek and a jaw to make a face look smaller (shading). This method utilizes such an optical illusion effect that by making an appearance of the face become darker as it approaches toward a side portion of the face as viewed from a front of the face, the curvature of the face in the depth direction (depth feel) is emphasized as compared to an inherent curvature thereof such that a width of the face looks narrower. However, in order to apply such makeup, it is necessary to repeatedly put many layers of makeup cosmetics on the face while controlling gradation thereof. Therefore, the method requires very high-accuracy makeup techniques including control of balance between left and right sides of the face. Although such makeup techniques may be provided by professional application in salons, a great deal of time and effort is required in the case of self-makeup by individuals.

In such circumstances, in the present invention, by designing two or more kinds of uneven shapes as the uneven shape of the colored nonwoven fabric for every parts of the face such that the convex portions of the uneven shapes are different in average height or average maximum cross-sectional area thereof from each other in accordance with every parts of the face, it is possible to impart a three-dimensional feel such as depth feel, facial relief etc., to the face. As the method of attaching a colored nonwoven fabric having different uneven shapes to the skin for every parts of the face, there may be mentioned the method using one sheet of a colored nonwoven fabric having two or more kinds of uneven shapes thereon, or the method using a colored nonwoven fabric set including a plurality of colored nonwoven fabrics that are different in uneven shape from each other.

For example, in the case where the uneven shape formed on the colored nonwoven fabric is varied according to the size of the skin texture, it is possible to make the observer create such an optical illusion that the portion where the size of the skin texture looks large, i.e., the portion where the sizes of the concave and convex portions of the colored nonwoven fabric are large, is close to the observer, whereas the portion where the size of the skin texture looks small, i.e., the portion where the sizes of the concave and convex portions of the colored nonwoven fabric are small, is away from the observer.

In addition, by making the color of the concave portions of the uneven shape darker as approaching toward the side of the face, it is possible to emphasize shading on the face and exhibit the effect of making the face look smaller.

For this reason, when varying a brightness or a three-dimensional feel over a whole portion of the face, it is possible to suitably control a three-dimensional feel of the face and thereby achieve makeup superior to inherent racial characteristics without using invasive procedures, such as cosmetic surgery, etc.

For example, when the colored nonwoven fabric having two or more uneven shapes that are different in an average height or average maximum cross-sectional area of convex portions thereof from each other is used for a forehead portion and a jaw portion or for a nose portion and a side portion of the face, or when the colored nonwoven fabric set including two or more colored nonwoven fabrics having respective uneven shapes that are different in an average height or average maximum cross-sectional area of convex portions thereof from each other is used for a forehead portion and a jaw portion or for a nose portion and a side portion of the face, it is possible to produce a three-dimensional feel over a whole portion of the face.

When the average height and average maximum cross-sectional area of the convex portions of the uneven shape of the colored nonwoven fabric attached to the forehead portion are larger than those of the convex portions of the uneven shape of the colored nonwoven fabric attached to the jaw portion, the forehead portion tends to look close to the observer, whereas the lip portion tends to look remote from the observer, so that a rational impression is imparted to the face. From the aforementioned viewpoint, the preferred ranges of the average height and average maximum cross-sectional area of the convex portions of the respective uneven shapes for the forehead portion and the jaw portion are controlled such that the ratio of the average height of the convex portions of the uneven shape for the forehead portion to the average height of the convex portions of the uneven shape for the jaw portion [average height for forehead portion/average height for jaw portion] is preferably more than 1, more preferably not less than 2 and even more preferably not less than 3, and is also preferably not more than 20, more preferably not more than 15 and even more preferably not more than 10. In addition, from the same viewpoint as described above, the ratio of the average maximum cross-sectional area of the convex portions of the uneven shape for the forehead portion to the average maximum cross-sectional area of the convex portions of the uneven shape for the jaw portion [average maximum cross-sectional area for forehead portion/average maximum cross-sectional area for jaw portion] is preferably more than 1, more preferably not less than 10 and even more preferably not less than 15, and is also preferably not more than 50, more preferably not more than 40 and even more preferably not more than 30.

On the other hand, when the average height and average maximum cross-sectional area of the convex portions of the uneven shape for the forehead portion are smaller than those of the convex portions of the uneven shape for the jaw portion, the forehead portion tends to look remote from the observer, and the lip portion tends to look close to the observer, so that a passionate impression is imparted to the face. From the aforementioned viewpoint, the preferred ranges of the average height and average maximum cross-sectional area of the convex portions of the respective uneven shapes for the forehead portion and the jaw portion are controlled such that the ratio of the average height of the convex portions of the uneven shape for the forehead portion to the average height of the convex portions of the uneven shape for the jaw portion [average height for forehead portion/average height for jaw portion] is preferably less than 1, more preferably not more than 0.5 and even more preferably not more than 0.3. In addition, the ratio of the average maximum cross-sectional area of the convex portions of the uneven shape for the forehead portion to the average maximum cross-sectional area of the convex portions of the uneven shape for the jaw portion [average maximum cross-sectional area for forehead portion/average maximum cross-sectional area for jaw portion] is preferably less than 1, more preferably not more than 0.3 and even more preferably not more than 0.1.

In addition, from the viewpoint of imparting a sense of depth to the face, it is preferred that the average height and average maximum cross-sectional area of the convex portions of the uneven shape for the nose portion are larger than those of the convex portions of the uneven shape for the cheek portion. The preferred ranges of the average height and average maximum cross-sectional area of the convex portions as the respective uneven shapes for the nose portion and the cheek portion are the same as those described above. The ratio of the average height of the convex portions of the uneven shape for the nose portion to the average height of the convex portions of the uneven shape for the cheek portion [average height for nose portion/average height for cheek portion] is preferably more than 1, more preferably not less than 2 and even more preferably not less than 3, and is also preferably not more than 20, more preferably not more than 15 and even more preferably not more than 10, and the ratio of the average maximum cross-sectional area of the convex portions of the uneven shape for the nose portion to the average maximum cross-sectional area of the convex portions of the uneven shape for the cheek portion [average maximum cross-sectional area for nose portion/average maximum cross-sectional area for cheek portion] is preferably more than 1, more preferably not less than 10 and even more preferably not less than 15, and is also preferably not more than 50, more preferably not more than 40 and even more preferably not more than 30.

<L* Value>

In the colored nonwoven fabric of the present invention, from the viewpoint of allowing the colored nonwoven fabric to exhibit a good gloss feel and a good transparent feel as well as from the viewpoint of improving a sense of unity of the colored nonwoven fabric with the skin in appearance, a resilient feel of the skin and a skin age, the $L^*_1$ value of the convex portions of the uneven shape is higher than the $L^*_2$ value of the concave portions of the uneven shape.

From the viewpoint of allowing the colored nonwoven fabric to exhibit a good gloss feel and a good transparent feel as well as from the viewpoint of improving a sense of unity of the colored nonwoven fabric with the skin in appearance, a resilient feel of the skin and a skin age, the difference between the $L^*_1$ value of the convex portions and the $L^*_2$ value of the concave portions is preferably not less than 5, more preferably not less than 10 and even more preferably not less than 15, and is also preferably not more than 60, more preferably not more than 50 and even more preferably not more than 40.

The $L^*_1$ value of the convex portions and the $L^*_2$ value of the concave portions may be measured by the method described in Examples below.

(Nanofibers)

From the viewpoint of allowing the colored nonwoven fabric to remain on skin after being attached to the skin without dissolution thereof, improving rub fastness of the colored nonwoven fabric and allowing the colored nonwoven fabric to exhibit a good gloss feel and a good transparent feel as well as from the viewpoint of improving a sense of unity of the colored nonwoven fabric with the skin in appearance, a resilient feel of the skin and a skin age, the aforementioned nanofibers preferably contain at least a water-insoluble polymer compound, and more preferably are constituted of the water-insoluble polymer compound. In the case where the nanofibers contain the water-insoluble polymer compound, the water-insoluble polymer compound functions as a material for forming a skeleton of the nanofibers. For this reason, even after attaching the colored nonwoven fabric to the skin, at least a part of the nanofibers can be maintained in the form of fibers without being dissolved in water, such as sweat, etc.

The term “water-insoluble polymer compound” as used in the present specification means a polymer compound whose solubility in water is less than 0.2 g as measured under the environmental conditions of 1 atm and 23° C. by weighing 1 g of the polymer compound, dipping the polymer compound in 10 g of ion-exchanged water and then allowing the polymer compound to stand in the dipped state for 24 hours.

The nanofibers contained in the colored nonwoven fabric of the present invention are constituted of a polymer compound A as a raw material thereof. As the polymer compound A, there may be used either a natural polymer or a synthetic polymer.

The polymer compound A may be either water-soluble or water-insoluble. However, from the viewpoint of allowing the colored nonwoven fabric to remain on the skin after being attached to the skin without dissolution thereof, improving rub fastness of the colored nonwoven fabric and allowing the colored nonwoven fabric to exhibit a good gloss feel and a good transparent feel as well as from the viewpoint of improving a sense of unity of the colored nonwoven fabric with the skin in appearance, a resilient feel of the skin and a skin age, the polymer compound A preferably contains the water-insoluble polymer compound, and more preferably contains the water-insoluble polymer compound as a main component thereof.

The “main component” as used herein means a component that has a content of not less than 50% by mass on the basis of the whole amount of the polymer compound A.

Meanwhile, the water-insoluble polymer compound used in the present invention may also include such a water-soluble polymer compound that is rendered water-insoluble by subjecting the nanofibers produced therefrom to water-insolubilizing treatment.

Specific examples of the water-insoluble polymer compound include a hydroxy group-containing polymer compound, such as completely saponified polyvinyl alcohol, partially saponified polyvinyl alcohol, polyvinyl butyral, an alkali-soluble cellulose, etcd a nitrogen-containing functional group-containing polymer resin, e.g., an oxazoline-modified silicone, such as a poly(N-propanoylethyleneimine)-grafted dimethylsiloxane/γ-aminopropylmeth- ylsiloxane copolymer, etc., zein (a main component of a corn protein), etc.; a polyester resin, such as polyethylene terephthalate, polybutylene terephthalate, a polylactic acid (PLA) resin, etc.; an acrylic resin, such as a polyacrylonitrile resin, a polymethacrylic acid resin, etc.; a polystyrene resin; a polyurethane resin; a polyamide resin; a polyimide resin;

a polyamideimide resin; and the like. These water-insoluble polymer compounds may be used alone or in combination of any two or more thereof.

Of these water-insoluble polymer compounds, from the viewpoint of allowing the colored nonwoven fabric to remain on the skin after being attached to the skin without dissolution thereof, improving rub fastness of the colored nonwoven fabric and allowing the colored nonwoven fabric to exhibit a good gloss feel and a good transparent feel as well as from the viewpoint of improving a sense of unity of the colored nonwoven fabric with the skin in appearance, a resilient feel of the skin and a skin age, preferred is at least one compound selected from the group consisting of the aforementioned hydroxy group-containing polymer compound, the aforementioned nitrogen-containing functional group-containing polymer compound and the aforementioned polyester resin, and more preferred are completely saponified polyvinyl alcohol that can be rendered water-insoluble by water-insolubilizing treatment, partially saponified polyvinyl alcohol that can be rendered water-insoluble by water-insolubilizing treatment by crosslinking, an alkali-soluble cellulose, an oxazoline-modified silicone, such as a poly(N-propanoylethyleneimine)-grafted dimethylsiloxane/γ-aminopropylmethylsiloxane copolymer, etc., zein, a water-soluble polyester resin, and the like. Furthermore, from the viewpoint of being rendered water-insoluble by water-insolubilizing treatment, even more preferred is at least one hydroxy group-containing polymer compound selected from the group consisting of completely saponified polyvinyl alcohol, partially saponified polyvinyl alcohol and an alkali-soluble cellulose, and further even more preferred is at least one compound selected from the group consisting of completely saponified polyvinyl alcohol and an alkali-soluble cellulose.

The polyvinyl alcohols, such as completely saponified polyvinyl alcohol, partially saponified polyvinyl alcohol, etc., not only have a water solubility, but also can be rendered water-insoluble by subjecting them to water-insolubilizing treatment, such as crystallization treatment by heating and drying, or crosslinking treatment using a crosslinking agent, etc.

The alkali-soluble cellulose can be rendered water-insoluble by subjecting it to water-insolubilizing treatment by a method of reducing an alkali concentration thereof by dilution or neutralization, etc., a method of raising an ambient environmental temperature, and the like.

The nanofibers constituting the colored nonwoven fabric of the present invention may be formed of the aforementioned water-insoluble polymer compound solely, and may also be formed of both of the water-insoluble polymer compound and the water-soluble polymer compound. When the nanofibers contain the water-soluble polymer compound, the resulting colored nonwoven fabric can exhibit good bonding properties and adhesion properties to the skin. Upon the use of the colored nonwoven fabric according to the present invention, when applying, for example, a liquid material containing water to the surface of the skin, the water-soluble polymer compound in the nanofibers is dissolved in the liquid material by bringing the colored nonwoven fabric into contact with water, and the thus dissolved water-soluble polymer compound exhibits bonding properties and thereby acts as a binder, so that the colored nonwoven fabric can be improved in adhesion properties to the skin. Furthermore, the water-insoluble polymer compound forms a skeleton of the respective nanofibers, and therefore even after the water-soluble polymer compound is dissolved in the liquid material, a part of the nanofibers can maintain their fibrous configuration.

The term "water-soluble polymer compound" as used in the present specification means a polymer compound whose solubility in water is not less than 0.2 g as measured under the environmental conditions of 1 atm and 23° C. by weighing 1 g of the polymer compound, dipping the polymer compound in 10 g of ion-exchanged water and then allowing the polymer compound to stand in the dipped state for 24 hours.

In the case where the nanofibers are formed of the water-insoluble polymer compound and the water-soluble polymer compound, as the water-soluble polymer compound constituting the nanofibers, there may be mentioned, for example, natural polymers, e.g., mucopolysaccharides, such as pullulan, hyaluronic acid, chondroitin sulfate, poly-γ-glutamic acid, modified corn starch, β-glucan, gluco-oligosaccharides, heparin, keratosulfate, etc., cellulose, pectin, xylan, lignin, glucomannan, galacturonic acid, psyllium seed gum, tamarind seed gum, gum arabic, tragacanth gum, soybean water-soluble polysaccharides, alginic acid, carrageenan, laminaran, agar (agarose), fucoidan, methyl cellulose, hydroxypropyl cellulose, hydroxypropylmethyl cellulose, and the like; and synthetic polymers, such as partially saponified polyvinyl alcohol (when not used in combination with the below-mentioned crosslinking agent), low-saponified polyvinyl alcohol, polyvinylpyrrolidone (PVP), polyethylene oxide, sodium polyacrylate, and the like. The polymer compound A may also contain any of these water-soluble polymer compounds in addition to the water-insoluble polymer compound. These water-soluble polymer compounds may be used alone or in combination of any two or more thereof.

Of these water-soluble polymer compounds, from the viewpoint of facilitating production of the nanofibers, at least one compound selected from the group consisting of pullulan, partially saponified polyvinyl alcohol, low-saponified polyvinyl alcohol, polyvinyl pyrrolidone and polyethylene oxide is preferably used.

In the case where the polymer compound A contains the water-soluble polymer compound in addition to the water-insoluble polymer compound, the content of the water-soluble polymer compound on the basis of a total content of the water-insoluble polymer compound and the water-soluble polymer compound is preferably not more than 30% by mass and more preferably not more than 25% by mass, and is also preferably not less than 1% by mass and more preferably not less than 10% by mass. By adjusting the content of the water-soluble polymer compound to the aforementioned range, it is possible not only to attain sufficient bonding properties and adhesion properties of the colored nonwoven fabric when attached to the skin, but also to suppress adhesion between the nanofibers and aggregation of the colorant particles.

(Colorant)

In the present invention, the color of the colored nonwoven fabric is derived from the colorant.

As the aforementioned colorant, from the viewpoint of applying makeup by attaching the colored nonwoven fabric to the skin, there are preferably used colorants that are capable of coloring the nanofibers to a color range in the vicinity of the complementary color for compensating a skin color of the user, for example, a yellow color, a blue to green color, a violet color, a brown color, etc.

In addition, from the viewpoint of enhancing a sense of unity of the colored nonwoven fabric of the present invention with the skin in appearance when attached to the skin, there are preferably used those colorants that are capable of coloring the nanofibers to a color range in the vicinity of additive color mixture for compensating the skin color of the user. In particular, from the viewpoint of effectively concealing the skin color unevenness (for example, such as facial redness, freckles, bags under eyes, spots, etc.) when attaching the colored nonwoven fabric to the skin, and improving a resilient feel of the skin and a skin age, it is preferable to use colorants that are capable of coloring the nanofibers to a color range in the vicinity of an additive color mixture for compensating the skin color of the user.

Examples of white colorants include white pigments, such as titanium oxide, zinc oxide, and the like.

Examples of non-white colorants having a color other than white include inorganic pigments, such as yellow iron oxide, red iron oxide, black iron oxide, carbon blacks, ultramarine blue, Prussian blue, blue titanium oxide, black titanium oxide, chromium oxide, chromium hydroxide, a titanium/titanium oxide sintered product, etc.; organic pigments, such as Red No. 201, Red No. 202, Red No. 226, Yellow No. 401, Blue No. 404, etc.; lake pigments, such as Red No. 104, Red. No. 230, Yellow No. 4, Yellow No. 5, Blue No. 1, etc.; dyes, such as Acid Yellow 1, Acid Orange 7, Food Blue 2, Acid Red 52, etc.; pigments or dyes coated with a resin, such as a polymethacrylic acid ester, etc.; and the like.

As the aforementioned colorant, there may be used not only the colorant particles having an average particle size as small as not more than 1,000 nm, but also a pigment having an average particle size of more than 1,000 nm. Some of white pigments, such as plate-shaped titanium oxide or zinc oxide, pearlescent pigments, lame agents (glitters), etc., may have an average particle size of more than 1,000 nm. These pigments have not only a function as the colorant, but also a function of enhancing diffuse transmission of light, and therefore can also exhibit a function of rendering a boundary between the colored nonwoven fabric attached and its surrounding regions blurred, or a function of suppressing reflection of light on the surface of the colored nonwoven fabric to thereby reduce difference in brightness of light thereon. For this reason, by using these particles in combination with each other, it is possible to reduce the color unevenness of the colored nonwoven fabric on the skin and enhance concealability and a sense of unity of the colored nonwoven fabric with the skin in appearance.

The aforementioned colorant may be subjected to surface treatments from the viewpoint of improving dispersibility thereof. As the surface treatments, there may be mentioned hydrophobization treatments in which ordinary cosmetic particles are treated with various kinds of hydrophobizing agents. Examples of the hydrophobization treatments include silicone treatment, fatty acid treatment, lauroyl lysine treatment, surfactant treatment, metal soap treatment, fluorine compound treatment, lecithin treatment, nylon treatment, and polymer treatment.

In the case where titanium oxide, zinc oxide, etc., for example, are used as the aforementioned colorant, from the viewpoint of improving dispersibility of the colorant as well as from the viewpoint of improving water resistance and sweat resistance of the resulting colored nonwoven fabric, the surface of titanium oxide, zinc oxide, etc., is preferably subjected to the hydrophobization treatments.

[Glitter Pigment]

The colored nonwoven fabric of the present invention preferably contains a glitter pigment (luster pigment) which is called a pearlescent pigment (pearl agent) or a lame agent, as the colorant that acts as a material for improving a three-dimensional feel of a makeup cosmetic coating, from the viewpoint of allowing the colored nonwoven fabric to exhibit a good gloss feel and a good transparent feel as well as from the viewpoint of improving a sense of unity of the colored nonwoven fabric with the skin in appearance, a resilient feel of the skin and a skin age.

In general, a glittering material, such as a pearlescent pigment, a lame agent, etc., is in the form of particles having a flattened shape or a flat-plate shape. In particular, since the glittering material is likely to undergo electrification owing to its constituents, the particles thereof tend to be overlapped and adhered to each other. Therefore, the glittering material tends to be hardly applied to the skin and deteriorated in handing properties, so that it tends to be difficult for such a glittering material to exhibit properties inherent thereto. In addition, since the pearlescent pigment or the lame agent tends to have no adhesiveness owing to its constituents, there tends to occur such a problem that the pearlescent pigment or the lame agent is likely to fall off from the skin, so that the makeup cosmetic coating shows low retentivity on the skin and fails to retain a good coating film state immediately after applying makeup.

On the other hand, in the present invention, in the case where the glitter pigment is contained as the aforementioned colorant, it is possible to uniformly apply a desired amount of the glitter pigment to the colored nonwoven fabric in a more convenient manner than subsequently putting the glitter pigment on the colored nonwoven fabric. In addition, since the glitter pigment is entangled and retained in the nanofibers and therefore hardly peeled off therefrom even by surface rubbing after attaching the colored nonwoven fabric to the skin, it is possible to exhibit the effect of suppressing falling-off of the glitter pigment from the colored nonwoven fabric and maintain a good condition of the makeup cosmetic coating.

Moreover, since some of the glitter pigments have a high surface hardness, for example, in the case where the colored nonwoven fabric is produced by the below-mentioned electrospinning method, it is possible to attain the effect of allowing the colored nonwoven fabric to exhibit excellent releasability when releasing and removing the colored nonwoven fabric from a collector.

The aforementioned glitter pigment may be uniformly contained over a whole portion of the colored nonwoven fabric irrespective of the uneven shape formed on the colored nonwoven fabric. However, from the viewpoint of improving a sense of unity of the colored nonwoven fabric with the skin in appearance, a resilient feel of the skin and a skin age, it is preferred that the glitter pigment is contained in the convex portions of the uneven shape of the colored nonwoven fabric, and more preferably in the surface of the convex portions. By incorporating the glitter pigment in the convex portions of the uneven shape of the colored nonwoven fabric, it is possible to suitably adjust the difference in lightness ($L^*_1$-$L^*_2$) between the convex portions and the concave portions.

As the aforementioned pearlescent pigment, there may be mentioned scale-like pigments; and scale-like coated pigments prepared by forming a coating layer of titanium oxide, iron oxide, etc., on the surface of the scale-like pigment as a substrate.

The aforementioned coated pigments are constituted of a low-refractive index substrate and a high-refractive index coating layer, in which when light is incident, reflected light beams from the respective layers are strengthened each other to emit interfering light, i.e., pearlescent light. In this case, by controlling an optical film thickness of the coating layer, it is possible to control a color tone of the interfering light.

Examples of the substrate of the coated pigments include natural mica, synthetic mica, glass, silica, alumina and the like. The synthetic mica, glass, silica, alumina and the like contain no impurities, such as iron, etc., unlike the natural mica, and therefore can exhibit dullness-free pearlescent luster. Moreover, the glass substrate has high surface smoothness, and therefore can exhibit high-glittery pearlescent luster.

Specific examples of the coated pigments include inorganic particles, such as bismuth oxychloride, titanium oxide-coated bismuth oxychloride, titanated mica (titanium oxide-coated mica), red iron oxide-coated mica, iron oxide-coated mica, iron oxide-coated titanated mica, organic pigment-coated titanated mica, silicic acid/titanium-treated mica, titanium oxide-coated talc, silicon dioxide/red iron oxide-treated aluminum, titanium oxide-coated glass powder, etc.; aluminum flakes whose surface is coated with an organic resin, such as polyethylene terephthalate, etc.; and the like.

In addition, there may also be used pigments of such a type that the color tone of interfering light varies depending upon observation angle, and commercially available pigments coated with a metal, such as gold, silver, etc.

The average primary particle size of the aforementioned pearlescent pigments is preferably not more than 100 μm, more preferably not more than 50 μm and even more preferably not more than 30 μm, and is also preferably not less than 1 μm, more preferably not less than 3 μm, even more preferably not less than 5 μm and further even more preferably not less than 10 μm, from the viewpoint of rendering the pigment less-visible owing to its size compatible with that of the 2nd relief of the skin, from the viewpoint of allowing the colored nonwoven fabric to exhibit a good gloss feel and a good transparent feel as well as from the viewpoint of improving a sense of unity of the colored nonwoven fabric with the skin in appearance, a resilient feel of the skin and a skin age.

The aspect ratio of the aforementioned pearlescent pigments which is represented by a ratio of the average primary particle size to an average thickness of the pearlescent pigment is preferably not less than 5, more preferably not less than 10 and even more preferably not less than 15, and is also preferably not more than 80, more preferably not more than 70 and even more preferably not more than 60.

The average primary particle size and the average thickness of the pearlescent pigments may be measured by the method described in Examples below.

Examples of commercially available products of the pearlescent pigment include "TWINCLEPEARL" series products and "FANTASPEARL" series products both available from Nihon Koken Kogyo Co., Ltd., "METASHINE" series products available from Nippon Sheet Glass Co., Ltd., and the like.

The aforementioned lame agents are prepared by subjecting a film substrate formed mainly of a polymer, such as polyethylene terephthalate (PET), polyvinyl chloride, etc., to emboss processing etc. for forming fine grooves therein, etc., and then cutting the thus processed film substrate into an optional shape (such as a rectangular shape, a reed shape, a square shape, a hexagonal shape, a star shape, a heart shape, etc.) and an optional size.

The lame agents may be of such a transparent type as prepared by alternately laminating two kinds of polymers (for example, such as PET/PMMA) up to about 100 to 300 layers to increase the number of interfaces thereof and thereby emit strong interfering light, in which the thickness of the film is controlled to adjust a color tone of the interfering light.

In addition, the lame agents may also be of such a type as prepared by vapor-depositing a metal, such as aluminum, gold, silver, etc., on a PET film and then laminating a polymer on the metal-deposited film to exhibit a strong metallic luster. These lame agents may be colored to impart a chromatic color appearance thereto.

As the metal vapor-deposited type lame agents, there may also be used commercially available products whose surface is processed into a microfine constant shape to create a hologram-like glitter feel.

The average particle size (average primary particle size) of the aforementioned lame agents is preferably not more than 750 μm, more preferably not more than 500 μm, even more preferably not more than 300 μm and further even more preferably not more than 150 μm, and is also preferably not less than 10 μm, more preferably not less than 20 μm and even more preferably not less than 30 μm, from the viewpoint of rendering the lame agents less-visible owing to its size compatible with that of the 2nd relief of the skin, from the viewpoint of allowing the colored nonwoven fabric to exhibit a good gloss feel and a good transparent feel as well as from the viewpoint of improving a sense of unity of the colored nonwoven fabric with the skin in appearance, a resilient feel of the skin and a skin age.

The average thickness of the aforementioned lame agents is preferably not less than 3 μm, more preferably not less than 5 μm and even more preferably not less than 10 μm, and is also preferably not more than 50 μm, more preferably not more than 40 μm and even more preferably not more than 30 μm.

The average particle size (average primary particle size) and the average thickness of the lame agents may be measured by the method described in Examples below.

Examples of commercially available products of the lame agents include "DAIYA HOLOGRAM" series products and "DIAMOND PIECE" series products both available from Daiya Industry Co., Ltd., and the like.

The colorant may be used alone or in combination of any two or more kinds thereof according to the color of the aimed colored nonwoven fabric. From the viewpoint of enhancing a sense of unity of the colored nonwoven fabric with the skin in appearance when attached to the skin, two or more colorants that are different in color from each other are preferably used in combination. For example, although a combination of a red colorant, a yellow colorant and a black colorant is generally used to adjust a color of the skin, a blue colorant or a white colorant may also be used in combination with these colorants.

(Other Components)

The colored nonwoven fabric of the present invention may also contain the other components in addition to the nanofibers formed of the colorant and the polymer compound A. Examples of the other components include powder components other than the aforementioned colorant (e.g., resin powders, such as a polyethylene resin powder or a silicone-based resin powder, etc.), as well as a crosslinking agent, a fragrance, a surfactant and an antistatic agent. The crosslinking agent may be used, for example, for the purpose of subjecting the aforementioned partially saponified polyvinyl alcohol to crosslinking reaction to render the polyvinyl alcohol water-insoluble. The other components except for the powder components other than the aforementioned colorant may be contained in the colored nonwoven fabric in such an amount that a total content of other components in the colored nonwoven fabric preferably falls within the range of not less than 0.01% by mass and not more than 2% by mass.

The aforementioned colorant is preferably used in the form of polymer particles containing the colorant (hereinafter also referred to as "colorant-containing polymer particles") from the viewpoint of achieving uniform coloration as well as from the viewpoint of improving water resistance of the resulting colored nonwoven fabric. The colorant-containing polymer particles may have any configuration as long as the particles are formed of the colorant and a dispersive polymer. Examples of the configuration of the colorant-containing polymer particles include the particle configuration in which the colorant is coated with the dispersive polymer, the particle configuration in which the colorant is enclosed in the dispersive polymer, the particle configuration in which the colorant is uniformly dispersed in the dispersive polymer, and the particle configuration in which the colorant is exposed onto the surface of the respective polymer particles, etc., as well as a mixture of these particle configurations.

The dispersive polymer constituting the colorant-containing polymer particles as used herein means a polymer with which the colorant can be dispersed in a medium. From the viewpoint of improving dispersibility of the colorant, the dispersive polymer is preferably an ionic group-containing polymer. As the ionic group-containing polymer, there may be used an anionic group-containing anionic polymer and a cationic group-containing cationic polymer.

[Anionic Polymer]

The anionic polymer preferably includes those polymers containing a group that is capable of releasing hydrogen ions upon dissociation thereof to allow the polymer to exhibit acidity, such as a carboxy group (—COOM), a sulfonic acid group (—$SO_3M$), a phosphoric acid group (—$OPO_3M_2$), etc., or those polymers containing an acid group including dissociated ion forms of these groups (such as —$COO^-$, —$SO_3^-$, —$OPO_3^{2-}$ and —$OPO_3^-M$), and the like. In the aforementioned chemical formulae, M is a hydrogen atom, an alkali metal, ammonium or an organic ammonium.

Specific examples of the basic skeleton of the anionic polymer include an acrylic polymer, a polyester, a polyurethane, and the like. Of these polymers, preferred is the acrylic polymer.

More specifically, the anionic polymer is preferably an anionic acrylic polymer containing a constitutional unit derived from an acid group-containing monomer.

As the acid group-containing monomer, preferred is a carboxy group-containing monomer, more preferred is at least one monomer selected from the group consisting of (meth)acrylic acid, crotonic acid, itaconic acid, maleic acid, fumaric acid, citraconic acid and 2-methacryloyloxymethylsuccinic acid, and even more preferred is (meth)acrylic acid.

The term "(meth)acrylic acid" as used herein means at least one compound selected from the group consisting of acrylic acid and methacrylic acid.

The anionic polymer is preferably a polymer containing the constitutional unit derived from the acid group-containing monomer and a constitutional unit derived from a (meth)acrylic acid alkyl ester; more preferably a polymer containing the constitutional unit derived from the acid group-containing monomer, the constitutional unit derived from the (meth)acrylic acid alkyl ester and a constitutional unit derived from a (N-alkyl)(meth)acrylamide; even more preferably a (meth)acrylic acid/(meth)acrylic acid alkyl ester/(N-alkyl)(meth)acrylamide copolymer; and further even more preferably an acrylic acid/acrylic acid alkyl ester/(N-alkyl)acrylamide copolymer.

Examples of commercially available products of the anionic acrylic polymer include ((meth)acrylic acid/(meth) acrylic acid alkyl ester/(N-alkyl)alkyl acrylamide) copolymer AMP, such as "Plascize L-9909B" available from GOO Chemical Co., Ltd., and the like. Examples of the other polymers containing a constitutional unit derived from acrylic acid or methacrylic acid as an anionic group thereof which can be used in the cosmetic applications include "Aniset KB-100H" and "Aniset NF-1000" both available from Osaka Organic Chemical Industry Ltd.; "Ultrahold 8", "Ultrahold Strong" and "Ultrahold Power" all available from BASF; "Plascize L-9900", "Plascize L-9540B", "Plascize L-9600U", "Plascize L-9715", "Plascize L-53", "Plascize L-6330", "Plascize L-6466", "Plascize L-6740B", "Plascize L-53D for Color A" and "Plascize L-75CB" all available from GOO Chemical Co., Ltd.; and the like.

[Cationic Polymer]

The cationic polymer is preferably a polymer containing a cationic group, such as a protonic acid salt of a primary, secondary or tertiary amino group, and a quaternary ammonium group, etc.

As the cationic polymer, there may be mentioned a natural cationic polymer and a synthetic cationic polymer.

Examples of the natural cationic polymer include a polymer obtained from a natural substance by subjecting the substance to treatments such as extraction, refining, etc., and a modified polymer obtained by chemically modifying the polymer, e.g., a polymer containing a glucose residue in a skeleton of the polymer. Specific examples of the natural cationic polymer include cationized guar gum; cationized tara gum; cationized locust bean gum; cationized cellulose; cationized hydroxyalkyl cellulose; cationic starch; and the like.

Examples of the synthetic cationic polymer include polyethyleneimine, polyallylamine or an acid-neutralized product thereof, a polyglycol-polyamine condensate, cationic polyvinyl alcohol, cationic polyvinyl pyrrolidone, a cationic silicone polymer, a 2-(dimethylamino)ethyl methacrylate polymer or an acid-neutralized product thereof, poly(trimethyl-2-methacryloyloxyethyl ammonium chloride), an amine/epichlorohydrin copolymer, an N,N-dimethylaminoethyl methacrylate diethyl sulfuric acid salt/vinyl pyrrolidone copolymer, an N,N-dimethylaminoethyl methacrylate diethyl sulfuric acid salt/N,N-dimethyl acrylamide/dimethacrylic acid polyethylene glycol copolymer, poly(diallyl dimethyl ammonium chloride), a diallyl dimethyl ammonium chloride/acrylamide copolymer, a diallyl dimethyl ammonium chloride/sulfur dioxide copolymer, a diallyl dimethyl ammonium chlorid/hydroxyethyl cellulose copolymer, a 1-allyl-3-methyl imidazolium chloride/vinyl pyrrolidone copolymer, an alkylamino (meth)acrylate/vinyl pyrrolidone copolymer, an alkylamino (meth)acrylate/vinyl pyrrolidone/vinyl caprolactam copolymer, a (3-(meth)acrylamido propyl)trimethyl ammonium chloride/vinyl pyrrolidone copolymer, an alkylaminoalkyl acrylamide/alkyl acrylamide/(meth)acrylate/polyethylene glycol (meth)acrylate copolymer, and the like. These synthetic cationic polymers may be used alone or in combination of any two or more thereof.

As commercially available products of the cationic polymer, preferred are those cationic polymers that can be used in the cosmetic applications. Examples of the commercially available products of the cationic polymer include "H.C. Polymer 3M" and "H.C. Polymer 5" both available from Osaka Organic Chemical Industry Ltd.; "Plascize L-514"

available from GOO Chemical Co., Ltd.; and the like. Among these cationic polymers, from the viewpoint of improving a sense of unity with the skin in appearance, a gloss feel and a transparent feel of the resulting colored nonwoven fabric, preferred is a cationic silicone polymer.

The cationic silicone polymer is preferably a poly(N-acylalkyleneimine)/organopolysiloxane copolymer containing an organopolysiloxane segment (x), and a poly(N-acylalkyleneimine) segment (y) composed of an alkylene group containing a cationic nitrogen atom bonded to at least one silicon atoms of the segment (x) and an N-acylalkyleneimine repeating unit represented by the following general formula (1-1).

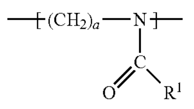

(1-1)

In the formula (1-1), $R^1$ is a hydrogen atom, an alkyl group having not less than 1 and not more than 22 carbon atoms, an aryl group having not less than 6 and not more than 22 carbon atoms, or an arylalkyl or alkylaryl group having not less than 7 and not more than 22 carbon atoms; and a is a number of 2 or 3.

In the formula (1-1), $R^1$ is preferably an alkyl group having not less than 1 and not more than 3 carbon atoms and more preferably an ethyl group, and a is preferably 2.

As the organopolysiloxane forming the segment (x), there may be mentioned, for example, a compound represented by the following general formula (1-2):

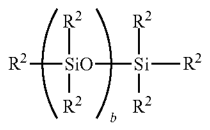

(1-2)

In the formula (1-2), $R^2$ is an alkyl group having not less than 1 and not more than 22 carbon atoms, a phenyl group or an alkyl group containing a nitrogen atom, and a plurality of $R^2$ groups may be the same or different from each other, with the proviso that at least one of the $R^2$ groups is an alkyl group containing a cationic nitrogen atom; and b is a number of not less than 100 and not more than 5,000.

The poly(N-acylalkyleneimine)/organopolysiloxane copolymer is preferably a copolymer that is formed by bonding the segment (y) to at least one of the silicon atoms present at a terminal end or side chain of the segment (x) through the alkylene group containing the cationic nitrogen atom.

The mass ratio of the content of the segment (x) to the total content of the segment (x) and the segment (y) [content of segment (x)/total content of segment (x) and segment (y)] in the poly(N-acylalkyleneimine)/organopolysiloxane copolymer is preferably not less than 0.1, more preferably not less than 0.3 and even more preferably not less than 0.4, and is also preferably not more than 0.99, more preferably not more than 0.95, even more preferably not more than 0.9, further even more preferably not more than 0.8 and still further even more preferably not more than 0.7.

In the present specification, the mass ratio [content of segment (x)/total content of segment (x) and segment (y)] means a ratio of a mass (Mx) of the segment (x) to a total amount of the mass (Mx) of the segment (x) and a mass (My) of the segment (y) in the poly(N-acylalkyleneimine)/organopolysiloxane copolymer.

The mass ratio [content of segment (x)/total content of segment (x) and segment (y)] may be calculated from an integration ratio between the alkyl group or the phenyl group in the segment (x) and the methylene group in the segment (y) which may be determined by a nuclear magnetic resonance ($^1$H-NMR) analysis in which the poly(N-acylalkyleneimine)/organopolysiloxane copolymer is dissolved in deuterated chloroform to prepare a 5% by mass solution thereof, and the thus obtained solution is subjected to the NMR analysis.

The weight-average molecular weight of the poly(N-acylalkyleneimine)/organopolysiloxane copolymer is preferably not less than 10,000, more preferably not less than 50,000 and even more preferably not less than 70,000, and is also preferably not more than 1,000,000, more preferably not more than 500,000 and even more preferably not more than 200,000. The weight-average molecular weight of the poly(N-acylalkyleneimine)/organopolysiloxane copolymer may be calculated from the weight-average molecular weight of the organopolysiloxane forming the segment (x) and the aforementioned mass ratio [content of segment (x)/total content of segment (x) and segment (y)].

Examples of the suitable poly(N-acylalkyleneimine)/organopolysiloxane copolymer include a poly(N-formylethyleneimine)/organopolysiloxane copolymer, a poly(N-acetylethyleneimine)/organopolysiloxane copolymer, a poly(N-propionylethyleneimine)/organopolysiloxane copolymer, and the like.

The poly(N-acylalkyleneimine)/organopolysiloxane copolymer may be produced by the method in which the poly(N-acylalkyleneimine) as a ring-opening polymerization product of a cyclic iminoether is reacted with the organopolysiloxane forming the segment (x). More specifically, the poly(N-acylalkyleneimine)/organopolysiloxane copolymer may be produced, for example, by the method described in JP 2011-126978A. The poly(N-acylalkyleneimine)/organopolysiloxane copolymer as the cationic silicone polymer may be used alone or in combination of any two or more kinds thereof.

Incidentally, the weight-average molecular weight of the dispersive polymer other than the aforementioned cationic silicone polymer may be measured by gel permeation chromatography [GPC apparatus: "HLC-8320GPC" available from Tosoh Corporation; columns: "TSKgel Super AWM-H", "TSKgel Super AW3000" and "TSKgel guardcolumn Super AW-H" all available from Tosoh Corporation; flow rate: 0.5 mL/min] using a solution prepared by dissolving phosphoric acid and lithium bromide in N,N-dimethylformamide such that concentrations of phosphoric acid and lithium bromide in the resulting solution are 60 mmol/L and 50 mmol/L, respectively, as an eluent, and using kits of monodisperse polystyrenes having previously known molecular weights [PStQuick B (F-550, F-80, F-10, F-1, A-1000), PStQuick C (F-288, F-40, F-4, A-5000, A-500)] all available from Tosoh Corporation as a reference standard substance.

Upon the aforementioned measurement of the weight-average molecular weight of the polymer, as a sample to be measured, there can be used a solution prepared by mixing 0.1 g of the polymer with 10 mL of the aforementioned eluent in a glass vial, stirring the resulting mixture with a magnetic stirrer at 25° C. for 10 hours, and then subjecting the mixture to filtration treatment through a syringe filter "DISMIC-13HP" (PTFE; 0.2 μm) available from Advantec Co., Ltd.

In the case where the aforementioned colorant is used in the form of pigment particles or colorant-containing polymer particles, it is preferred that the size of the pigment particles or the colorant-containing polymer particles (hereinafter collectively referred to as "colorant particles") is generally similar to the thickness (fiber diameter) of the nanofibers, or smaller than or larger than the thickness of the nanofibers. In the case where the size of the colorant particles is generally similar to or smaller than the thickness of the nanofibers, it is possible to reduce occurrence of the color unevenness of the colored nonwoven fabric on the skin even when the colored nonwoven fabric is of a thin sheet shape. On the other hand, in the case where the size of the colorant particles is larger than the thickness of the nanofibers, it is possible to express and create an uneven shape on the surface of the nanofibers due to the colorant particles. By expressing and creating the uneven shape, irregular reflection of light is caused on the surface of the nanofibers, so that it is possible to improve concealability, a sense of unity with the skin in appearance, a gloss feel and a transparent feel of the colored nonwoven fabric.

In the case where the aforementioned colorant is used in the form of the colorant particles, the volume-average particle size of the colorant particles is preferably not less than 10 nm and more preferably not less than 50 nm, and is also preferably not more than 1,000 nm and more preferably not more than 900 nm.

In addition, in the case where the thickness of the nanofibers lies within the below-mentioned range, the volume-average particle size of the colorant particles relative to the thickness of the nanofibers as calculated in terms of a ratio thereof assuming that the thickness of the nanofibers is regarded as being 100% is preferably not less than 20% and more preferably not less than 30%, and is also preferably not more than 95% and more preferably not more than 90%.

When the volume-average particle size of the colorant particles lies within the aforementioned range, there may be formed such a configuration that the colorant particles are partially enclosed in the nanofibers, and it is therefore possible to suppress aggregation of the colorant particles, reduce occurrence of the color unevenness of the colored nonwoven fabric on the skin even in the case where the colored nonwoven fabric has a thin sheet shape, and thereby enhance a sense of unity of the colored nonwoven fabric with the skin in appearance. Furthermore, in such a case, it is possible to wet the colored nonwoven fabric even with a small amount of a liquid material when attached to the skin.

The volume-average particle size of the colorant particles may be measured by the method described in Examples below.

The content of the colorant in the colored nonwoven fabric of the present invention may vary depending upon the kind of colorant used, and is preferably not less than 1% by mass and more preferably not less than 15% by mass, and is also preferably not more than 60% by mass, more preferably not more than 55% by mass and even more preferably not more than 50% by mass, from the viewpoint of allowing the colorant to exhibit a sufficient coloring power.

In the present specification, when using two or more kinds of colorants, the content of the colorant as used herein means a total content of the two or more kinds of colorants, which is also hereinafter defined in the same way.

The content of the colorant based on the nanofibers in the colored nonwoven fabric of the present invention may vary depending upon the kind of colorant used. The content of the colorant based on the nanofibers in the colored nonwoven fabric as calculated in terms of a ratio thereof assuming that the content of the nanofibers in the colored nonwoven fabric is regarded as being 100% by mass is preferably not less than 50% by mass, more preferably not less than 55% by mass and even more preferably not less than 60% by mass, and is also preferably not more than 110% by mass, more preferably not more than 100% by mass, even more preferably not more than 95% by mass and further even more preferably not more than 90% by mass, from the viewpoint of allowing the colorant to exhibit a sufficient coloring power. That is, the content of the colorant based on the nanofibers in the colored nonwoven fabric according to the present invention as calculated on the basis of 100 parts by mass of the nanofibers in the colored nonwoven fabric is preferably not less than 50 parts by mass, more preferably not less than 55 parts by mass and even more preferably not less than 60 parts by mass, and is also preferably not more than 110 parts by mass, more preferably not more than 100 parts by mass, even more preferably not more than 95 parts by mass and further even more preferably not more than 90 parts by mass, from the same viewpoint as described above.

In the present invention, in the case where the organic pigment, lake pigment or dye is used as the colorant, the colored nonwoven fabric tends to be readily colored. Therefore, in such a case, even when the content of the colorant based on the nanofibers as calculated in terms of a ratio thereof assuming that the content of the nanofibers in the colored nonwoven fabric is regarded as being 100% by mass, is as small as about not less than 1% by mass and not more than 10% by mass, that is, the content of the colorant based on the nanofibers in the colored nonwoven fabric as calculated on the basis of 100 parts by mass of the nanofibers in the colored nonwoven fabric is as small as about not less than 1 part by mass and not more than 10 parts by mass, it is possible to obtain the colored nonwoven fabric that is uniformly colored without color unevenness.

The content of the colorant in the colored nonwoven fabric and the content of the colorant based on the nanofibers may be measured as follows. That is, the resulting colored nonwoven fabric is dipped and dissolved in a solvent that is capable of dissolving the colored nonwoven fabric, if required while further applying a mechanical force by means of an ultrasonic cleaning device, etc., thereto, and then filtration of the obtained solution and washing of the filtration residue are repeated to separate solid components therefrom, followed by drying the solid components to measure a mass of the thus dried product by using scales, etc.

[Process for Producing Colored Nonwoven Fabric]

The process for producing the colored nonwoven fabric according to the present invention includes an electrospinning step of injecting at least the polymer compound A by an electrospinning method to deposit the nanofibers on a surface of a collector (hereinafter also referred to merely as an "electrospinning step"); and an L* value adjusting step of coloring the nanofibers such that an L* value of convex portions of the resulting colored nonwoven fabric is higher than an L* value of concave portions thereof (hereinafter also referred to merely as an "L* value adjusting step") from the viewpoint of improving rub fastness of the resulting colored nonwoven fabric and allowing the colored nonwoven fabric to exhibit a good gloss feel and a good transparent feel as well as from the viewpoint of improving a sense of unity of the colored nonwoven fabric with the skin in appearance, a resilient feel of the skin and a skin age.

The collector preferably has an uneven structure on at least a part of a surface thereof on which the nanofibers are to be deposited, from the same viewpoint as described above.

The shape of the collector used in the present invention as a whole is not particularly limited as long as the uneven structure is formed on at least a part of the surface of the collector. For example, the collector may be of either a flat plate shape or a curved shape.

The collector used in the present invention preferably has the uneven structure. The ascertainment and measurement of the shape of the uneven structure of the collector are implemented by 3D measurement based on sectional profile using an industrial microscope "LEXT-OLS5000-SAT" available from Olympus Corporation as described in Examples below, in which the measurement is conducted at 20 points as measurement objects selected per one collector as the sample to be measured to calculate an average value thereof. Thus, by conducting the measurement at 20 points on the collector, even if the collector has a curved shape, the ascertainment and measurement of the shape of the uneven structure of the collector can be performed exclusive of adverse influence of the curved shape.

In addition, in the process for producing the colored nonwoven fabric having two or more uneven shapes, such a colored nonwoven fabric may be obtained by using a collector having two or more uneven structures.

In the case of the colored nonwoven fabric set including the two or more colored nonwoven fabrics, it is preferred that two or more collectors that are different in uneven structure from each other are used to obtain the two or more colored nonwoven fabrics that are different in uneven shape from each other.

The term "electrospinning method" as used in the present invention means such a method in which a high voltage is applied to a solution containing a polymer compound or a melt of the polymer compound obtained by heating the polymer compound to inject a spinning liquid formed of the solution or melt and thereby form nanofibers, followed by collecting and depositing the nanofibers on a collector as a counter electrode to obtain a nonwoven fabric thereon.

<Electrospinning Method>

The process for producing the colored nonwoven fabric according to the present invention includes the electrospinning step of injecting at least the polymer compound A by an electrospinning method to deposit the nanofibers on the surface of the collector.

The uneven structure of the collector used in the production process of the present invention is preferably such an uneven structure that imitates a surface configuration of the skin, from the viewpoint of improving rub fastness of the resulting colored nonwoven fabric and allowing the colored nonwoven fabric to exhibit a good gloss feel and a good transparent feel as well as from the viewpoint of improving a sense of unity of the colored nonwoven fabric with the skin in appearance, a resilient feel of the skin and a skin age.

The surface configuration of the skin as used herein has the same meaning as described previously.

(Collector)

From the same viewpoint as described above, as the collector having the uneven structure that imitates the surface configuration of the skin, there is preferably used a collector provided on a surface thereof with a concavo-convex region which is constituted of a plurality of convex portions, and there can be used a collector whose surface is subjected to emboss processing that is called texturing. The textured surface of the collector is so formed that concave portions and convex portions thereon respectively have a smooth surface, and therefore the uneven shape of the collector can be clearly recognized by visual observation even though the difference in level (unevenness) between the concave and convex portions is not so large, so that it is possible to form the uneven shape imitating the surface configuration of the skin on the colored nonwoven fabric.

The texture depth (a distance from a highest apex to a lowest valley bottom as viewed in section) of the collector is preferably not less than 30 μm and more preferably not less than 70 μm, and is also preferably not more than 300 μm and more preferably not more than 200 μm.

The material of the collector is not particularly limited, and the collector may be formed of a resin or a metal. Among these materials, from the viewpoint of forming the colored nonwoven fabric that contains a portion corresponding to the skin grooves where the nanofibers are relatively densely present and a portion corresponding to the skin hills where the nanofibers are relatively sparsely present, and improving flexibility and rub fastness of the colored nonwoven fabric, the resin is preferably used. Examples of the resin used for the collector include polyamides, such as nylon 66, etc.; polycarbonates; and the like.

The uneven structure of the collector may be ascertained and measured by the method described in Examples below.

Examples of the collector having a textured surface include molded articles, such as textured artificial leathers, etc., or texturing molds used in the texturing process, and the like. More specifically, as the collector, there may be used, for example, a grain-like artificial leather having a leather pattern used for automobile parts, etc., and a mold used for producing the grain-like artificial leather.

In the case where the mold used for producing the grain-like artificial leather is used as the collector, it is preferred that the information of a texture (unevenness) of a skin portion of the user to which the colored nonwoven fabric is desirably attached is photographed, and the photographed information is analyzed to design a textured shape of the collector to be used such that the pitch and height of the unevenness on the resulting colored nonwoven fabric are identical to those on the skin portion to which the colored nonwoven fabric is desirably attached when transferring the colored nonwoven fabric to the skin.

In addition, when using the collector having the textured surface, there can be attained such an effect due to its rub fastness that the uneven shape of the surface of the colored nonwoven fabric which is derived from the uneven structure of the collector is hardly wounded, or the defects produced are less remarkable even when it is wounded. The reason why the uneven shape of the surface of the colored nonwoven fabric is hardly wounded is considered as follows. That is, it is considered that the convex portions of the uneven shape of the surface of the colored nonwoven fabric undergo point contact and therefore become slippery, and further the convex portions are deformable so that the stress applied thereto can be absorbed and relieved. Moreover, it is considered that since a continuous plane of the colored nonwoven fabric having the uneven shape is located at a position lower than its convex portions, the plane portion of the colored nonwoven fabric tends to be hardly wounded, so that the effect of rendering the defects produced less remarkable can be attained.

Examples of commercially available products of the grain-like artificial leather include "SUPULARE" available from IDEATEX Japan Co., Ltd., "NEOSOFEEL" available from SEIREN Co., Ltd., "ECSAINE" available from TORAY Industries, Inc., and the like.

Examples of commercially available products of the mold used for producing the grain-like artificial leather include “TEXTURE SAMPLE MIJ” series products available from Mold-Tech Japan Co., Ltd., and the like.

In the case where the colored nonwoven fabric has the uneven shape capable of reproducing the aforementioned 5th relief or the uneven shape capable of reproducing the aforementioned 2nd relief it is preferable to use the concavo-convex plate having the uneven structure capable of reproducing the aforementioned 5th relief or 2nd relief upon production thereof using an electrospinning method.

The aforementioned concavo-convex plate may be disposed on a collector and used to inject the spinning solution onto the concavo-convex plate by an electrospinning method. In addition, the aforementioned concavo-convex plate may also be used not only as the collector, but also as a mold for forming the uneven structure in emboss processing, etc. From the viewpoint of improving rub fastness of the resulting colored nonwoven fabric, allowing the colored nonwoven fabric to exhibit a good sense of unity with the skin in appearance, a good gloss feel and a good transparent feel, and further improving a resilient feel of the skin and a skin age, the aforementioned concavo-convex plate is preferably used as the collector. More specifically, in the production process of the present invention, the electrospinning step is preferably the step of depositing the nanofibers on the uneven structure-bearing surface of the aforementioned concavo-convex plate used as the collector. By conducting such a step, it is possible to obtain the colored nonwoven fabric that is formed on the aforementioned concavo-convex plate.

As the vertical cross-sectional shape of the respective concave portions as taken on a plane cut in parallel with the Z-axis direction that is the direction of a thickness of the concavo-convex plate used as the collector, there may be mentioned a semicircular shape, a semielliptical shape, a triangular shape, a quadrangular shape, such as a square shape, a rectangular shape, a trapezoidal shape, etc., and the like. Among these shapes, from the viewpoint of facilitating release of the resulting nonwoven fabric from the concavo-convex plate, the side face extending from an opening to a bottom of the respective convex portions is an inclined surface having a gradient. The vertical cross-sectional shape of the respective concave portions is preferably a semicircular shape, a semielliptical shape, an inverted triangular shape or an inverted trapezoidal shape from the same viewpoint as described above, and more preferably an inverted trapezoidal shape from the viewpoint of improving rub fastness of the resulting nonwoven fabric, allowing the nonwoven fabric to exhibit a good sense of unity with the skin in appearance, a good gloss feel and a good transparent feel, and further improving a skin texture and suppressing occurrence of skin shine.

Incidentally, in the case where the vertical cross-sectional shape is an inverted triangular shape or an inverted trapezoidal shape, corner portions located at lower positions of the inverted triangular shape or inverted trapezoidal shape may be formed into a slightly rounded shape.

In the case where the concavo-convex plate has the uneven structure capable of reproducing the aforementioned 5th relief or the uneven structure capable of reproducing the aforementioned 2nd relief as the shape of the three-dimensional structure of the respective concave portions of the concavo-convex plate, there may be mentioned a cylindrical shape, a semi-cylindrical shape, an elliptic cylindrical shape, a conical shape, a semi-conical shape, an elliptic conical shape, a truncated conical shape, a semi-truncated conical shape, an elliptic truncated conical shape, a prismatic shape, a pyramid shape, a truncated pyramid shape, and shapes similar to these shapes, as well as combinations of these shapes.

The shape of the three-dimensional structure of the respective concave portions of the concavo-convex plate whose vertical cross-sectional shape is an inverted trapezoid shape is preferably an inverted frustum shape whose opening area is larger than a bottom area thereof, and a generally inverted frustum shape similar thereto. Examples of the generally inverted frustum shape include an inverted truncated pyramidal shape, such as an inverted three-sided truncated pyramidal shape, an inverted four-sided truncated pyramidal shape, an inverted five-sided truncated pyramidal shape, an inverted six-sided truncated pyramidal shape, etc., and a generally inverted truncated pyramidal shape similar to these shapes, an inverted truncated conical shape, and a generally inverted truncated conical shape similar thereto, as well as combinations of these shapes. Among these shapes, from the viewpoint of improving rub fastness of the resulting colored nonwoven fabric, as well as from the viewpoint of allowing the colored nonwoven fabric to exhibit a good sense of unity with the skin in appearance, a good gloss feel and a good transparent feel, and further improving a skin texture and suppressing occurrence of skin shine, preferred are a generally inverted polygonal truncated pyramidal shape and a generally inverted truncated conical shape, and more preferred is a generally inverted polygonal truncated pyramidal shape.

The shape of the three-dimensional structure of the respective concave portions of the concavo-convex plate as the uneven structure capable of reproducing the aforementioned 5th relief is preferably a generally inverted polygonal truncated pyramidal shape or a generally inverted truncated conical shape, more preferably a generally inverted polygonal truncated pyramidal shape, even more preferably a generally inverted three-sided truncated pyramidal shape, a generally inverted rhombic truncated pyramidal shape or a generally inverted six-sided truncated pyramidal shape, and further even more preferably an inverted three-sided truncated pyramidal shape, an inverted rhombic truncated pyramidal shape or an inverted six-sided truncated pyramidal shape.

The shape of the three-dimensional structure of the respective concave portions of the concavo-convex plate as the uneven structure capable of reproducing the aforementioned 2nd relief is preferably a generally inverted polygonal truncated pyramidal shape, and more preferably a generally inverted six-sided truncated pyramidal shape.

In the case where the three-dimensional structure of the respective concave portions of the aforementioned uneven structure is a generally inverted frustum shape, a ratio of an average length of opening portions of the concave portions to an average length of bottom portions of the concave portions [average length of opening portions/average length of bottom portions] is preferably more than 1.0, and is also preferably not more than 3.0, more preferably not more than 2.0, even more preferably not more than 1.5 and further even more preferably not more than 1.3.

The average length of the opening portions and the average length of the bottom portions as used herein in the case where the shape of the three-dimensional structure of the respective concave portions is a generally inverted truncated conical shape, mean a diameter of a circle of the opening portion and a diameter of a circle of the bottom portion, respectively, whereas the average length of the opening portions and the average length of the bottom portions as used herein in the case where the shape of the three-dimensional structure of the respective concave portions is a generally inverted elliptic truncated conical shape mean an average value of a major axis diameter and a minor axis diameter of an ellipse of the opening portion and an average value of a major axis diameter and a minor axis diameter of an ellipse of the bottom portion, respectively. Also, the average length of the opening portions and the average length of the bottom portions as used herein in the case where the shape of the three-dimensional structure of the respective concave portions is a generally inverted polygonal truncated pyramidal shape, mean an average value of lengths of sides of a polygonal shape of the opening portion and an average value of lengths of sides of a polygonal shape of the bottom portion, respectively.

Figure 2:
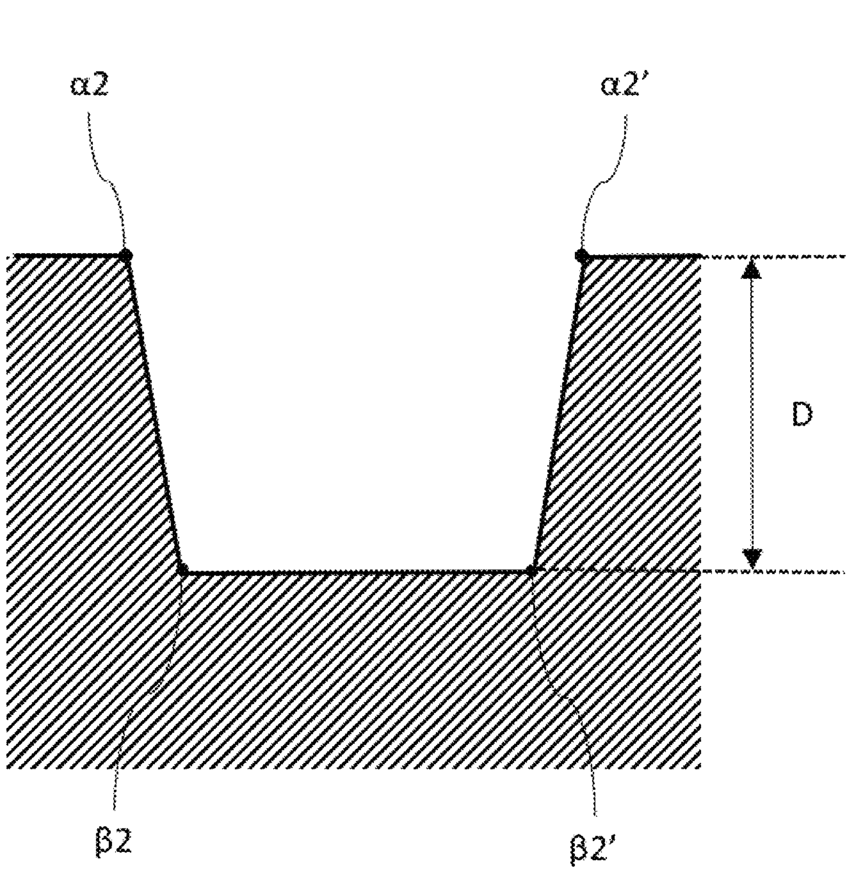
FIG. 2 is a vertical cross-sectional view of a concave portion of a concavo-convex plate used for production of a colored nonwoven fabric in the case where the concave portion has an inverted truncated conical shape.

For example, as shown in FIG. 2, in the case where the shape of the three-dimensional structure of the respective concave portions is a inverted truncated conical shape, the vertical cross-sectional shape as cut through a center of a circle of the structure is an inverted trapezoid shape. In this case, the distance between a point α2 and a point α2' is equal to the length of the opening portion, and the distance between a point β2 and a point β2' is equal to the length of the bottom portion.

Figure 3:
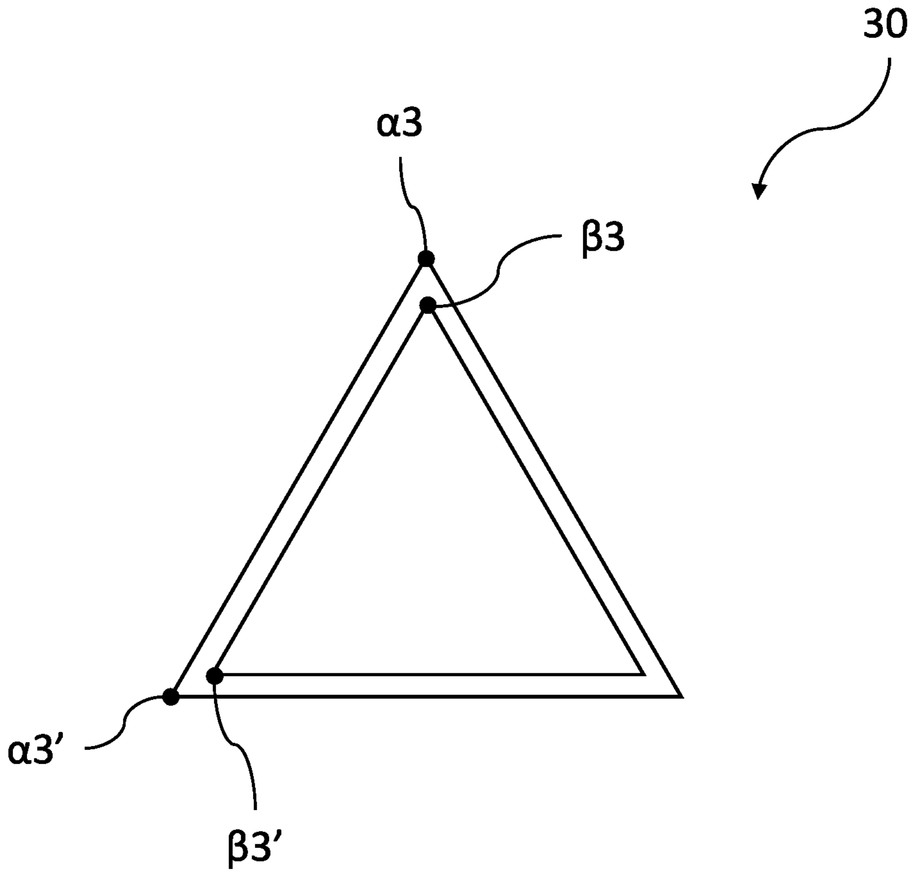
FIG. 3 is a top plan view of a concave portion of a concavo-convex plate used for production of a colored nonwoven fabric in the case where the concave portion has an inverted three-sided truncated pyramidal shape.

In addition, as shown in FIG. 3, in the case where the shape of the three-dimensional structure of the respective concave portions is a inverted regular triangular three-sided truncated pyramidal shape, the shape of the respective concave portions as viewed from above looks like overlapped two regular triangles that are different in size from each other. In this case, the distance between a point α3 and a point α3' is equal to the length of the opening portion, and the distance between a point β3 and a point β3' is equal to the length of the bottom portion.

The ascertainment and measurement of the aforementioned uneven structure may be carried out by the method described in Examples below.

In the case where the concave portions of the concavo-convex plate as the uneven structure capable of reproducing the aforementioned 5th relief respectively have a generally inverted frustum shape, the average length L(I) of the opening portions of the concave portions is preferably not less than 30 μm, more preferably not less than 50 μm and even more preferably not less than 100 μm, and is also preferably not more than 750 μm, more preferably not more than 500 μm and even more preferably not more than 300 μm.

In the case where the concave portions of the concavo-convex plate as the uneven structure capable of reproducing the aforementioned 5th relief respectively have a generally inverted frustum shape, the average length L(II) of the bottom portions of the concave portions is preferably not less than 20 μm, more preferably not less than 35 μm and even more preferably not less than 70 μm, and is also preferably not more than 525 μm, more preferably not more than 350 μm and even more preferably not more than 210 μm.

The ratio of the average length L(I) of the opening portions to the average length L(II) of the bottom portions [L(I)/L(II)] in the concave portions of the concavo-convex plate is preferably more than 1.0, and is also preferably not more than 3.0, more preferably not more than 2.0, even more preferably not more than 1.5 and further even more preferably not more than 1.3.

In the case where the concave portions of the concavo-convex plate as the uneven structure capable of reproducing the aforementioned 2nd relief respectively have a inverted frustum shape, the average length L(1) of the opening portions of the concave portions is preferably not less than 1 μm, more preferably not less than 5 μm, even more preferably not less than 10 μm and further even more preferably not less than 15 μm, and is also preferably not more than 60 μm, more preferably not more than 50 μm, even more preferably not more than 40 μm and further even more preferably not more than 30 μm.

In the case where the concave portions of the concavo-convex plate as the uneven structure capable of reproducing the aforementioned 2nd relief respectively have a inverted frustum shape, the average length L(2) of the bottom portions of the concave portions is preferably not less than 1 μm, more preferably not less than 3 μm and even more preferably not less than 10 μm, and is also preferably not more than 50 μm, more preferably not more than 30 μm and even more preferably not more than 20 μm.

The ratio of the average length L(1) of the opening portions to the average length L(2) of the bottom portions [L(1)/L(2)] in the concave portions of the concavo-convex plate is preferably more than 1.0, and is also preferably not more than 3.0, more preferably not more than 2.0, even more preferably not more than 1.5 and further even more preferably not more than 1.3.

The surface resistivity of the concavo-convex plate is preferably not more than $1\times10^{-2}\Omega/\square$ from the viewpoint of forming a nonwoven fabric in which the difference in density of nanofibers between concave portions and convex portions thereof is small, and even the concave portions have high toughness, and improving rub fastness of the resulting colored nonwoven fabric. Thus, the surface resistivity of the convex portions of the concavo-convex plate is adjusted to not more than $1\times10^{-2}\Omega/\square$, so that delivery of electrons to fibers taking on a positive electric charge which are spun from the capillary by electrospinning is rapidly conducted at the convex portions, deposition of the nanofibers on the concavo-convex plate is stabilized, and further deposition of the nanofibers on the convex portions is suppressed, whereby the uneven structure of the concavo-convex plate can be well transferred to the nonwoven fabric. From this viewpoint, the surface resistivity of the concavo-convex plate is more preferably not more than $0.5\times10^{-2}\Omega/\square$, even more preferably not more than $1\times10^{-3}\Omega/\square$ and further even more preferably not more than $0.5\times10^{-3}\Omega/\square$. The lower limit of the surface resistivity of the concavo-convex plate is not particularly limited, and is preferably not less than $5\times10^{-6}\Omega/\square$, more preferably not less than $1\times10^{-5}\Omega/\square$ and even more preferably not less than $5\times10^{-5}\Omega/\square$ from the viewpoint of facilitating production of the concavo-convex plate.

From the viewpoint of imparting a three-dimensional feel to the face, in the case where the glitter pigment is used as the colorant, by employing the concavo-convex plate having a surface resistivity that lies within the aforementioned range, it is possible to control the amount of the glitter pigment applied in the below-mentioned electrostatic powder spray-coating method. In particular, the pearlescent pigments or lame agents tend to be electrically charged owing to constituents thereof. However, by employing the high-conductive concavo-convex plate having a surface resistivity that lies within the aforementioned range, electrical charges on the glitter pigment tends to be eliminated, and overlapping between the particles tends to be minimized, so that the glitter pigment are more likely to exhibit properties inherent thereto, and further can be uniformly applied to the convex portions of the colored nonwoven fabric. In addition, by depositing the nanofibers against the glitter pigment applied onto the concavo-convex plate, by an electrospinning method, the glitter pigment is entangled in the nanofibers, and fixed in the colored nonwoven fabric, so that it is possible to suppress falling off of the glitter pigment from the makeup cosmetic coating.

The concavo-convex plate capable of satisfying the aforementioned surface resistivity is preferably formed of a resin or a metal which has a conductive layer, from the viewpoint of improving rub fastness of the resulting colored nonwoven fabric and allowing the colored nonwoven fabric to exhibit a good gloss feel and a good transparent feel as well as from the viewpoint of improving a sense of unity of the colored nonwoven fabric with the skin in appearance, a resilient feel of the skin and a skin age.

The electrical resistivity (volume resistivity) of the conductive layer as measured at 20° C. is preferably not more than $1.0\times10^{-6}$ Ω/m, more preferably not more than $1.0\times10^{-7}$ Ω/m, even more preferably not more than $5.0\times10^{-8}$ Ω/m, further even more preferably not more than $3.0\times10^{-8}$ Ω/m and still further even more preferably not more than $2.0\times10^{-8}$ Ω/m, and is also preferably not less than $1.0\times10^{-8}$ Ω/m, more preferably not less than $1.3\times10^{-8}$ Ω/m and even more preferably not less than $1.5\times10^{-8}$ Ω/m.

Examples of the material constituting the conductive layer include copper, iron, platinum, stainless steel, aluminum, gold, and the like. Among these materials, preferred are copper, iron and platinum, and more preferred is copper.

The thickness of the conductive layer may be selectively determined according to the material constituting the conductive layer and the average depth of the concave portions of the uneven structure of the concavo-convex plate so as to satisfy the aforementioned surface resistivity.

[Production of Concavo-Convex Plate]

Examples of the concavo-convex plate include a gravure plate produced by a laser plate making (etching) process or an engraving plate making process, a metal texturing mold, and the like. There may also be used a concavo-convex plate formed of a conductive material since it can exhibit the effects of the present invention by satisfying the aforementioned surface resistivity.

Among these plates, there is preferably used a conductive concavo-convex plate that is so designed as to adjust a pitch and a height of its unevenness to those identical to information of unevenness (texture information) of a skin portion of the user which has been photographed and analyzed and to which the nonwoven fabric is to be desirably put on when transferred.

The skin color is different between individuals, and even in the same person, the texture of the skin varies depending upon portions of a face or a body of the person, or change in influence of light on aging of the skin by exposure to ultraviolet radiation. For this reason, as specific a concrete example of the information concerning the texture of the skin to be attained, there may be mentioned the information concerning a texture of an inside skin portion of an upper arm which undergoes less tanning. By acquiring such a skin texture information, it is possible to attain information concerning the texture of the skin which suffers less aging as compared to a face, etc., though the texture of the skin is inherent to the individual person. In addition, in the case of the person who has maintained long hairstyles for a long period of time and therefore whose nape (backside of neck) is almost free of exposure to ultraviolet radiation, by attaining the information on the texture of the skin of the nape, it is possible to obtain information of the skin close to the information concerning the texture of the skin of a face of the person which undergoes no aging. Thus, by forming the concavo-convex plate on the basis of the thus obtained information concerning the texture of the skin and producing the colored nonwoven fabric using the concavo-convex plate, the resulting colored nonwoven fabric whose surface is formed into an uneven shape is attached to the skin.

The method of producing the concavo-convex plate may be appropriately selected according to the material of the concavo-convex plate, the shape of the respective concave portions of the concavo-convex plate, etc. As the method of obtaining the high-quality concavo-convex plate at low costs in a convenient manner, there may be used the method in which after applying a photosensitive agent to a plate having a conductive layer and then exposing the photosensitive agent to light, such as a laser, the resulting plate is subjected to chemical corrosion (chemical etching) with an acid. As one example of such a method, there may be mentioned a method of producing a gravure plate. In the method of producing a gravure plate, a copper-plating step, a polishing step and an etching step are conducted in sequence to form the concavo-convex plate. In the following, the copper-plating step, the polishing step and the etching step are sequentially explained.

[Copper-Plating Step]

First, a virgin roll to be processed for plate-making is subjected to ultrahigh precision cylindrical processing, and successively subjected to nickel plating and then copper plating to conduct correction of an eccentric amount of the roll.

Next, the roll for plate-making is subjected to Ballard process. The Ballard process is the method of manufacturing a gravure plate cylinder which has been invented by E. S. Ballard, Germany, in 1934, in which after polishing a copper-plated gravure cylinder (referred to as a copper-plated layer 1), a thin film of silver, etc., is subjected to displacement plating on the cylinder to form a release layer thereon, followed by further plating copper on the release layer until reaching a layer thickness (referred to as a copper-plated layer 2) capable of forming a desired plate and then polishing the copper-plated layer 2 to utilize the copper-plated layer 2 for plate making. After making use of the plated layer, by forming a cut in an edge of the plate cylinder, the copper-plated layer 2 can be easily released from the cylinder. By subjecting the plate cylinder again to formation of a copper-plated layer 2 thereon, the plate cylinder can be used for the next plate making process without any damages to an eccentric amount of the roll layer, etc. In addition, the plate released after the Ballard process can be used as an almost flat plate though it has a slight curvature. Therefore, the plate can be used as the concavo-convex plate of the present invention in an electrospinning method in which after forming the colored nonwoven fabric on the concavo-convex plate, the plate can also be used as a release sheet as described below.

The thickness of the copper-plated layer 2 after polishing is preferably controlled to the range of from X+20 μm to X+80 μm wherein X (μm) represents an average depth of the desired concave portions, from the viewpoint of improving handling properties of the concavo-convex plate after conducting the Ballard process and releasing the plate.

In addition, the portion of the copper-plated layer 2 having a thickness of about 20 to 30 μm is scraped off in the subsequent polishing step to smoothen the surface of the copper-plated layer 2, and therefore an initial plating thickness of the copper-plated layer 2 is preferably adjusted to the range of from X+40 μm to X+110 μm.

[Polishing Step]

Next, in order to enhance a dimensional accuracy of the cylinder, the roll for plate making is polished with a silicon carbide-based grind stone while measuring the diameter of the roll for plate making and thereby changing the grind stone from a coarse one to a fine one, and finally subjected to buffing to conduct mirror finish thereof.

[Etching Step]

Next, a photosensitive agent is applied onto the surface of the copper-plated layer 2 of the mirror-finished roll for plate making, and then a laser light is irradiated to the plate such that the portions of the photosensitive agent which correspond to the convex portions of the uneven structure are exposed to the laser light. Thereafter, the resulting roll is immersed in a developing liquid to dissolve the portions of the photosensitive agent which correspond to the concave portions of the uneven structure, so that a part of the surface of the copper-plated layer 2 is exposed outside. Then, when the roll is immersed in an etching liquid, although the portion of the copper-plated layer 2 which is still covered with the photosensitive agent remains unchanged, copper of the portion of the copper-plated layer 2 which is exposed outside, i.e., the portion thereof corresponding to the respective concave portions, is dissolved in the etching liquid to thereby form the concave portions. Moreover, the roll for plate making is immersed in a releasing liquid for the photosensitive agent to remove the photosensitive agent remaining on the copper-plated layer 2 therefrom to thereby form the concave portions on the roll for plate making.

Incidentally, the exposure accuracy of the laser light irradiated presently reaches a resolution of 25,400 dpi in the industrially available level, so that the shape of the respective concave portions can be designed as finely as up to the unit of 1 μm.

In addition, in general, upon production of the gravure plate used for gravure printing, after forming cells (concave portions) therein, a protective film, such as a chromium plated layer, etc., may be generally formed on the copper-plated layer on the surface of the roll in order to impart good printing durability to the resulting gravure plate in the gravure printing process.

However, upon production of the gravure plate as the concavo-convex plate used in the present invention, there is no fear that the surface of the plate is rubbed with a roll or a doctor blade, unlike in the gravure printing. In addition, when depositing the nanofibers on the gravure plate by electrospinning, the gravure plate acts as a cathode, and therefore can be prevented from suffering from corrosion by cathode protection, so that it is possible to omit the treatment for forming a protective film, such as a chromium-plated layer, etc.

In addition, in the case where the concavo-convex plate is used in the resin solution-type electrospinning method, it is also assumed that water is used as a solvent of the resin solution to be injected.

On the other hand, an etching liquid for etching copper which is used upon formation of the concave portions is partially incorporated into the metallic structure of the plate even after washing off the etching liquid, so that corrosion of the plate is accelerated more or less by water introduced thereinto by the electrospinning. However, the gravure plate acts as a cathode and exhibits a cathode protection effect. Therefore, even in the case of using the resin solution-type electrospinning method, it is possible to omit the treatment for forming a protective film, such as a chromium-plated layer, etc.

Moreover, by omitting the treatment for forming a protective film, such as a chromium-plated layer, etc., the uneven structure of the concavo-convex plate can be prevented from being flattened by filling the concave portions with the chromium-plated layer deposited, so that it is possible to produce a gravure plate having a more highly precise uneven structure as compared to the conventional gravure plates using in gravure printing. More specifically, for example, although a printing image area of a gravure plate subjected to chromium plating process has a width of 26.0 μm, a gravure plate subjected to no chromium plating process can be directly used as such with its printing image area having a width of 12.5 μm, so that it is possible to sufficiently utilize a potential ability of a processing accuracy of the laser light for formation of the uneven structure of the concavo-convex plate.

In the present invention, by repeating the steps including the application of the photosensitive agent through the chemical etching, it is possible to form a concave portion having another shape inside the previously formed respective concave portions in an overlapped manner. The method of forming the concave portions by chemical etching may be used not only for producing the gravure plate, but also for producing a textured concavo-convex plate used for production of a texturing mold that is in turn used for production of an artificial leather. The texturing mold has a complicated uneven structure by repeatedly conducting the etching step in two or three multiple stages.

In the present invention, by applying the photosensitive agent onto the surface of the gravure plate on which the uneven structure is formed, by an ink-jet printing method, it is possible to further add an uneven structure having a fine shape to the gravure plate. The respective horny cells have a configuration of from a polygonal shape through a circular shape having a major axis diameter of 30 to 40 μm. Therefore, for example, in the case where the size of the respective droplets applied by an ink-jet printing method is not less than 1 pL and not more than 33 pL, each dot printed has a size of not less than 15 μm and not more than 50 μm, so that it is possible to form concave portions of the uneven structure which have a size close to the size of the horny cell. From this viewpoint, the ink-jet printing method is suitable for production of a concavo-convex plate having an uneven structure imitating a surface configuration of the skin.

(Electrospinning Method)

In the electrospinning step, as the method of injecting the polymer compound A by an electrospinning method, there may be mentioned a resin solution-type electrospinning method (a) in which a resin solution prepared by dissolving the polymer compound A in a solvent is injected as an injection liquid, and a resin melt-type electrospinning method (b) in which a resin melt prepared by melting the polymer compound A is injected as an injection liquid.

Figure 4:
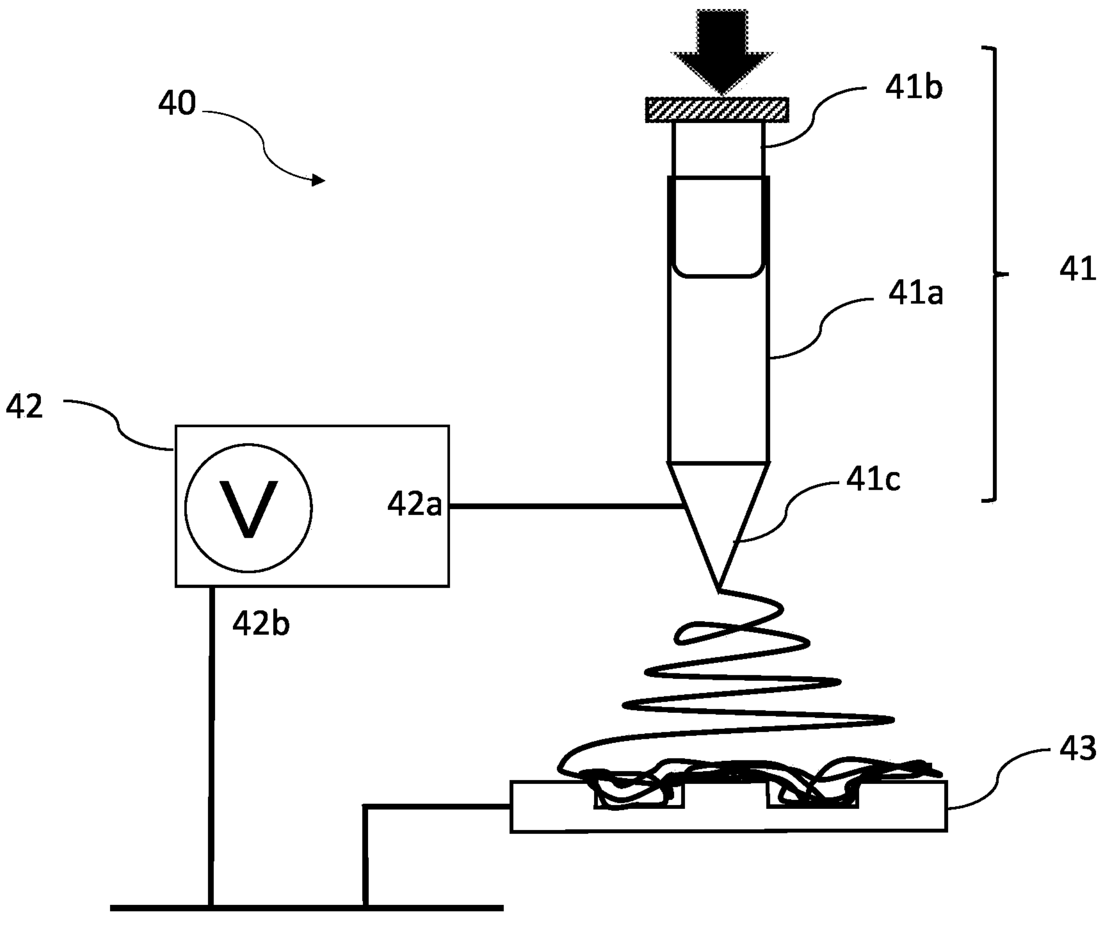
FIG. 4 is a schematic view showing one example of a resin solution-type electrospinning apparatus.

Referring to FIG. 4, there is shown a resin solution-type electrospinning apparatus 40 for implementing the resin solution-type electrospinning method (a). The resin solution-type electrospinning method (a) is implemented by using the apparatus 40 which includes a syringe 41, a high voltage supply 42 and a collector 43. The syringe 41 is equipped with a cylinder 41*a*, a plunger 41*b* and a capillary 41*c*. The capillary 41*c* has an inner diameter of about 10 to 1,000 μm.

The cylinder 41*a* is filled with an injection liquid that contains the polymer compound A as a raw material of the nanofibers and a solvent, if required together with the colorant. The details of the injection liquid are described hereinbelow. The high voltage supply 42 is, for example, a 10 to 30 kV direct voltage source. A positive electrode 42*a* of the high voltage supply 42 is electrically connected to the injection liquid in the syringe 41, with a negative electrode 42*b* of the high voltage supply 42 being grounded. The collector 43 is disposed such that its surface on which the nanofibers are deposited is formed into an uneven structure, and is grounded. The apparatus 40 shown in FIG. 4 may be operated in the atmosphere.

Meanwhile, although in the apparatus 40 shown in FIG. 4, the nanofibers formed therein are deposited on the collector 43 of a plate shape, a drum-shaped collector may also be used instead of the plate-shaped collector, in which the nanofibers may be deposited on a outer peripheral surface of a rotating drum thereof.

With a voltage applied between the syringe 41 and the collector 43, the plunger 41*b* of the syringe 41 is slowly forced into the cylinder to inject the injection liquid from the tip of the capillary 41*c*. The solvent in the thus injected liquid is allowed to vaporize, and the polymer compound A as a solute is formed into nanofibers and attracted onto the collector 43 while undergoing solidification, and further stretching and deformation, by the difference in electrical potential. In the case where the injection liquid contains the colorant, the colorant is partially incorporated into the polymer compound A in the course of its solidification. At this time, since the surface of the collector 43 has an uneven structure, it is possible to obtain the colored nonwoven fabric that also has a desired uneven shape on the surface thereof. From the principle of the production process, the nanofibers in the thus formed colored nonwoven fabric are respectively obtained as a continuous filament of infinite length.

Figure 5:
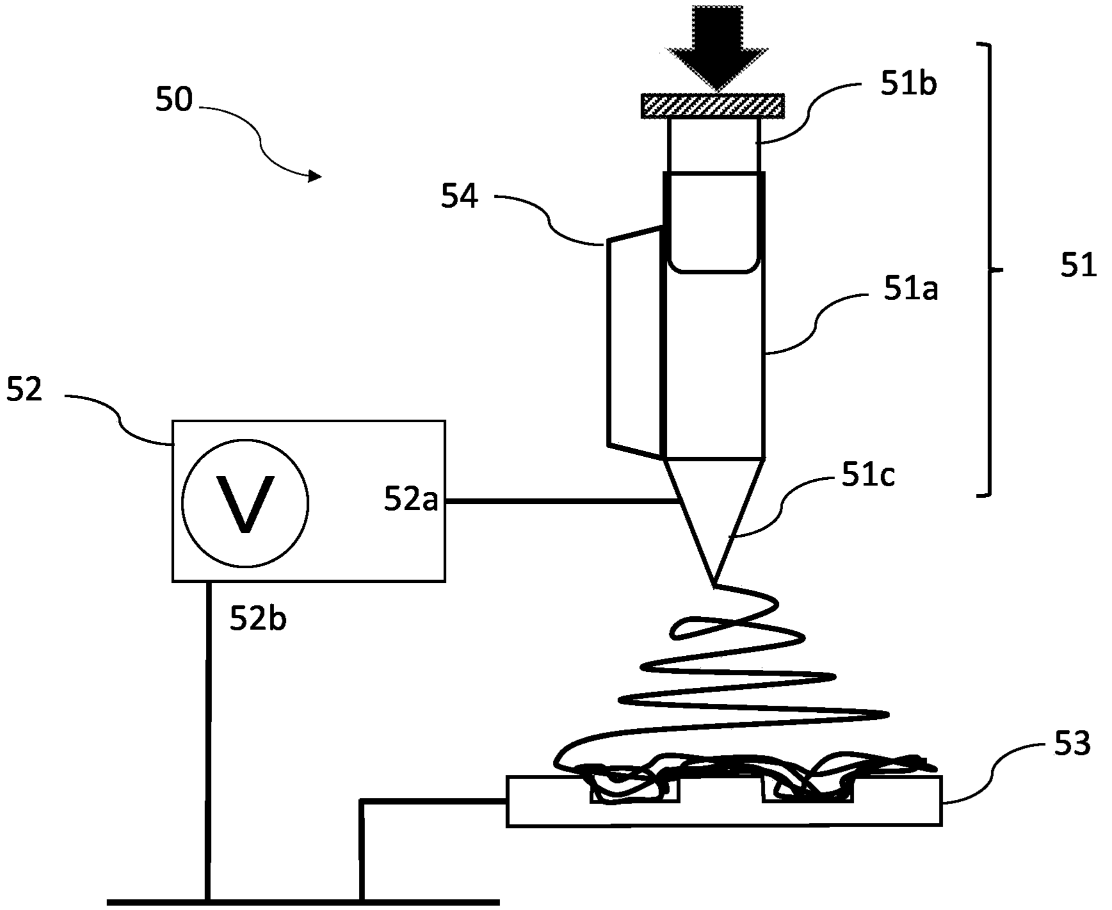
FIG. 5 is a schematic view showing one example of a resin melt-type electrospinning apparatus.

Referring to FIG. 5, there is shown a resin melt-type electrospinning apparatus 50 for implementing the resin melt-type electrospinning method (b). The resin melt-type electrospinning method (b) is implemented by using the apparatus 50 which includes a syringe 51, a high voltage supply 52, a collector 53 and a heater 54. The syringe 51 is equipped with a cylinder 51*a*, a plunger 51*b* and a capillary 51*c*. The capillary 51*c* has an inner diameter of about 10 to 1,000 μm. The cylinder 51*a* is filled with a solid resin that contains the polymer compound A as a raw material of the nanofibers, if required together with the colorant. The high voltage supply 52 is, for example, a 10 to 30 kV direct voltage source. A positive electrode 52*a* of the high voltage supply 52 is electrically connected to the solid resin in the syringe 51, with a negative electrode 52*b* of the high voltage supply 52 being grounded. The collector 53 is disposed such that its surface on which the nanofibers are deposited is formed into an uneven structure, and is grounded. The apparatus 50 shown in FIG. 5 may be operated in the atmosphere.

With a voltage applied between the syringe 51 and the collector 53, the aforementioned solid resin is heated by the heater 54, and melted in the syringe 51. The plunger 51*b* of the syringe 51 is then slowly forced into the cylinder to inject the molten resin as an injection liquid from the tip of the capillary 51*c*. The thus injected molten resin is cooled by release of heat therefrom, and the polymer compound A is formed into nanofibers and attracted onto the collector 53 while undergoing solidification, and further stretching and deformation by the difference in electrical potential. In the case where the solid resin contains the colorant, the solid resin containing the colorant is spun similarly to the nanofibers, and the colorant is partially incorporated into the polymer compound A. At this time, since the surface of the collector 53 has the uneven structure, it is possible to obtain the colored nonwoven fabric that also has a desired uneven shape on the surface thereof. From the principle of the production process, the nanofibers in the thus formed colored nonwoven fabric are respectively obtained as a continuous filament of infinite length.

Incidentally, as the method of incorporating the colorant into the solid resin, there may be used an ordinary method for dispersing a colorant in a thermoplastic resin by heating and kneading, and the like.

The voltage applied in the electrospinning method is preferably not less than 10 kV and more preferably not less than 15 kV, and is also preferably not more than 35 kV and more preferably not more than 30 kV.

The distance between the tip of the capillary of the syringe and the collector is preferably set to not less than 30 mm and more preferably not less than 50 mm, and is also preferably set to not more than 300 mm and more preferably not more than 200 mm.

The average amount of the injection liquid injected is preferably not less than 0.3 mL/min and more preferably not less than 0.7 mL/min, and is also preferably not more than 2 mL/min and more preferably not more than 1.5 mL/min.

The ambient environmental temperature upon injection of the injection liquid is preferably not lower than 20° C. and more preferably not lower than 25° C., and is also preferably not higher than 45° C. and more preferably not higher than 40° C.

In addition, the ambient environmental humidity upon injection of the injection liquid is preferably not less than 10% RH and more preferably not less than 15% RH, and is also preferably not more than 50% RH and more preferably not more than 45% RH.

[Pressure Filling Treatment]

When forming the nonwoven fabric by depositing the nanofibers on the surface of the collector by an electrospinning method, a pressure filling treatment may be conducted in the course of or subsequent to deposition of the nanofibers, from the viewpoint of efficiently filling the nanofibers deposited on the collector into the uneven structure of the collector.

The time of conducting the pressure filling treatment is not particularly limited as long as the treatment is conducted in the course of or subsequent to deposition of the nanofibers.

The pressure filling treatment is not necessarily required. However, from the same viewpoint as described above, it is preferable to conduct the pressure filling treatment at least one time. The number of times of conducting the pressure filling treatment is not particularly limited, and the pressure filling treatment may be conducted a plurality of times. From the viewpoint of enhancing productivity of the colored nonwoven fabric, the pressure filling treatment is preferably conducted one or more times.

The pressure filling treatment is preferably conducted by the method in which a pressure is uniformly applied to the surface of the nanofibers deposited on the collector using a roller, etc.

When the method of injecting the polymer compound A by an electrospinning method to form uncolored nanofibers and then coloring the nanofibers with the colorant is used in the process for producing the colored nonwoven fabric, the pressure filling treatment is preferably conducted after applying the colorant to the nanofibers.

(Coloring Method)

In the process for producing the colored nonwoven fabric according to the present invention, as the method of coloring the nanofibers with the colorant, there may be mentioned, for example, a method of injecting the polymer compound A and the colorant at the same time by an electrospinning method to form the colored nanofibers, and a method of injecting the polymer compound A by an electrospinning method to form uncolored nanofibers, and then coloring the uncolored nanofibers with the colorant. Among these methods, preferred is the method of injecting the polymer compound A and the colorant at the same time by an electrospinning method to form the colored nanofibers (hereinafter also referred to as a "method (i-1)"), or the method of injecting the polymer compound A by an electrospinning method to form uncolored nanofibers, and then coloring the uncolored nanofibers with the colorant (hereinafter also referred to as a "method (i-2)").

(Method (i-1))

In the case of using the method (i-1), the production process of the present invention preferably includes the following step 1-1:

Step 1-1: injecting the polymer compound A and the colorant at the same time by an electrospinning method to deposit colorant-containing nanofibers on the surface of the collector, thereby obtaining the colored nonwoven fabric.

[Step 1-1]

In the step 1-1, as the method of injecting the polymer compound A and the colorant at the same time, preferred is the method of injecting the polymer compound A and the colorant commonly from the same capillary.

In the case where the electrospinning method used in the step 1-1 is the resin solution-type electrospinning method (a), there is used an injection liquid containing the polymer compound A and the colorant. In this case, the content of the colorant based on the content of the polymer compound A in the injection liquid as calculated in terms of a ratio thereof assuming that the content of the polymer compound A in the injection liquid is regarded as being 100% by mass, is preferably not less than 30% by mass, more preferably not less than 35% by mass, even more preferably not less than 40% by mass and further even more preferably not less than 50% by mass, and is also preferably not more than 110% by mass, more preferably not more than 100% by mass, even more preferably not more than 95% by mass and further even more preferably not more than 90% by mass. That is, the content of the colorant based on the content of the polymer compound A in the injection liquid as calculated on the basis of 100 parts by mass of the content of the polymer compound A in the injection liquid is preferably not less than 30 parts by mass, more preferably not less than 35 parts by mass, even more preferably not less than 40 parts by mass and further even more preferably not less than 50 parts by mass, and is also preferably not more than 110 parts by mass, more preferably not more than 100 parts by mass, even more preferably not more than 95 parts by mass and further even more preferably not more than 90 parts by mass.

The content of the polymer compound A in the injection liquid is preferably not less than 2% by mass, more preferably not less than 3% by mass and even more preferably not less than 4% by mass, and is also preferably not more than 20% by mass, more preferably not more than 15% by mass and even more preferably not more than 10% by mass.

In the present specification, when using two or more kinds of colorants, the content of the colorant as used herein means a total content of the two or more kinds of colorants, and when using two or more kinds of polymer compounds as the polymer compound A, the content of the polymer compound A as used herein means a total content of the two or more kinds of polymer compounds.

In the case of using the injection liquid containing the polymer compound A and the colorant, from the viewpoint of suppressing precipitation or aggregation of the colorant particles when using the aforementioned colorant particles as the colorant to attain a desired color development effect, and from the viewpoint of suppressing recrystallization and deposition of dyes in the solvent when using the dyes as the colorant to attain a desired color development effect, as well as from the viewpoint of suppressing clogging of flow paths with the liquid in the electrospinning apparatus, it is preferred that a solution or dispersion containing the colorant is prepared separately from the resin solution containing the polymer compound A, and the thus prepared solution or dispersion containing the colorant is mixed with the resin solution containing the polymer compound A before using them in the electrospinning method to thereby prepare the injection liquid. Since the thus prepared injection liquid is improved in dispersibility of the colorant therein, the nanofibers formed tend to be uniformly colored, and the injection liquid tends to hardly cause clogging of the capillary.

[Preparation of Solution or Dispersion Containing Colorant]

The solution or dispersion containing the colorant which is prepared separately from the solution containing the polymer compound A can be obtained by dissolving or dispersing the colorant in a liquid medium. The liquid medium may be appropriately selected and used according to the kind of colorant used. Among them, a volatile liquid medium that can exhibit volatility at a normal temperature (25° C.) under 1 atm is preferably used as the liquid medium. When using such a volatile liquid medium, it is possible to easily remove the liquid medium upon production of the nanofibers by an electrospinning method. From this viewpoint, water or an organic solvent is preferably used as the liquid medium. Examples of the organic solvent include acetone, isoparaffin (light liquid isoparaffin), ethanol, and silicone compounds, such as cyclomethicones, e.g., octamethylcyclotetrasiloxane, decamethylcyclopentasiloxane, etc., dimethicones, e.g., octamethyltrisiloxane, dodecamethylpentasiloxane, etc., methyltrimethicone, etc., and the like. Of these organic solvents, the silicone compounds may be used from the viewpoint of ensuring safety to the skin.

The content of the colorant in the solution or dispersion containing the colorant is preferably not less than 3% by mass, more preferably not less than 5% by mass and even more preferably not less than 10% by mass, and is also preferably not more than 50% by mass, more preferably not more than 40% by mass, even more preferably not more than 30% by mass and further even more preferably not more than 20% by mass, from the viewpoint of satisfying both of the coloring effect for the colored nonwoven fabric and uniformity of the coloration.

When the content of the colorant in the solution or dispersion containing the colorant is controlled to not less than 3% by mass, a sufficient coloring effect for the colored nonwoven fabric can be attained, whereas when the content of the colorant in the solution or dispersion containing the colorant is controlled to not more than 50% by mass, dispersibility of the pigment and solubility of the dyes in the solution or dispersion can be improved, so that it is possible to effectively prevent deterioration in quality of the colored nonwoven fabric owing to aggregation of the pigment particles and deposition of the dyes, etc.

The colorant may be crushed into a predetermined size before preparing the solution or dispersion to control a particle size thereof, or may be dissolved therein in a molecular state.

The solution or dispersion containing the colorant may also contain, in addition to the colorant, a dispersant for enhancing dispersibility of the colorant or a defoaming agent for preventing the solution or dispersion from foaming.

Various kinds of surfactants may be used as the dispersant. Among these surfactants, an anionic surfactant and a nonionic surfactant are preferably used.

Examples of the anionic surfactant include fatty acid metal salts, alkylsulfates, alkylethersulfates, alkylphosphates, alkyletherphosphates and the like. Specific examples of the anionic surfactant include sodium laurylsulfate, sodium polyoxyethylene laurylethersulfate, sodium polyoxyethylene lauryletherphosphate, sodium polyoxyethylene oleyletherphosphate, and the like.

Examples of the nonionic surfactant include polyoxyethylene alkyl ethers, glycerol fatty acid esters, propylene glycol fatty acid esters, fatty acid sorbitan esters, sucrose fatty acid esters, fatty acid mono(di)ethanolamides, polyethylene glycol fatty acid esters, fatty acid polyoxyethylene sorbitol esters, polyoxyethylene hardened castor oil, and the like. Specific examples of the nonionic surfactant include polyoxyethylene octyl dodecyl ether, glycerol monostearate, sorbitan sesquioleate, sucrose fatty acid esters, coconut oil fatty acid diethanolamide, polyethylene glycol monostearate, polyethylene glycol monooleate, polyoxyethylene lauryl ether, polyoxyethylene stearyl ether, polyoxyethylene oleyl ether, polyoxyethylene glycerol monostearate, polyoxyethylene sorbitan monostearate, polyoxyethylene sorbitol tetraoleate, polyoxyethylene hardened castor oil, and the like.

These surfactants may be used alone or in combination of any two or more thereof.

In the case where the solution or dispersion containing the colorant contains the dispersant, the content of the dispersant in the solution or dispersion containing the colorant is preferably not less than 0.1% by mass and more preferably not less than 1% by mass, and is also preferably not more than 10% by mass and more preferably not more than 6% by mass, from the viewpoint of fully enhancing dispersibility of the colorant.

When using the two or more kinds of surfactants in combination with each other as the dispersant, the total content of the surfactants in the solution or dispersion is preferably controlled to the aforementioned range.

The defoaming agent is preferably a silicone-based defoaming agent. Examples of the silicone-based defoaming include dimethylsilicone oil, silicone oil compounds, silicone emulsions, polyether-modified polysiloxane, and fluorosilicone oils.

In the case where the solution or dispersion containing the colorant contains the defoaming agent, the content of the defoaming agent in the solution or dispersion containing the colorant is preferably not less than 0.01% by mass and more preferably not less than 0.1% by mass, and is also preferably not more than 2% by mass, more preferably not more than 1.5% by mass and even more preferably not more than 0.5% by mass, from the viewpoint of suppressing foaming of the solution or dispersion.

Upon preparation of the dispersion containing the colorant, the aforementioned respective components may be mixed with a liquid medium, such as water or an organic solvent, etc., and dispersed in the liquid medium using a disperser while deaggregating the colorant. Examples of the disperser include media mills, such as a ball mill, a bead mill, etc.; and a disper.

As the solution or dispersion containing the colorant, two or more solutions or dispersions which are different in composition from each other may be previously prepared, and such two or more solutions or dispersions may be used at an appropriate mixing ratio according to the aimed color of the colored nonwoven fabric. For example, one of the two or more solutions or dispersions containing the colorant may be prepared in the form of a solution or dispersion that contains only a white pigment (hereinafter also referred to as a "white solution or dispersion"), and the remaining solution(s) or dispersion(s) may be prepared in the form of a solution or dispersion that contains one or more pigments other than the white pigment (hereinafter also referred to as a "non-white solution or dispersion"). From the viewpoint of attaining higher freedom of color matching, it is preferred to prepare the injection liquid for electrospinning by mixing the white solution or dispersion and the one or more non-white solutions or dispersions with the resin solution containing the polymer compound A. For instance, in the case where such a colored nonwoven fabric as colored in skin tone is to be produced, it is preferred that the white solution or dispersion is used in combination with the non-white solution or dispersion.

In addition, in the case where the colorant particles are used in the form of colorant-containing polymer particles, it is preferred that the colorant water dispersion used in the below-mentioned water-based ink for ink-jet printing is used as the dispersion containing the colorant which is used for preparing the injection liquid.

[Preparation of Solution Containing Polymer Compound A]

The solution containing the polymer compound A which is used in combination with the solution or dispersion containing the colorant is appropriately selected and used according to the kind of polymer compound A or the kind of solution or dispersion containing the colorant. For example, in the case where the solution or dispersion containing the colorant is in the form of an aqueous solution or water dispersion containing water as a main medium, the solution containing the polymer compound A is also preferably in the form of either an aqueous solution or a water-soluble organic solvent solution from the viewpoint of attaining good compatibility therebetween. From the same viewpoint as described above, in the case where the solution or dispersion containing the colorant is a solution or dispersion containing an organic solvent as a main medium, the solution containing the polymer compound A is preferably in the form of an organic solvent solution that is compatible with the organic solvent.

In the case where the solution containing the polymer compound A contains, for example, a water-insoluble polymer compound as the polymer compound A and water as a medium for the water-insoluble polymer compound, it is possible to use a water-soluble polymer compound that can be rendered water-insoluble by subjecting it to water-insolubilizing treatment after forming the nanofibers, in combination therewith. The use of water as the medium is especially advantageous when producing the nanofibers containing the water-soluble polymer compound in addition to the water-insoluble polymer compound.

For example, in the case of using the aforementioned polyvinyl alcohol or alkali-soluble cellulose, by depositing the nanofibers on the surface of the collector by an electrospinning method and then subjecting the resulting colored nonwoven fabric to water-insolubilizing treatment in which the colored nonwoven fabric is heated, rinsed with water or dried to remove a neutralizing agent therefrom, it is possible to obtain the colored nonwoven fabric that contains the nanofibers containing a water-insoluble polymer compound formed of the polyvinyl alcohol or alkali-soluble cellulose.

The preferred heating conditions for the water-insolubilizing treatment include a heating temperature of 20 to 200° C. and a heating time of 1 to 200 minutes.

In the case of using the water-soluble polymer compound that can be rendered water-insoluble after deposition or formation of the nanofibers, there may also be used a mixed solution prepared by dispersing and dissolving the water-soluble polymer compound that can be subsequently rendered water-insoluble and another water-soluble polymer compound commonly in the same solvent. In this case, as the solvent, there may be used water as described above. In addition, a mixed solvent containing water and a water-soluble organic solvent may also be used in place of the water.

As the other example of the solution containing the polymer compound A, there may be mentioned a solution that contains a water-soluble polymer compound and a water-insoluble polymer compound that can be dissolved in an organic solvent compatible with water, and a mixed solvent containing water and the organic solvent. Examples of the combination of the water-insoluble polymer compound and the organic solvent which may be used in the solution include a combination of an oxazoline-modified silicone with ethanol or methanol, and a combination of a zein with ethanol or acetone.

As the still other example of the solution containing the polymer compound A, there may be mentioned a solution prepared by dissolving a water-soluble polymer compound that can be dissolved in water and an organic solvent and a water-insoluble polymer compound that can be dissolved in the organic solvent, in the organic solvent. Examples of the combination of the water-soluble polymer compound and the water-insoluble polymer compound which can be used in the solution include a combination of hydroxypropyl cellulose with polyvinyl butyral.

Even though the solution containing the polymer compound A is any type of the aforementioned solutions, the content of the polymer compound A in the solution (in the case where two or more kinds of polymer compounds are used as the polymer compound A, it means a total content of the two or more polymer compounds as described above) may vary depending upon the saturation solubility of the resin used, and is preferably not less than 3% by mass, more preferably not less than 5% by mass and even more preferably not less than 10% by mass, and is also preferably not more than 35% by mass, more preferably not more than 25% by mass and even more preferably not more than 20% by mass.

When the solution containing the polymer compound A and the solution or dispersion containing the colorant are mixed with each other to prepare the injection liquid for electrospinning, in the case where the content of the polymer compound A in the solution containing the polymer compound A and the content of the colorant in the solution or dispersion containing the colorant respectively fall within the aforementioned ranges, the content of the solution containing the polymer compound A in the whole amount of the injection liquid is preferably not less than 40% by mass, more preferably not less than 50% by mass and even more preferably not less than 55% by mass, and is also preferably not more than 95% by mass, more preferably not more than 93% by mass and even more preferably not more than 90% by mass.

(Method (i-2))

In the case where the method (i-2) of injecting the polymer compound A by an electrospinning method to form uncolored nanofibers and then coloring the uncolored nanofibers with the colorant is used as the method for coloring the nanofibers, examples of the method of applying the colorant to the nanofibers include an ink-jet printing method; and an analog printing method, such as gravure printing, flexographic printing, offset printing, screen printing, etc. Of these printing methods, from the viewpoint of improving a sense of unity with the skin in appearance, a gloss feel and a transparent feel of the resulting colored nonwoven fabric by the coloration, preferred is an ink-jet printing method.

In the ink-jet printing method, droplets containing the colorant (ink) are directly applied onto a material to be printed while keeping a printing apparatus, etc., in non-contact with the material. Therefore, the ink-jet printing method is capable of applying the colorant to the preliminarily prepared uncolored nonwoven fabric without any physical damage thereto to thereby enable production of the colored nonwoven fabric.

In addition, since the amount of the colorant applied can be controlled independently of the amount of the polymer compound A injected, it is possible to broaden a color region of the coloration which can be achieved by the colored nonwoven fabric. Furthermore, since the colorant having a different solubility from that of the polymer compound A can be used in the ink-jet printing method, it is possible to increase the degree of freedom of designing of the colorant and facilitate control of storage stability of the injection liquid.

As the method of applying the ink-jet printing method to the aforementioned coloration, there may be mentioned the method of applying an ink containing the colorant to the preliminarily prepared uncolored nonwoven fabric by an ink-jet printing method, and the method of preliminarily applying an ink containing the colorant onto the uneven structure of the collector by an ink-jet printing method, and then depositing the uncolored nanofibers on the uneven structure-bearing surface of the collector to which the colorant has been applied.

In the case where the preliminarily prepared uncolored nonwoven fabric is subjected to ink-jet printing, the ink applied thereto is retained in a void layer of the nonwoven fabric which is formed by the nanofibers in the nonwoven fabric, by a capillary attraction force. For this reason, the ink has a dot shape close to a true circle, and therefore can also be prevented from suffering from occurrence of intercolor bleeding(color mixture). In this case, the image quality of the resulting colored nonwoven fabric is similar to that of an analog printed material, so that a contour of the colored nonwoven fabric attached is obscured mildly, whereby it is possible to improve a sense of unity with the skin in appearance, a gloss feel and a transparent feel of the resulting colored nonwoven fabric, and obtain makeup images capable of imparting gentle impression.

On the other hand, in the method of preliminarily applying the colorant to the uneven structure of the collector by an ink-jet printing method and then depositing the uncolored nanofibers on the uneven structure-bearing surface of the collector to which the colorant has been applied, since the ink is preliminarily filled in the concavo-convex portions of the surface of the collector, it is possible to form an image pattern that can be hardly designed by an ordinary ink-jet printing method, such as those image patterns having not only a true circle shape, but also a square shape, a triangular shape, a honeycomb shape constituted of continuously arranged hexagonal shapes, etc., on the colored nonwoven fabric. In this case, the resulting colored nonwoven fabric has such an image quality as being capable of providing makeup images imparting an intellectual virtual reality-like impression whose contour is sharply accentuated like those obtained by a line-drawing digital device, such as a display, etc.

In the case of using the method (i-2) in the production process of the present invention, from the viewpoint of improving a sense of unity with the skin in appearance, a gloss feel and a transparent feel of the resulting colored nonwoven fabric, the production process of the present invention preferably includes the following step 2-1 and step 2-2.

Step 2-1: injecting the polymer compound A by an electrospinning method to deposit the nanofibers on the surface of the collector, thereby obtaining an uncolored nonwoven fabric; and Step 2-2: applying the colorant to the uncolored nonwoven fabric obtained in the step 2-1 by an ink-jet printing method to obtain the colored nonwoven fabric.

[Step 2-1]

In the electrospinning method of the step 2-1, there may be used any of the aforementioned resin solution-type electrospinning apparatus and resin melt-type electrospinning apparatus.

In the case of using the resin solution-type electrospinning apparatus, it is preferred that when injecting the polymer compound A, the aforementioned solution containing the polymer compound A is used as the injection liquid containing the polymer compound A.

The content of the polymer compound A in the injection liquid used in the step 2-1 (in the case where two or more kinds of polymer compounds are used as the polymer compound A, it means a total content of the two or more polymer compounds as described previously) may vary depending upon the saturation solubility of the resin used, and is preferably not less than 2% by mass, more preferably not less than 3% by mass and even more preferably not less than 4% by mass, and is also preferably not more than 20% by mass, more preferably not more than 15% by mass and even more preferably not more than 10% by mass.

[Step 2-2]

The colorant used in the ink-jet printing method of the step 2-2 is preferably used in the form of a water-based ink whose viscosity is controlled so as to render raw materials used for ordinary cosmetics ejectable by ink-jetting, for example, may be controlled to not more than 20 mPa·s. The term "water-based" as used herein means that water has a largest content among components of a medium contained in the water-based ink.

When applying the colorant by the ink-jet printing method, the components other than the colorant may be respectively applied in a necessary amount to a necessary position. The application of the other components is also preferably used in the case where functional chemicals are driven into the void layer of the colored nonwoven fabric to retain the chemicals therein or in the case where the nanofibers are dissolved or swelled to control the shape or thickness of the nanofibers in the colored nonwoven fabric.

The method of ejecting the ink which can be used in the ink-jet printing method is not particularly limited, and may be any of an electro-mechanical conversion method such as a piezoelectric method, etc., an electro-thermal conversion method, such as a thermal method, etc., and the like.

In addition, in the ink-jet printing method, since printing can be carried out without contact with a material to be printed, a print pattern can be formed on the nonwoven fabric irrespective of the uneven shape of the nonwoven fabric. For this reason, the uneven shape of the nonwoven fabric may be formed into a print pattern that can be emphasized by illusion.

More specifically, when forming a skin texture structure on the nonwoven fabric, assuming that light is irradiated from above, the L* value of an upper half side of a print image of the skin texture structure is increased (becomes lighter), whereas the L* value of a lower half side of the print image of the skin texture structure is lowered (becomes darker), whereby it is possible to obtain a colored nonwoven fabric whose uneven shape in appearance is more emphasized as compared to the uneven shape inherent to the colored nonwoven fabric.

Moreover, by utilizing such an illusion technology, it is possible to produce a three-dimensional feel of a whole portion of the face. For example, the person whose lip projects forwardly of the forehead is emphasized in the lip to impart a more passionate impression to the face, whereas the person whose lip does not project forwardly of the forehead is not emphasized so much in the lip to impart a rational impression rather than a passionate impression to the face. For this reason, by further applying an ink to respective portions of the colored nonwoven fabric attached to the forehead portion and the jaw portion by an ink-jet printing method to adjust the respective coloration degrees thereof, the resulting colored nonwoven fabric is emphasized in depth feel, and can be therefore used as a makeup cosmetic coating having a three-dimensional feel.

[Water-Based Ink for Ink-Jet Printing]

The water-based ink for ink-jet printing contains a pigment water dispersion, a dye aqueous solution, or a colorant water dispersion prepared by dispersing a colorant, such as a pigment or a dye, with a water-dispersive polymer, and may be produced by adding an organic solvent, water and various additives thereto.

The term "water-dispersive polymer" as used in the present specification means a polymer with which the colorant can be dispersed in a water-based medium. From the viewpoint of improving dispersibility of the colorant, the water-dispersive polymer used in the ink is preferably an ionic group-containing polymer, more preferably an anionic group-containing anionic polymer and a cationic group-containing cationic polymer. Examples of the anionic group-containing anionic polymer and the cationic group-containing cationic polymer include the same polymers as illustrated above as to the dispersive polymer.

The content of the colorant in the water-based ink is preferably not less than 1% by mass, more preferably not less than 2% by mass, even more preferably not less than 3% by mass and further even more preferably not less than 4% by mass, and is also preferably not more than 20% by mass, more preferably not more than 15% by mass, even more preferably not more than 10% by mass and further even more preferably not more than 8% by mass, from the viewpoint of improving storage stability and ejection durability of the water-based ink as well as from the viewpoint of enhancing optical density of the ink on the colored nonwoven fabric upon printing.

The content of water in the water-based ink is preferably not less than 50% by mass, more preferably not less than 60% by mass and even more preferably not less than 75% by mass, and is also preferably not more than 95% by mass, more preferably not more than 94% by mass and even more preferably not more than 93% by mass, from the viewpoint of improving storage stability and ejection durability of the water-based ink.

The static surface tension of the water-based ink as measured at 20° C. is preferably not less than 25 mN/m, more preferably not less than 30 mN/m and even more preferably not less than 32 mN/m, and is also preferably not more than 45 mN/m, more preferably not more than 40 mN/m and even more preferably not more than 38 mN/m, from the viewpoint of improving ejection durability of the water-based ink.

The viscosity of the water-based ink as measured at 35° C. is preferably not less than 1 mPa·s, more preferably not less than 1.5 mPa·s and even more preferably not less than 2 mPa·s, and is also preferably not more than 10 mPa·s, more preferably not more than 7 mPa·s and even more preferably not more than 4 mPa·s, from the viewpoint of improving ejection durability of the water-based ink.

The static surface tension of the water-based ink as measured at 20° C. and the viscosity of the water-based ink as measured at 35° C. may be measured by the respective methods described in Examples below.

The aforementioned water-based ink may also contain various additives that are usually used in water-based inks from the viewpoint of controlling physical properties of the ink. Examples of the additives include a wetting agent, a penetrant, a dispersant, such as a surfactant, etc., a viscosity controller, such as hydroxypropyl cellulose, hydroxyethyl cellulose, polyvinyl alcohol, etc., a defoaming agent, such as a silicone oil, etc., a mildew-proof agent, a rust preventive, and the like.

Examples of the wetting agent and the penetrant include polyhydric alcohols and ethers or acetates of the polyhydric alcohols, such as ethylene glycol, propylene glycol (1,2-propanediol), 1,2-hexanediol, diethylene glycol, triethylene glycol, polyethylene glycol, glycerin, trimethylol propane, diethylene glycol diethyl ether, etc. Of these wetting agents and penetrants, preferred are propylene glycol (1,2-propanediol), 1,2-hexanediol, polyethylene glycol, glycerin, triethylene glycol and trimethylol propane.

In addition, the polyhydric alcohols may also be used in the form of an alkyleneoxide adduct thereof. Examples of the preferred alkyleneoxide adduct of the polyhydric alcohols include a glycerin-modified ethyleneoxide adduct.

Examples of the surfactant include a nonionic surfactant, such as an ethyleneoxide adduct of acetylenediol, a polyoxyethylene alkyl ether, etc., and the like.

The volume-average particle size of the colorant particles in the aforementioned water-based ink in the case of using a non-white colorant is preferably not less than 30 nm, more preferably not less than 50 nm and even more preferably not less than 60 nm, and is also preferably not more than 250 nm, more preferably not more than 200 nm and even more preferably not more than 180 nm, from the viewpoint of suppressing clogging of nozzles to thereby improve ejection durability of the ink as well as from the viewpoint of improving dispersion stability of the colorant particles.

The volume-average particle size of the colorant particles in the aforementioned water-based ink in the case of using a white colorant is preferably not less than 150 nm, more preferably not less than 240 nm and even more preferably not less than 290 nm, and is also preferably not more than 1,000 nm, more preferably not more than 500 nm, even more preferably not more than 350 nm and further even more preferably not more than 330 nm, from the same viewpoint as described above.

The volume-average particle size of the colorant particles in the water-based ink may be measured by the method described in Examples below.

[Production of Colorant Water Dispersion]

The aforementioned colorant water dispersion may be produced by the method of dispersing the colorant particles in water. In the case where the colorant dispersed with the water-dispersive polymer is used as the colorant particles, the process for producing the colorant water dispersion preferably includes the following step I and step II, though it is not necessarily limited thereto.

Step I: subjecting a colorant mixture containing water, the colorant, the water-dispersive polymer and an organic solvent to dispersion treatment to obtain a colorant dispersion liquid; and Step II: removing the organic solvent from the colorant dispersion liquid obtained in the step I to obtain the colorant water dispersion.

[Step I]

The step I is the step of subjecting a colorant mixture containing water, the colorant, the water-dispersive polymer and an organic solvent to dispersion treatment to obtain a colorant dispersion liquid.

The content of the water-dispersive polymer in the colorant mixture is preferably not less than 1% by mass, more preferably not less than 3% by mass and even more preferably not less than 5% by mass, and is also preferably not more than 15% by mass, more preferably not more than 12% by mass and even more preferably not more than 10% by mass, from the viewpoint of improving dispersion stability of the colorant water dispersion and storage stability and ejection durability of the resulting water-based ink.

The mass ratio of the content of the colorant to the content of the water-dispersive polymer [colorant/water-dispersive polymer] in the colorant mixture is preferably not less than 1, more preferably not less than 1.5 and even more preferably not less than 2, and is also preferably not more than 4, more preferably not more than 3.5 and even more preferably not more than 3, from the viewpoint of improving dispersion stability of the colorant water dispersion and storage stability and ejection durability of the resulting water-based ink.

The organic solvent used in the step I preferably has high affinity to the water-dispersive polymer and good wettability to the colorant. As the organic solvent, preferred are organic solvents having 2 to 8 carbon atoms, such as aliphatic alcohols, ketones, ethers, esters and the like. Examples of the aliphatic alcohols include n-butanol, tertiary butanol, isobutanol, diacetone alcohol, and the like. Examples of the ketones include methyl ethyl ketone, diethyl ketone, methyl isobutyl ketone, and the like. Examples of the ethers include dibutyl ether, tetrahydrofuran, dioxane, and the like. Of these organic solvents, from the viewpoint of improving wettability to the colorant and adsorptivity of the water-dispersive polymer upon the coloration as well as from the viewpoint of improving safety problems owing to the residual organic solvent when attached to the skin, preferred are ethanol and isopropanol, and more preferred is ethanol.

The content of the organic solvent in the colorant mixture is preferably not less than 10% by mass, more preferably not less than 20% by mass and even more preferably not less than 25% by mass, and is also preferably not more than 50% by mass, more preferably not more than 45% by mass and even more preferably not more than 40% by mass, from the viewpoint of improving wettability of the colorant and adsorptivity of the water-dispersive polymer to the colorant. Meanwhile, in the case where two or more organic solvents are contained in the colorant mixture, the total amount of the two or more organic solvents is calculated as the amount of the aforementioned organic solvent, and it is hereinafter defined in the same way.

The mass ratio of the content of the water-dispersive polymer to the content of the organic solvent [water-dispersive polymer/organic solvent] in the colorant mixture is preferably not less than 0.10, more preferably not less than 0.15 and even more preferably not less than 0.20, and is also preferably not more than 0.60, more preferably not more than 0.50 and even more preferably not more than 0.40, from the viewpoint of improving wettability of the colorant and adsorptivity of the polymer to the colorant.

The total content of water and the organic solvent in the colorant mixture is preferably not less than 50% by mass, more preferably not less than 55% by mass and even more preferably not less than 60% by mass, and is also preferably not more than 85% by mass, more preferably not more than 80% by mass and even more preferably not more than 75% by mass, from the viewpoint of improving dispersion stability of the colorant water dispersion as well as from the viewpoint of enhancing productivity of the colorant water dispersion.

The mass ratio of the content of the organic solvent to the content of water [organic solvent/water] in the colorant mixture is preferably not less than 0.20, more preferably not less than 0.40 and even more preferably not less than 0.60, and is also preferably not more than 1, more preferably not more than 0.90 and even more preferably not more than 0.80, from the viewpoint of controlling wettability of the colorant to thereby accelerate dispersion of the colorant as well as from the viewpoint of improving adsorptivity of the water-dispersive polymer to the colorant.

In the case where the ionic group-containing polymer is used as the water-dispersive polymer, from the viewpoint of improving dispersion stability of the colorant water dispersion as well as storage stability and ejection durability of the resulting water-based ink, the ionic groups contained in the water-dispersive polymer are preferably neutralized in the step I using a neutralizing agent. When using the neutralizing agent, the ionic groups contained in the water-dispersive polymer are neutralized such that the pH value of the resulting colorant water dispersion preferably falls within the range of from 7 to 11.

In the case where the ionic groups contained in the water-dispersive polymer are anionic groups, examples of the neutralizing agent include hydroxides of alkali metals; volatile bases, such as ammonia, etc.; and organic amines, such as methylamine, dimethylamine, trimethylamine, ethylamine, diethylamine, triethylamine, triethanolamine, tributylamine, etc. Of these neutralizing agents, from the viewpoint of improving dispersion stability of the colorant water dispersion as well as storage stability and ejection durability of the resulting water-based ink, preferred are hydroxides of alkali metals and volatile bases, and more preferred are hydroxides of alkali metals. As the hydroxides of alkali metals, preferred is sodium hydroxide.

The neutralizing agent is preferably used in the form of an aqueous neutralizing agent solution from the viewpoint of sufficiently accelerating the neutralization. These neutralizing agents may be used alone or in the form of a mixture of any two or more thereof.

In the case where a hydrophobic pigment, such as a hydrophobized titanium oxide, hydrophobized zinc oxide, etc., is used as the colorant, it is preferred that the step I preferably includes the following steps I-1 and I-2 in which a cationic silicone polymer and an anionic polymer are used in combination with each other as the water-dispersive polymer.

Step I-1: suspending the hydrophobized hydrophobic pigment using the cationic silicone polymer to obtain a suspension of the hydrophobic pigment; and Step I-2: adding the anionic polymer to the suspension of the hydrophobic pigment obtained in the step I-1 to obtain a colorant mixture, and then subjecting the colorant mixture to dispersion treatment to obtain a colorant dispersion liquid.

By conducting the step I-1, a hydrophobic silicone moiety of the cationic silicone polymer is adsorbed onto the surface of the hydrophobic pigment, whereas a hydrophilic cationic moiety of the cationic silicone polymer is oriented to the side of the medium, so that the colorant particles can be suspended in such a stable state that they possess a positive zeta potential.

Then, by adding the anionic polymer in the step I-2, the anionic polymer is adsorbed onto the cationic groups of the cationic silicone polymer adsorbed onto the hydrophobic pigment to thereby disperse the colorant particles in such a state that they possess a negative zeta potential, whereby it is possible to obtain a stable dispersion even when using the hydrophobic pigment.

In the case where the non-white colorant is used in the step I, the volume-average particle size of the colorant particles in the colorant dispersion liquid obtained after the dispersion treatment is preferably not less than 30 nm, more preferably not less than 50 nm and even more preferably not less than 60 nm, and is also preferably not more than 250 nm, more preferably not more than 200 nm and even more preferably not more than 180 nm.

In the case where the white colorant is used in the step I, the volume-average particle size of the colorant particles in the colorant dispersion liquid obtained after the dispersion treatment is preferably not less than 150 nm, more preferably not less than 240 nm and even more preferably not less than 290 nm, and is also preferably not more than 1,000 nm, more preferably not more than 500 nm, even more preferably not more than 350 nm and further even more preferably not more than 330 nm, from the viewpoint of improving dispersion stability of the white colorant (for example, such as titanium oxide), suppressing foaming of the dispersion liquid and improving defoaming properties thereof.

The volume-average particle size of the colorant particles in the colorant dispersion liquid may be measured by the method described in Examples below.

The colorant particles may be atomized into fine particles having a desired volume-average particle size only by a substantial dispersion treatment by applying a shear stress thereto. However, it is preferred that the colorant mixture is first subjected to a preliminary dispersion treatment, and then further to the substantial dispersion treatment so as to control the volume-average particle size of the obtained colorant particles to a desired value.

In the preliminary dispersion treatment, there may be used ordinary mixing or stirring devices, such as an anchor blade, a disper blade, etc. Of these devices, preferred are high-speed stirring mixers, such as "Ultra Disper" (tradename) available from Asada Iron Works Co., Ltd., "Ebara Milder" (tradename) available from Ebara Corporation, "TK Homomixer" (tradename) and "TK ROBOMIX" (tradename) both available from Primix Co., Ltd., and the like.

As a means for applying a shear stress in the substantial dispersion treatment, there may be used, for example, kneading machines, such as roll mills, kneaders, extruders, etc., high-pressure homogenizers, such as "MICROFLUIDIZER" (tradename) available from Microfluidics Corporation, etc., and media-type dispersers, such as paint shakers, beads mills, etc. Examples of the commercially available media-type dispersers include "Ultra Apex Mill" (tradename) available from Kotobuki Industries Co., Ltd., "Pico Mill" (tradename) available from Asada Iron Works Co., Ltd., and the like. These devices may be used in combination of any two or more thereof. Among these devices, the high-pressure homogenizers are preferably used from the viewpoint of reducing a particle size of the colorant.

In the case where the substantial dispersion treatment is conducted using the high-pressure homogenizer, the particle size of the colorant can be adjusted to a desired value by controlling the treating pressure and the number of passes through the homogenizer in the dispersion treatment.

The treating pressure used in the substantial dispersion treatment is preferably not less than 60 MPa, more preferably not less than 100 MPa and even more preferably not less than 150 MPa, and is also preferably not more than 250 MPa, more preferably not more than 200 MPa and even more preferably not more than 180 MPa.

Also, the number of passes through the homogenizer used in the dispersion treatment is preferably not less than 3, more preferably not less than 10 and even more preferably not less than 15, and is also preferably not more than 30, more preferably not more than 25 and even more preferably not more than 20.

[Step II]

The step II is the step of removing the organic solvent from the colorant dispersion liquid obtained in the step I, thereby obtaining the colorant water dispersion.

In the step II, the mass ratio of the content of the organic solvent to the content of water [organic solvent/water] in the colorant dispersion liquid that is subjected to removal of the organic solvent therefrom is preferably not less than 0.10, more preferably not less than 0.15 and even more preferably not less than 0.20, and is also preferably not more than 0.50, more preferably not more than 0.40 and even more preferably not more than 0.30, from the viewpoint of attaining progressive dispersion of the colorant by improving wettability of the colorant as well as from the viewpoint of improving adsorptivity of the polymer to the colorant.

The method of removing the organic solvent is not particularly limited, and may be conducted by any suitable conventionally known methods. Incidentally, a part of water contained in the colorant dispersion liquid may be removed together with the organic solvent at the same time.

The temperature and time used upon removal of the organic solvent may be appropriately selected according to the kind of organic solvent to be removed.

The organic solvent is preferably substantially completely removed from the aforementioned colorant water dispersion. However, the residual organic solvent may be present in the colorant water dispersion unless the objects and advantageous effects of the present invention are adversely affected by the residual organic solvent. The content of the residual organic solvent in the colorant water dispersion is preferably not more than 0.1% by mass and more preferably not more than 0.01% by mass.

The concentration of non-volatile components in the colorant water dispersion (solid content of the colorant water dispersion) is preferably not less than 10% by mass, more preferably not less than 15% by mass and even more preferably not less than 18% by mass, and is also preferably not more than 30% by mass, more preferably not more than 25% by mass and even more preferably not more than 22% by mass, from the viewpoint of improving dispersion stability of the colorant water dispersion as well as from the viewpoint of facilitating production of the water-based ink. The solid content may be measured by the method described in Examples below.

[Step 3]

In the present invention, from the viewpoint of enhancing a sense of unity of the colored nonwoven fabric with the skin in appearance, and suitably controlling a gloss feel and a transparent feel of the colored nonwoven fabric, a colorant may be further applied to the resulting colored nonwoven fabric by an ink-jet printing method. More specifically, the production process of the present invention may further include the following step 3. The ink-jet printing method used in the step 3 may be conducted using the aforementioned colorant in the form of a water-based ink by the same method as in the aforementioned step 2-2. By conducting the step 3, it is possible to make suitable adjustment between the skin color of the user and the color of the colored nonwoven fabric when attaching the colored nonwoven fabric to the skin, so that the colored nonwoven fabric can also be improved in concealability against scars, etc. In addition, in the step 3, it is also possible to apply decoration or makeup, such as design patterns, characters, tattoos, etc., to the colored nonwoven fabric. Also, in the step 3, a print pattern that is emphasized by illusion may be further applied to the colored nonwoven fabric similarly to the aforementioned step 2-2.

Step 3: applying a colorant to the resulting colored nonwoven fabric by an ink-jet printing method to obtain a colored nonwoven fabric which is further colored with the colorant.

<L* Value Adjusting Step>

The process for producing the colored nonwoven fabric according to the present invention includes an L* value adjusting step of coloring the nanofibers such that an $L*_1$ value of convex portions of the resulting colored nonwoven fabric is higher than an $L*_2$ value of concave portions thereof. By conducting the L* value adjusting step, it is possible to added shading with gradation to the colored nonwoven fabric, for example, produce a three-dimensional feel, such as makeup for making a face look smaller, etc., by emphasizing the depth of the face owing to illusion. In such a method, as compared to the conventional makeup method in which somewhat dark foundation is spread on the side portions of the face by hands, left-right symmetry of the face can be readily ensured, and it is also possible to form high-quality makeup cosmetic coating equivalent to professional application in salons without need thereof and therefore obtain highly valuable makeup cosmetic coating having excellent convenience.

Examples of the coloring method used in the aforementioned L* value adjusting step include a method (ii-1) of applying an ink to conduct printing by an ink-jet printing method such that the $L*_1$ value of the convex portions is higher than the $L*_2$ value value of the concave portions, and a method (ii-2) of applying a colorant by an electrostatic powder spray-coating method (electrostatic powder painting method) such that the $L*_1$ value of the convex portions is higher than the $L*_2$ value value of the concave portions.

(Method (ii-1))

The colorant used as the ink in the method (ii-1) is preferably a white pigment, such as titanium oxide, zinc oxide, etc., from the viewpoint of improving rub fastness of the resulting colored nonwoven fabric and allowing the colored nonwoven fabric to exhibit a good gloss feel and a good transparent feel as well as from the viewpoint of improving a sense of unity of the colored nonwoven fabric with the skin in appearance, a resilient feel of the skin and a skin age.

In the method (ii-1), in the case where the method (i-1) is used as the coloring method of the colored nonwoven fabric, it is preferred that after obtaining the colored nonwoven fabric in the step 1-1, the step 3 is conducted to apply a white pigment to the convex portions of the resulting colored nonwoven fabric by an ink-jet printing method such that the $L*_1$ value of the convex portions is higher than the $L*_2$ value value of the concave portions.

In the method (ii-1), in the case where the method (i-2) is used as the coloring method of the colored nonwoven fabric, after obtaining the uncolored nonwoven fabric in the step 2-1, the step 2-2 is conducted to apply a white pigment and a coloring pigment to the uncolored nonwoven fabric obtained in the step 2-1 by an ink-jet printing method such that the $L^*_1$ value of the convex portions is higher than the $L^*_2$ value value of the concave portions.

Incidentally, in the step 3 or the step 2-2, by applying a dark coloring pigment to the concave portions by an ink-jet printing method to impart shading to the concave portions, the $L^*_1$ value of the convex portions may also become higher than the $L^*_2$ value value of the concave portions.

(Method (ii-2))

The electrostatic powder spray-coating method is such a method in which by applying a high voltage to a powder, an electric charge opposite to that of the powder is generated at a substrate grounded so as to electrostatically adhere the powder and the substrate to each other. In the method (ii-2), by using the colorant as the powder for the electrostatic powder spray-coating method, the colorant is applied to the convex portions of the colored nonwoven fabric such that the $L^*_1$ value of the convex portions of the resulting colored nonwoven fabric is higher than the $L^*_2$ value value of the concave portions thereof. As the colorant, a glitter pigment is preferably used. More specifically, the process for producing the colored nonwoven fabric according to the present invention preferably includes, as the aforementioned L* value adjusting step, the step of applying the glitter pigment such that the $L^*_1$ value of the convex portions of the resulting colored nonwoven fabric is higher than the $L^*_2$ value value of the concave portions thereof.

In the aforementioned step of applying the glitter pigment, from the viewpoint of uniformly applying the pigment to the convex portions of the colored nonwoven fabric, it is preferred that prior to the electrospinning step, the glitter pigment is applied to the concave portions of the concavo-convex plate by an electrostatic powder spray-coating method. In the present invention, by adjusting an amount of the glitter pigment applied as the colorant to the concave portions of the concavo-convex plate by the electrostatic powder spray-coating method such that the $L^*_1$ value of the convex portions is higher than the $L^*_2$ value value of the concave portions, or a position of the concave portions to which the glitter pigment is applied, it is possible to control the L* value of the convex portions of the resulting colored nonwoven fabric.

The voltage applied to a tip end of a spray gun for ejecting the glitter pigment which is used in the electrostatic powder spray-coating method is preferably not less than 30 kV, more preferably not less than 50 kV and even more preferably not less than 70 kV, and is also preferably not more than 150 kV, more preferably not more than 130 kV and even more preferably not more than 110 kV.

The current value of the spray gun is preferably not less than 10 μA and more preferably not less than 30 μA, and is also preferably not more than 70 μA and more preferably not more than 50 μA.

The distance between the injection port of the spray gun and the concavo-convex plate is preferably controlled to not less than 100 mm and more preferably not less than 200 mm, and also preferably controlled to not more than 500 mm and more preferably not more than 400 mm.

The amount of the glitter pigment ejected assuming that the amount of the glitter pigment ejected as measured at a primary side (upstream side) pressure of 0.5 MPa is 100% is preferably not less than 10% and more preferably not less than 30%, and is also preferably not more than 90% and more preferably not more than 70%.

The amount of air for transporting the glitter pigment is preferably not less than 10 L/min and more preferably not less than 30 L/min, and is also preferably not more than 100 L/min and more preferably not more than 70 L/min.

The number of the glitter pigments applied per one concave portion by an electrostatic powder spray-coating method is preferably controlled to not less than 1 and not more than 3, whereby it is possible to suitably adjust a gloss feel and a transparent feel and improve a resilient feel of the skin and a skin age.

Moreover, in the present invention, in the case where the texture structure of the skin is formed on the colored nonwoven fabric as the uneven shape thereof using the method (ii-1) in combination with the method (ii-2), by not only preliminarily allowing a material having a high luster or high L* value, such as a glitter pigment, etc., to locally exist in the concave portions of the concavo-convex plate which are portions corresponding to skin hills, but also applying the colorant capable of lowering the L* value to the convex portions of the concavo-convex plate which are portions corresponding to a foot of respective skin grooves or skin hills by an ink-jet printing method, etc., it is possible to emphasize the texture structure of the skin as the uneven shape more visually than really. By thus visually emphasizing the unevenness of the texture structure of the skin on the colored nonwoven fabric, a resilient feel of the skin or a wet feel of the skin capable of creating the resilient feel can be recognized by another person to make the skin age look younger.

(Colored Nonwoven Fabric)

In the colored nonwoven fabric of the present invention, the nanofibers are entangled with each other, whereby the colored nonwoven fabric is capable of maintaining a sheet-like configuration by itself.

The thickness of the respective nanofibers in the colored nonwoven fabric according to the present invention as represented by an equivalent circle diameter thereof is preferably not less than 10 nm, more preferably not less than 50 nm and even more preferably not less than 80 nm, and is also preferably not more than 3,000 nm and more preferably not more than 1,000 nm. The thickness of the respective nanofibers may be measured, for example, by observing the nanofibers by a scanning electron microscope (SEM) at a magnification of 10,000 times, in which optional 10 nanofibers are selected from those in the colored nonwoven fabric, and a line perpendicular to a longitudinal direction of the respective nanofibers is drawn to directly read a fiber diameter of the nanofiber.

The configuration of the colored nonwoven fabric of the present invention is preferably a thin sheet-like shape from the viewpoint of attaching the colored nonwoven fabric to the skin of the user upon use. From the viewpoint of improving handling properties of the colored nonwoven fabric when attaching the colored nonwoven fabric to the skin of the user upon use, the thickness of the colored nonwoven fabric is preferably not less than 50 nm, more preferably not less than 500 nm, even more preferably not less than 1 μm and further even more preferably not less than 5 μm, and is also preferably not more than 1 mm, more preferably not more than 500 μm, even more preferably not more than 300 μm and further even more preferably not more than 100 μm. By adjusting the thickness of the colored nonwoven fabric to the aforementioned range, a difference in level between the edge portion of the colored nonwoven fabric and the skin of the user tends to be hardly caused, so that a sense of unity of the colored nonwoven fabric with the skin of the user in appearance can be enhanced. In addition, when attaching the colored nonwoven fabric onto fine uneven portions on the skin, for example, skin portions of fine wrinkles or pores, it is possible to conceal these fine wrinkles or pores. From the same viewpoint as described above, the basis weight of the colored nonwoven fabric is preferably controlled to the range of not less than 0.01 $g/m^2$ and more preferably not less than 0.1 $g/m^2$, and also preferably controlled to the range of not more than 100 $g/m^2$ and more preferably not more than 50 $g/m^2$.

The thickness of the colored nonwoven fabric may be measured by the method described in Examples below.

[Substrate Sheet]

The colored nonwoven fabric of the present invention may have either a single layer structure that is formed of the colorant and the nanofibers, or a multi-layer structure that is formed by laminating the colored nonwoven fabric containing the colorant and the nanofibers, and the other sheet(s) on each other. As the other sheet(s) which may be used in combination with the colored nonwoven fabric, for example, from the viewpoint of supporting the colored nonwoven fabric prior to its use as well as from the viewpoint of enhancing handling properties thereof, there may be used a substrate sheet. In the case where the colored nonwoven fabric has a small thickness, the colored nonwoven fabric can be used in combination with the substrate sheet to attain good handling properties of the colored nonwoven fabric when attached to the skin.

The substrate sheet is preferably used in the form of a mesh sheet.

In the present invention, by using the mesh sheet as the substrate sheet, when depositing the nanofibers on the collector, the nanofibers can be allowed to reach the collector having the uneven structure through pores of the mesh sheet, so that it is possible to obtain the colored nonwoven fabric that is provided with the mesh sheet as a core material while maintaining an uneven shape thereof. In this case, the mesh opening of the mesh sheet is preferably controlled to from 20 to 200 meshes/inch, especially preferably from 50 to 150 meshes/inch. In addition, the wire diameter of meshes of the mesh sheet is preferably from 10 to 200 μm, especially preferably from 30 to 150 μm. The material of the mesh sheet is preferably the same material as that of the nanofibers, though it is not particularly limited thereto.

[Release Sheet]

The colored nonwoven fabric of the present invention may also be provided with a release sheet. In this case, it is preferred that the release sheet is releasably laminated on the colored nonwoven fabric. With such a construction, after adhering the side of the colored nonwoven fabric, for example, to the skin, the release sheet may be peeled off and removed from the colored nonwoven fabric, whereby it is possible to maintain the colored nonwoven fabric in such a state as attached to the skin. From this viewpoint, it is preferred that the release sheet is directly laminated on the surface of the colored nonwoven fabric.

The Taber stiffness of the release sheet is preferably from 0.01 to 0.4 mN·m and more preferably from 0.01 to 0.2 mN·m from the viewpoint of improving handling properties of the colored nonwoven fabric. The Taber stiffness may be measured by "Stiffness Testing Method" prescribed in JIS P8125: 2000.

The thickness of the release sheet may vary depending upon a material of the release sheet, and is preferably from 5 to 500 μm and more preferably from 10 to 300 μm from the viewpoint of improving handling properties of the colored nonwoven fabric. The thickness of the release sheet may be measured by the same method as used for measuring the thickness of the colored nonwoven fabric.

In the present invention, when using the aforementioned grain-like artificial leather as the collector, the grain-like artificial leather may also be used as the release sheet for the colored nonwoven fabric. More specifically, in the configuration of laminating the colored nonwoven fabric on the grain-like artificial leather, after opposing the side of the colored nonwoven fabric to the skin, the surface of the colored nonwoven fabric is attached onto the skin. Then, the grain-like artificial leather is peeled off and removed from the colored nonwoven fabric, whereby only the colored nonwoven fabric remains attached to the skin. According to this method, it is possible to easily attach the colored nonwoven fabric to the skin even though the colored nonwoven fabric has a small thickness and therefore a low stiffness.

The release sheet preferably has slight heat shrinkability from the viewpoint of improving adhesion properties of the colored nonwoven fabric to the skin. With the heat shrinkability of the release sheet, by heating the side of the release sheet after attaching the colored nonwoven fabric to the skin, the colored nonwoven fabric can be readily peeled and separated from the release sheet, so that it is possible to attain a good releasing state of the colored nonwoven fabric while reducing a physical force applied to the colored nonwoven fabric to a minimum level.

The release sheet is preferably so designed as to be releasable dividedly in parts from the colored nonwoven fabric. The release sheet having a small area can be released only by applying a weak force thereto. However, if it is intended to release the release sheet having a large area at the same time, it will be necessary to apply a large force thereto, which might result in deteriorated releasability thereof in some cases. In consequence, the release sheet is divided into parts to reduce a maximum value of a released area of the sheet to which a release force is applied simultaneously upon the releasing, so that it is possible to prevent a tension force exceeding durability of the colored nonwoven fabric from being applied thereto.

The release sheet also preferably has air permeability. When suitably selecting a material through which fibers or liquids are impermeable, but water vapor or air is permeable as the material of the release sheet, it is possible to release the release sheet from the colored nonwoven fabric even though the surface of the colored nonwoven fabric has a fine uneven shape. More specifically, the Gurley air permeability of the release sheet is preferably not more than 30 seconds/100 mL and more preferably not more than 20 seconds/100 mL. The Gurley air permeability of the release sheet may be measured by the method prescribed in JIS P8117: 2009. The lower limit of the Gurley air permeability of the release sheet may be determined in consideration of the aforementioned Table stiffness of the release sheet, and the like.

(Method of Using Colored Nonwoven Fabric)

The colored nonwoven fabric of the present invention is preferably used by attaching the colored nonwoven fabric to the skin of the user.

When attaching the colored nonwoven fabric of the present invention to the skin of the user, an attachment assistant agent may be applied to the skin, and then the colored nonwoven fabric may be attached to the portion of the skin to which the attachment assistant agent is applied. More specifically, it is preferred that for example, after wetting the skin of the user with a liquid material or wetting the surface of the colored nonwoven fabric with the liquid material as the attachment assistant agent, the surface of the colored nonwoven fabric is brought into contact with the skin. With this procedure, it is possible to suitably adhere the colored nonwoven fabric to the skin by the action of surface tension.

As the method of keeping the surface of the skin or the colored nonwoven fabric in a wet state, there may be mentioned, for example, a method of spreading or spraying the liquid material thereonto. As the liquid material to be spread or sprayed, there may be used an aqueous liquid or an oily liquid. The aforementioned liquid material preferably has a higher surface tension no matter whether any of an aqueous liquid and an oily liquid is used as the liquid material.

In the present invention, in the case where the nanofibers contain a water-soluble polymer compound, an oily liquid may be used as the liquid material. However, it is more preferable to use an aqueous liquid as the liquid material. As the aqueous liquid, there may be used a substance containing water and having a viscosity of about 5,000 mPa s or less as measured at 25° C. Examples of such a liquid material include water, an aqueous solution, a water dispersion liquid, etc., as well as cosmetic emulsions for makeup, such as O/W emulsions or W/O emulsions, liquids thickened with a thickener, and the like. More specifically, as the liquid material, there may be used commercially available products, such as a skin lotion or a cosmetic cream.

As to the degree of wetting the surface of the skin or the surface of the colored nonwoven fabric by spreading or spraying the liquid material thereover, it suffices that the liquid material be applied in such a minimum amount as required to allow the liquid material to sufficiently exhibit its surface tension.

In addition, in the case where an aqueous liquid is used as the liquid material, it suffices that the aqueous liquid be applied in such a minimum amount as required for the aqueous liquid to sufficiently exhibit its surface tension and to dissolve the water-soluble polymer compound therein. More specifically, although the amount of the liquid material to be applied may vary depending upon the size of the colored nonwoven fabric, in the case where the colored nonwoven fabric has a square shape of 3 cm×3 cm, the application of about 0.01 ml of the liquid material to the surface of the skin will be enough to attach the colored nonwoven fabric to the skin easily. When using the aqueous liquid as the liquid material and further using the water-soluble polymer compound, it is possible to exhibit a binder effect by dissolving the water-soluble polymer compound contained in the nanofibers in the aqueous liquid, as described previously.

In addition, a solid or semisolid pre-makeup primer may be used as the attachment assistant agent in place of, or in addition to, a skin lotion or a cosmetic cream. The pre-makeup primer may be applied to the skin portion before the colored nonwoven fabric is attached thereto. Since the pre-makeup primer has the effect of smoothening the surface of the skin, the application of the colored nonwoven fabric to the skin under such a skin condition further improves adhesion of the colored nonwoven fabric to the skin, and further enhances the sense of unity of the colored nonwoven fabric with the skin in appearance.

Under such a condition that the liquid material is present between the colored nonwoven fabric and the skin, the bonding between the nanofibers is weakened due to the presence of the liquid material. In particular, in the case where the water-soluble polymer compound is contained in the nanofibers, the water-soluble polymer compound in the nanofibers is dissolved in the liquid material after attaching the colored nonwoven fabric to the skin, so that the bonding between the nanofibers is furthermore weakened. In this state, the fiber bonds at the periphery of the colored nonwoven fabric may be sheared (shifted) to thereby reduce the difference in level between the colored nonwoven fabric and the skin. As a result, the boundary between the colored nonwoven fabric and the skin is made less discernible to further enhance a sense of unity of the colored nonwoven fabric with the skin in appearance. Shearing the fiber bonds at the periphery of the colored nonwoven fabric can be achieved, for example, by applying a shear force to the peripheral portion of the colored nonwoven fabric which is kept in such a state as wetted by the liquid material after being attached to the skin. The shear force can be applied, for example, by lightly rubbing or stroking the peripheral portion of the colored nonwoven fabric with a finger, a nail, or a makeup tool, such as a sponge, a cosmetic spatula, etc.

By thus transferring and attaching the colored nonwoven fabric having the uneven surface shape to the skin, it is possible to cover fine skin surface unevenness, such as fine wrinkles and pores, with the transferred colored nonwoven fabric to diminish the skin surface unevenness, and further an impression of a neat texture of the skin can be imparted by the uneven shape of the surface of the colored nonwoven fabric which has been preliminarily designed thereon.

Moreover, the uneven shape of the colored nonwoven fabric attached to the skin reflects the unevenness of a facial contour of the user before attaching the colored nonwoven fabric thereto while reproducing the texture structure of the skin, so that the colored nonwoven fabric attached takes on an extremely natural surface profile and gloss. Therefore, such unnaturalness as observed when a thick film, for example, such as a silicone sheet, etc., is attached to the skin will hardly be perceived.

In addition, the colored nonwoven fabric attached to the skin serves for hiding or reducing skin color unevenness due to spots, freckles, bags under eyes, etc., and can exert good concealing effect thereon.

Also, the colored nonwoven fabric attached to the skin has high adhesion to the skin, and is therefore less likely to lose a sense of unity with the skin in appearance even though it is attached, for example, all day long. Even when attaching the colored nonwoven fabric to the skin for a long period of time, the colored nonwoven fabric having air permeability is less likely to impede the regulatory mechanism essentially possessed by the skin. Besides, even after the colored nonwoven fabric is continuously attached to the skin for a long period of time, the colored nonwoven fabric is easily removed from the skin simply by picking up between fingers.

After the colored nonwoven fabric of the present invention is attached to the skin, makeup cosmetics may be put on the colored nonwoven fabric to thereby further enhance a sense of unity of the colored nonwoven fabric with the skin in appearance. Examples of the makeup cosmetics that may be put on the colored nonwoven fabric in such a case include an oil and an milky lotion containing the oil. The oil or the milky lotions applied to the colored nonwoven fabric is retained between the nanofibers constituting the colored nonwoven fabric, which can further enhance a sense of unity of the colored nonwoven fabric with the skin in appearance. The oil to be used preferably has a viscosity of from 5.5 to 100 mPa·s as measured at room temperature (25° C.). Examples of the oil include hydrocarbon oils, polydimethylsiloxane (silicone oil), and the like. Of these oils, from the viewpoint of improving makeup longevity, preferred is polydimethylsiloxane (silicone oil).

After the colored nonwoven fabric of the present invention is attached to the skin, various powdery makeup cosmetics, such as powder foundation, may be further put on the colored nonwoven fabric attached to the skin. In this case, by virtue of the thickness of the nanofibers or the distance between the nanofibers in the colored nonwoven fabric, the powdery makeup cosmetics can be well spread on the colored nonwoven fabric, so that it is possible to enhance a sense of unity in appearance between a portion of the skin to which the powdery makeup cosmetics are directly applied, and the nonwoven fabric on which the powdery makeup cosmetics are put.

EXAMPLES

In the following descriptions, "%" indicate "% by mass," unless otherwise specified. Meanwhile, properties of polymers, etc., were measured by the following methods.

(1) Measurement of Average Primary Particle Size and Average Thickness of Glitter Pigment Using a transmission electron microscope "JEM-2100" available form JEOL Ltd., 500 primary particles of the glitter pigment were extracted by image analysis to measure their particle sizes and thicknesses and calculate respective average values thereof. The number-average value of the thus measured primary particles size and the number-average value of the thus measured thicknesses were defined as an average primary particle size and an average thickness of the glitter pigment, respectively. Meanwhile, in the case where the glitter pigment particles had a major axis diameter and a minor axis diameter, the average primary particle size of the glitter pigment were calculated by using the major axis diameter thereof.

(2) Measurement of Number-Average Molecular Weight of Poly(N-Propionyl Ethyleneimine)

The number-average molecular weight of poly(N-propionyl ethyleneimine) was measured by gel permeation chromatography [measuring columns: two columns "K-804L" available from SHOWA DENKO K.K., connected in series to each other; flow rate: 1 mL/min; column temperature: 40° C.; detector: differential refractometer] using a 1 mmol/L solution of "FARMIN DM20" (tradename) available from Kao Corporation in chloroform as an eluent, and using polystyrenes having previously known molecular weights as a reference standard substance. The sample to be measured was used in an amount of 100 μL at a concentration of 5 mg/mL.

(3) Measurement of Volume-Average Particle Size of Non-White Colorant Particles

Using the following measuring apparatus, the volume-average particle size of the non-white colorant particles was measured under the following conditions.

Measuring Apparatus: Zeta potential/particle size measuring system "ELS-8000" commercially available from Otsuka Electrics Co., Ltd.

Measuring Conditions: Cumulant Analysis

The dispersion containing the particles to be measured was diluted with water so as to adjust a concentration of the particles therein to about $5\times10^{-3}$%, and the resulting dilute dispersion was filled in a cell for measurement. The measurement was conducted at a measuring temperature of 25° C. and a cumulative number of 100 times, and a refractive index of water (1.333) was input to the measuring system as a refractive index of the dispersive solvent.

(4) Measurement of Volume-Average Particle Size of White Colorant Particles (Titanium Oxide Pigment Particles)

Using a laser diffraction/scattering particle size distribution measuring apparatus "LA950" available from HORIBA Ltd., under the condition that a refractive index of the titanium oxide and a refractive index of water were regarded as being 2.75 and 1.333, respectively, and further scales of a circulating rate and an ultrasonic wave of the apparatus were set at "5" and "3", respectively, a dispersion of the titanium oxide pigment particles was irradiated with an ultrasonic wave for 1 minute, followed by measuring particle sizes of the titanium oxide pigment particles in the dispersion. At this time, the value of the volume median particle size (Do) thus measured was determined as a volume-average particle size of the titanium oxide pigment particles.

(5) Measurement of Solid Content

Using an infrared moisture meter "FD-230" available from Kett Electric Laboratory, 5 g of a sample to be measured was dried at a drying temperature of 150° C. under a measuring mode 96 (monitoring time: 2.5 minutes/variation range: 0.05%) to measure a water content (%) of the sample to be measured. The solid content of the sample was calculated according to the following formula.

Solid Content (%)=100−Water Content (%) of Sample to be Measured (6) Measurement of Static Surface Tension of Water-Based Ink A platinum plate was dipped in 5 g of a sample adjusted to 20° C. which was filled in a cylindrical polyethylene container (3.6 cm in diameter×1.2 cm in depth), and the static surface tension of the sample was measured at 20° C. using a surface tension meter "CBVP-Z" available from Kyowa Interface Science Co., Ltd., by a Wilhelmy method.

(7) Measurement of Viscosity of Water-Based Ink

The viscosity of the water-based ink was measured at 35° C. using an E-type viscometer "TV-25" (equipped with a standard cone rotor (1°34'×R24); rotating speed: 50 rpm) available from Toki Sangyo Co., Ltd.

(8) Ascertainment and Measurement of Uneven Structure of Collector

The ascertainment and measurement of the uneven structure of the collector were implemented by 3D measurement based on sectional profile using an industrial microscope "LEXT-OLS5000-SAT" available from Olympus Corporation. While appropriately changing a magnification of an objective lens of the microscope, the shape of the uneven structure on the surface of the collector was ascertained, and further the measurement was conducted at 20 points selected as measuring objects per one sample to be measured to calculate an average value of the thus measured values as a measurement value, thereby obtaining respective average lengths of opening portions and bottoms portions of the concavo-convex plate, an average depth of concave portions thereof, an average width of convex portions thereof, an average center distance of the uneven structure thereof, or a texture depth of the texture sample.

(9) Ascertainment and Measurement of Uneven Shape of Colored Nonwoven Fabric

The ascertainment and measurement of the uneven shape of the colored nonwoven fabric were implemented by 3D measurement based on sectional profile using an industrial microscope "LEXT-OLS5000-SAT" available from Olympus Corporation. While appropriately changing a magnification of an objective lens of the microscope, the uneven shape on the surface of the colored nonwoven fabric was ascertained, and further the measurement was conducted at 20 points selected as measuring objects to calculate an average value of the thus measured values as a measurement value, thereby obtaining an average length of convex portions of the colored nonwoven fabric as viewed on a plan view thereof, an average height of the convex portions, or a texture depth of the texture sample.

(10) Measurement of Thickness of Colored Nonwoven Fabric

The thickness of the colored nonwoven fabric was measured using a contact thickness gauge "LITEMATIC VL-50A" available from Mitutoyo Corporation. Incidentally, the measurement was conducted by using an R 5 mm cemented carbide spherical probe and applying a load of 0.01 Pa to the colored nonwoven fabric.

(11) Measurement of $L^*_1$ Value of Convex Portions and $L^*_2$ Value of Concave Portions <Measurement of $L^*_1$ Value of Convex Portions>

Using an industrial microscope "LEXT-OLS5000-SAT" available from Olympus Corporation, the colored nonwoven fabric was placed thereon so as to allow both of a white plate and a black plate of color standard plates "CCS-2; 5 cm square; flat dull set" available from Murakami Color Research Laboratory Co., Ltd., to enter within a visual field, and microphotographed.

The microphotographed image (1) was saved in TIFF format, and subjected to image analysis using an image analyzing software "Image J" available from The National Institutes of Health. First, using an image transformation function of "Image J", the image (1) was converted into a 8-bit gray-scale image (2), and the image (2) was saved again in TIFF format. The image (2) was opened using an image editing software "Photoshop (registered trademark)" available from Adobe Inc., and using a dropper function of the software, it was ascertained that the L* value at a portion of the white plate was 100, whereas the L* value at a portion of the black plate was 0. If each L* value was deviated, the intensity of a light source was adjusted. Next, the image (2) was opened again by "Image J" to specify the range of portions corresponding to the convex portions of the colored nonwoven fabric using a range specifying tool of the software to analyze a brightness of the image by histogram and thereby calculate an average value thereof. Since the 8-bit gray-scale image was indicated by 256 gradations from 0 for darkest gradation to 255 for lightest gradation, the gray-scale value was multiplied by 100/256 time to convert the gray-scale value into an L* value.

<Measurement of $L^*_2$ Value of Concave Portions>

The same procedure as described above for measuring the $L^*_1$ value of the convex portions was repeated except for specify the range of portions corresponding to the concave portions of the colored nonwoven fabric using the range specifying tool of the software, thereby measuring the $L^*_2$ value of the concave portions.

Synthesis Example 1 (Synthesis of Cationic Silicone Polymer 1)

A mixed solution prepared by mixing 73.7 g (0.74 mol) of 2-ethyl-2-oxazoline and 156.0 g of ethyl acetate was dehydrated with 12.0 g of a molecular sieve "ZEOLUM A-4" available from Tosoh Corporation at 28° C. for 15 hours. The resulting dehydrated ethyl acetate solution of 2-ethyl-2-oxazoline was mixed with 2.16 g (0.014 mol) of diethyl sulfate, and the obtained mixture was refluxed under heating at 80° C. in a nitrogen atmosphere for 8 hours, thereby obtaining a solution of terminal-reactive poly(N-propionyl ethyleneimine) (number-average molecular weight: 6,000).

Separately, a mixed solution prepared by mixing 70.0 g of a side-chain primary aminopropyl-modified poly(dimethyl siloxane) "KF-864" (weight-average molecular weight: 50,000 (catalogue value); amine equivalent: 3,800) available from Shin-Etsu Chemical Co., Ltd., and 140.0 g of ethyl acetate with each other was dehydrated with 15.0 g of the molecular sieve at 28° C. for 15 hours.

Next, the terminal-reactive poly(N-propionyl ethyleneimine) solution obtained above was added to the aforementioned dehydrated side-chain primary aminopropyl-modified poly(dimethyl siloxane) solution at one time, followed by refluxing the obtained mixed solution under heating at 80° C. for 10 hours. The resulting reaction mixture was concentrated under reduced pressure to obtain a poly(N-propionyl ethylene imine)/dimethyl polysiloxane copolymer (hereinafter also referred to as a "cationic silicone polymer 1") in the form of a white rubber-like solid (135 g). The mass ratio of a content of an organopolysiloxane segment (x) to a total content of the organopolysiloxane segment (x) and a poly(N-acyl alkylene imine) segment (y) [content of organopolysiloxane segment (x)/total content of organopolysiloxane segment (x) and poly(N-acyl alkylene imine) segment (y)] in the polymer was 0.50, and the weight-average molecular weight of the cationic silicone polymer 1 was 100,000 (calculated value). The resulting cationic silicone polymer 1 was mixed with a first-grade ethanol, thereby obtaining a solution of the cationic silicone polymer 1 (solid content: 30%).

Production Examples 1-1 to 1-5 (Production of Non-White Pigment Water Dispersion)

(Step I: Production of Colorant Dispersion Liquid)

A sealable and temperature-controllable glass jacket was charged with 200 g of a solution of an anionic acrylic polymer "Plascize L-9909B" (acid value: 50 mgKOH/g; unneutralized product; an ethanol solution having a solid content of 40%) as a water-dispersive polymer available from GOO Chemical Co., Ltd. While stirring the solution under the conditions including a jacket temperature of 15° C. and a rotating speed of 1,400 rpm using a high-speed disperser "T.K. ROBOMIX" (equipped with "HOMODISPER 2.5 Model" as a stirring device (blade diameter: 40 mm)) available from Primix Corporation, 200 g of the colorant shown in Table 1 was added thereto, and the resulting mixture was further stirred under the conditions including a jacket temperature of 15° C. and a rotating speed of 2,000 rpm for 1 hour to render the colorant compatible with the anionic acrylic polymer solution.

Next, while maintaining the jacket temperature of 15° C., the rotating speed of the disperser was changed to 8,000 rpm at which 170 g of the first grade ethanol, 17.1 g of a 5N NaOH aqueous solution and 412.9 g of ion-exchanged water were charged into the jacket, and the contents of the jacket were stirred for 3 hours, thereby obtaining a colorant mixture (concentration of ethanol in medium: 40.4%; solid content: 28%).

The thus obtained colorant mixture was subjected to dispersion treatment by passing the mixture through a Microfluidizer "Model: M-140K" available from Microfluidics Corporation under a pressure of 180 MPa 20 times (number of passes), followed by adding 900 g of ion-exchanged water thereto, thereby obtaining respective colorant dispersion liquids each having a solid content of 14.7%.

The thus obtained colorant dispersion liquids were respectively subjected to measurement for a volume-average particle size of colorant particles contained therein. The volume-average particle sizes of the colorant particles in the respective colorant dispersion liquids are shown in Table 1.

Red No. 104-(1): Red pigment "Sun CROMA D & C Red 28 Al Lake" (C.I. Acid Red 92) available from Sun Chemical Corporation.

Red No. 226: Red dye; "Red No. 226 K" (C.I. Vat Red 1) available from Kishi Kasei Co., Ltd.

TABLE 1

| | | | Production Examples | | | | |
|---|---|---|---|---|---|---|---|
| | | | 1-1 | 1-2 | 1-3 | 1-4 | 1-5 |
| No. of colorant water dispersion | | | 1 | 2 | 3 | 4 | 5 |
| Step I | Kind of colorant | | Yellow No. 5 | Yellow No. 4 | Blue No. 1 | Red No. 104-(1) | Red No. 226 |
| | Formulation of colorant mixture (g) | Colorant | 200 | 200 | 200 | 200 | 200 |
| | | Solution of anionic acrylic polymer (solid content: 40%) | 200 | 200 | 200 | 200 | 200 |
| | | Ethanol | 170 | 170 | 170 | 170 | 170 |
| | | Ion-exchanged water | 412.9 | 412.9 | 412.9 | 412.9 | 412.9 |
| | | 5N NaOH aqueous solution | 17.1 | 17.1 | 17.1 | 17.1 | 17.1 |
| | Mass ratio [colorant/water-dispersive polymer] in colorant mixture | | 2.5 | 2.5 | 2.2 | 2.5 | 2.5 |
| | Mass ratio [organic solvent/water] in colorant mixture | | 0.68 | 0.68 | 0.68 | 0.68 | 0.68 |
| | Conditions of dispersion treatment of colorant mixture | | 180 MPa; 20 passes | | | | |
| | Amount (g) of ion-exchanged water added after dispersion treatment | | 900 | 900 | 900 | 900 | 900 |
| | Solid content (%) of colorant dispersion liquid | | 14.7 | 14.7 | 14.7 | 14.7 | 14.7 |
| | Volume-average particle size (nm) of colorant particles in colorant dispersion liquid | | 160 | 173 | 129 | 112 | 156 |
| Step II | Mass ratio [organic solvent/water] in colorant dispersion liquid | | 0.22 | 0.22 | 0.22 | 0.22 | 0.22 |
| | Conditions for removal of organic solvent | | 40° C.; 10 kPa; 2 hr + 62° C.; 7 kPa; 4 hr | | | | |
| | Solid content (%) of colorant water dispersion | | 20.0 | 20.0 | 20.0 | 20.0 | 20.0 |
| | Volume-average particle size (nm) of colorant particles in colorant water dispersion | | 157 | 169 | 125 | 109 | 152 |

(Step II: Removal of Organic Solvent)

Using a reduced-pressure distillation apparatus (rotary evaporator) "N-1000S Model" available from Tokyo Rikakikai Co., Ltd., the resulting colorant dispersion liquids were respectively maintained in a warm bath adjusted to 40° C. under a pressure of 10 kPa for 2 hours to remove the organic solvent therefrom. The resulting dispersion was further maintained in the warm bath adjusted to 62° C. under the pressure reduced to 7 kPa for 4 hours to remove the organic solvent and a part of water therefrom such that a total concentration of the colorant and the water-dispersive polymer in the dispersion (solid content) was controlled to the range of from 23 to 25%. Then, while measuring the total concentration of the colorant and the water-dispersive polymer (solid content), ion-exchanged water was added to the dispersion so as to control the total concentration of the colorant and the water-dispersive polymer therein to 20.0%.

Next, the thus obtained respective dispersions were subjected to filtration treatment by passing through 5 μm-mesh and 1.2 μm-mesh membrane filters "Minisart" available from Sartorius Inc., in sequential order, thereby obtaining respective colorant water dispersions.

The volume-average particle sizes of the colorant particles in the resulting respective colorant water dispersions are shown in Table 1.

The details of the colorants shown in Table 1 are as follows.

Yellow No. 5: Yellow pigment "Sun CROMA FD & C Yellow 6 Al Lake" (C.I. Pigment Yellow 104) available from Sun Chemical Corporation.

Yellow No. 4: Yellow pigment "BC Yellow #4 AL" (C.I. Pigment Yellow 100) available from Kishi Kasei Co., Ltd.

Blue No. 1: Blue pigment "Sun CROMA FD & C Blue 1 Al Lake" (C.I. Food Blue 2 Aluminum Lake) available from Sun Chemical Corporation.

Production Example 1-6 (Production of White Pigment Water Dispersion)

(Step I: Colorant Dispersing Step)

A 1000 mL-capacity polypropylene bottle available from SANPLATEC Corporation was charged with 33.4 g of the solution of the cationic silicone polymer 1 (solid content: 30%) obtained as the water-dispersive polymer in Synthesis Example 1, 200 g of a titanium oxide pigment "SI-Titan CR-50LHC" (surface-treated titanium oxide: treated with aluminum hydroxide and hydrogen dimethicone) as a white pigment available from Miyoshi Kasei Inc., 170 g of first-grade ethanol, and 1.6 g of citric acid. The contents of the bottle were shaken by hand to fully suspend the titanium oxide pigment in the solution of the cationic silicone polymer 1.

Then, 2,000 g of 1.2 mmϕ zirconia beads were added to the resulting suspension, and the obtained mixture was subjected to dispersion treatment using a bench top-type pot mill pedestal available from AS ONE Corporation at 250 rpm for 8 hours, followed by subjecting the resulting dispersion to filtration treatment through a metal mesh filter to remove the zirconia beads from the dispersion.

Next, while stirring the obtained dispersion at a rotating speed of 1,400 rpm using a high-speed disperser "T.K. ROBOMIX" (equipped with "HOMODISPER 2.5 Model" (blade diameter: 40 mm) as a stirring device) available from Primix Corporation, 200 g of a solution of an anionic acrylic polymer "Plascize L-9909B" (acid value: 50 mgKOH/g; unneutralized product; an ethanol solution having a solid content of 40%) as a water-dispersive polymer available from GOO Chemical Co., Ltd., was added to the dispersion, followed by increasing the rotating speed up to 2,000 rpm at which the dispersion was stirred for 1 hour. Then, after the rotating speed was changed to 8,000 rpm at a jacket temperature of 15° C., 17.1 g of a 5N NaOH aqueous solution and 412.9 g of ion-exchanged water were added to the dispersion, and the resulting mixture was stirred for 3 hours, thereby obtaining a colorant mixture (concentration of ethanol in medium: 42.3%; solid content: 28%).

The thus obtained colorant mixture was subjected to dispersion treatment by passing the mixture through a Microfluidizer "Model: M-140K" available from Microfluidics Corporation under a pressure of 180 MPa 20 times (number of passes), followed by adding 900 g of ion-exchanged water thereto, thereby obtaining a colorant dispersion liquid having a solid content of 14.7%. The thus obtained colorant dispersion liquid was subjected to measurement for a volume-average particle size of colorant particles contained therein. The volume-average particle sizes of the colorant particles in the colorant dispersion liquid is shown in Table 2.

(Step I: Step of Removing Organic Solvent)

The same method for conducting the step II as described in Production Examples 1-1 to 1-5 was repeated to obtain a colorant water dispersion 6. The thus obtained colorant water dispersion 6 was subjected to measurement for a volume-average particle size of colorant particles contained therein. The volume-average particle size of the colorant particles in the colorant water dispersion 6 is shown in Table 2.

TABLE 2

| | | | Production Example 1-6 |
|---|---|---|---|
| No. of colorant water dispersion | | | 6 |
| Step I | Kind of colorant | | SI-Titan CR-50LHC |
| | Formulation of colorant mixture (g) | Colorant | 200 |
| | | Solution of cationic silicone polymer 1 (solid content: 30%) | 33.4 |
| | | Ethanol | 170 |
| | | Citric acid | 1.6 |
| | | Solution of anionic acrylic polymer (solid content: 40%) | 200 |
| | | Ion-exchanged water | 412.9 |
| | | 5N NaOH aqueous solution | 17.1 |
| | Mass ratio [colorant/water-dispersive polymer] in colorant mixture | | 2.2 |
| | Mass ratio [organic solvent/water] in colorant mixture | | 0.73 |
| | Conditions of dispersion treatment of colorant mixture | | 180 MPa; 20 passes |
| | Amount (g) of ion-exchanged water added after dispersion treatment | | 900 |
| | Solid content (%) of colorant dispersion liquid | | 14.7 |
| | Volume-average particle size (nm) of colorant particles in colorant dispersion liquid | | 325 |
| Step II | Mass ratio [organic solvent/water] in colorant dispersion liquid | | 0.22 |
| | Conditions for removal of organic solvent | | 40° C.; 10 kPa; 2 hr + 62° C.; 7 kPa; 4 hr |
| | Solid content (%) of colorant water dispersion | | 20.0 |
| | Volume-average particle size (nm) of colorant particles in colorant water dispersion | | 319 |

Preparation of Colorant-Containing Injection Liquid

Preparation Example 2-1

The resin solution 1 obtained in Preparation Example 1-1 was mixed with the colorant water dispersion at the compounding ratio shown below, and the resulting mixture was stirred, thereby preparing a colorant-containing injection liquid 1.

(Compounding Ratio (Parts(s) by Mass) of Components of Injection Liquid)

| | |
|---|---|
| Colorant water dispersion 1 (Yellow No. 5) | 7.2 |
| Colorant water dispersion 2 (Red No. 104-(1)) | 1.8 |
| Colorant water dispersion 3 (White) | 30.0 |
| Resin solution 1 (polyvinyl alcohol) | 61.0 |
| Total | 100.0 |

Production Examples 2-1 to 2-3 (Production of Concavo-Convex Plates 1 to 3)

[Copper-Plating Step]

A new roll to be processed for plate-making was subjected to ultrahigh precision cylindrical processing.

Preparation of Resin Solution

Preparation Example 1-1

A completely saponified polyvinyl alcohol "KURARAY POVAL" (product number: 29-99; saponification degree: not less than 99.3 mol %) available from Kuraray Co., Ltd., as the polymer compound A, was dissolved in water to prepare a 15%-conc. aqueous solution thereof, thereby obtaining a resin solution 1.

Next, the roll for plate-making was successively subjected to nickel plating and then to copper plating until reaching a plated copper thickness of 100 μm to form a copper-plated layer 1 thereon and thereby conduct correction of an eccentric amount of the roll. Then, the roll for plate-making was subjected to Ballard process in which the surface of the copper-plated layer 1 was polished, and silver was deposited thereon by displacement plating to form a silver-plated layer thereon. Then, copper was plated again on the silver-plated layer to form a copper-plated layer 2 thereon. The thickness of the copper-plated layer 2 formed on the roll for plate-making is shown as a thickness of the conductive layer in Table 3.

[Polishing Step]

Next, the diameter of the roll for plate-making on which the copper-plated layer 2 was formed, was measured at 5 positions in total of the roll, i.e., at both ends and three intermediate positions thereof. Then, the plated surface was removed by allowing a #1000 grind stone to slide over the roll from one end to the other end thereof by two reciprocating motions. Thereafter, on the basis of the aforementioned measurement, the grind stone was manually moved to polish a portion of the roll having a larger diameter more frequently, and on the other hand, polish a portion of the roll having a smaller diameter less frequently, whereby the roll was subjected to cylindrical polishing process such that the diameter of the roll as a whole was equalized from one end to the other end thereof. Successively, the #1000 grind stone was moved over the roll from one end to the other end thereof by one reciprocating motion, whereby the roll was subjected to semi-finishing cylindrical polishing process. Successively, the #2500 grind stone was moved over the roll from one end to the other end thereof by two reciprocating motions. At this time, while changing a feed speed of the grind stone, the roll was scanned to eliminate pitch marks, whereby the roll was subjected to fine-finishing cylindrical polishing process. Next, the #4000 grind stone was moved over the roll from one end to the other end thereof by five reciprocating motions. At this time, while changing a feed speed of the grind stone, the roll was scanned to eliminate pitch marks, whereby the roll was subjected to precision-finishing cylindrical polishing process. The roll was finally subjected to buffing to conduct mirror finish thereof. All of the aforementioned grind stones used above were silicon carbide-based grind stones.

[Etching Step]

Next, a photosensitive agent was applied onto the mirror-finished surface of the copper-plated layer 2 of the obtained roll for plate making by an ink-jet printing method, and then the photosensitive agent thus applied was exposed to light. Meanwhile, the roll will be subsequently subjected to wet-etching treatment to dissolve copper of the copper-plated layer 2 at its portion where the copper-plated layer 2 was exposed outside and thereby form concave portions (cells) thereon. However, in this case, an etching liquid is penetrated even into the portion of the copper-plated layer 2 which is covered with the photosensitive agent insolubilized by the exposure to light by coming around behind via the end of the portion covered by the insolubilized photosensitive agent, so that the etching of the concave portions is caused to undesirably proceed isotropically. Therefore, by preliminarily taking into account occurrence of the isotropic etching, the exposure of the photosensitive agent to laser light was conducted so as to form opening portions each having an opening area smaller than an opening area (cell size) of a desired concave portion.

Next, the roll for plate making thus subjected to the exposure to light was immersed in a developing liquid to dissolve the unexposed photosensitive agent present on the surface of the roll to thereby allow a part of the surface of the copper-plated layer 2 to expose outside. Then, the roll for plate making was further immersed in the etching liquid to wet-etch copper from the exposed portion of the surface of the copper-plated layer 2. The thus treated roll was then washed to remove the etching liquid therefrom. Finally, the roll for plate making was immersed in a stripping solution for the photosensitive agent to remove the photosensitive agent remaining on the roll for plate making therefrom.

The steps of the application of the photosensitive agent through the wet-etching were repeatedly conducted until the respective concave portions were formed into such a desired shape as shown in Table 3.

The thus obtained roll for plate making on which an uneven structure was formed was subjected to a Ballard process, followed by releasing the resulting uneven structure (the copper-plated layer 2) from the roll, thereby obtaining concavo-convex plates 1 to 3 having a quasi-flat plate shape.

The plan view shape of the respective concave portions of the thus obtained concavo-convex plates, the three-dimensional structure thereof the average lengths of opening portions and bottom portions thereof, and the average depth and average opening area thereof, as well as the average width of convex portions of the concavo-convex plates, are shown in Table 3.

Comparative Production Example 2-1 (Production of Concavo-Convex Plate C1)

The same procedure as in Production Example 2-1 was repeated except that no formation of the uneven structure by the etching step was conducted, thereby obtaining a quasi-flat plate-shaped plate C1 having no uneven structure.

TABLE 3

| | | | Production Examples | | | Comparative Production Example |
|---|---|---|---|---|---|---|
| | | | 2-1 | 2-2 | 2-3 | 2-1 |
| No. of concavo-convex plate | | | 1 | 2 | 3 | C1 |
| Material of conductive layer | | | Copper | Copper | Copper | Copper |
| Electrical resistivity (Ω · m) of material of conductive layer | | | $1.68 \times 10^{-8}$ | $1.68 \times 10^{-8}$ | $1.68 \times 10^{-8}$ | $1.68 \times 10^{-8}$ |
| Thickness (μm) of conductive layer*1 | | | 150 | 150 | 150 | 150 |
| Surface resistivity (Ω/□) (calculated value) | | | $1.1 \times 10^{-4}$ | $1.1 \times 10^{-4}$ | $1.1 \times 10^{-4}$ | $1.1 \times 10^{-4}$ |
| Uneven structure | Concave portions | Plan view shape of each concave portion | *a | *a | *a | None |
| | | Three-dimensional structure of each concave portion | *b | *b | *b | — |
| | | Average length (μm) of one side of opening portion | 210 | 530 | 110 | — |
| | | Average length (μm) of one side of bottom portion | 189 | 477 | 99 | — |
| | | Ratio [average length of opening portion/average length of bottom portion] | 1.1 | 1.1 | 1.1 | — |
| | | Average depth (μm) of concave portions | 40 | 100 | 20 | — |
| | | Average opening area ($mm^2$) of concave portions | 0.038 | 0.243 | 0.010 | — |

TABLE 3-continued

| | | Production Examples | | | Comparative Production Example |
|---|---|---|---|---|---|
| | | 2-1 | 2-2 | 2-3 | 2-1 |
| Convex portions | Average width (μm) of convex portions | 10 | 20 | 10 | — |
| | Average center distance (μm) of primary uneven structure | 220 | 550 | 120 | — |

Note
*[1]In the case where a material of the conductive layer is copper, the thickness of the conductive layer is calculated by subtracting an average depth of concave portions from an average height of convex portions.
*a: Rhombic shape;
*b: Inverted rhombic truncated pyramidal shape.

Production of Colorant Nonwoven Fabric

Examples 1 to 7 and Comparative Examples 1 and 2

[Glitter Pigment Applying Step]

The pearlescent pigment as the glitter pigment was applied by an electrostatic power spray-coating method.

The respective concavo-convex plates shown in Table 4 were grounded and disposed horizontally. Next, using an electrostatic powder spray-coating apparatus "GX-8500αβ" and an electrostatic powder spray-coating gun "GX132" (nozzle type: slit nozzle) both available from Parker Engineering Co., Ltd., the below-mentioned pearlescent pigment was sprayed onto an uneven structure-bearing surface of the concavo-convex plate from directly above.

Incidentally, the electrostatic powder spray-coating was conducted under such conditions that a gun voltage was 100 kV, a gun current value was 35 μA, an amount of the pearl agent injected was 50%, an amount of air for transporting the pearlescent pigment was 50 L/min, and a distance between a gun injection port and the uneven structure-bearing surface of the concavo-convex plate was 300 mm.

The pearlescent pigment was applied to the concavo-convex plate while varying a scanning speed of the nozzle over the concavo-convex plate such that 1 to 3 pieces of the pearlescent pigment were put therein per one concave portion of the concavo-convex plate.

In the case where the pearlescent pigment was applied to the metallic concavo-convex plate, since the concavo-convex plate was grounded, almost a whole amount of the pearlescent pigment was brought into the concave portions in association with the scanning of the nozzle, and the residual pearlescent pigment remaining on the convex portions of the concavo-convex plate could also be applied into the concave portions by shaking the concavo-convex plate several times.

[Step 1-1]

The concavo-convex plate to which the pearlescent pigment was applied in the aforementioned step was used as a collector. The colorant-containing injection liquid 1 was filled in a syringe of a resin solution-type electrospinning apparatus "Nanofiber Electrospinning Unit" available from Kato Tech Co., Ltd., and injected onto the uneven structure-bearing surface of the collector under the following electrospinning conditions to deposit nanofibers on a region of 3 cm in width and 5 cm in length on the surface of the collector.

In this case, the deposition of the nanofibers on the collector was temporarily stopped, and the nanofibers were subjected to a pressure filling treatment in which a surface-buffed stainless steel roller having a diameter of 3 cm was rolled over the nanofiber-deposited side surface of the collector while applying a constant load thereto to thereby filling the nanofibers under pressure into the collector, followed by starting the deposition of the nanofibers on the collector again. Such a pressure filling treatment was repeated three more times, i.e., four times in total.

Next, the nanofibers deposited were subjected to heat treatment at 180° C. for 20 minutes, so that the completely saponified polyvinyl alcohol in the nanofibers was crystallized and subjected to water-insolubilizing treatment, thereby obtaining a colored nonwoven fabric laminated on the collector. The thickness of the resulting colored nonwoven fabric was 30 μm, the thickness of the respective nanofibers therein was from 100 to 800 nm, and the content of the colorant on the basis of the nanofibers was 85% in total.

Incidentally, in Comparative Example 1, a plain PET film "LUMIRROR" (product number: #50-S10) available from Toray Industries Inc., was used as the collector.

Figure 6:
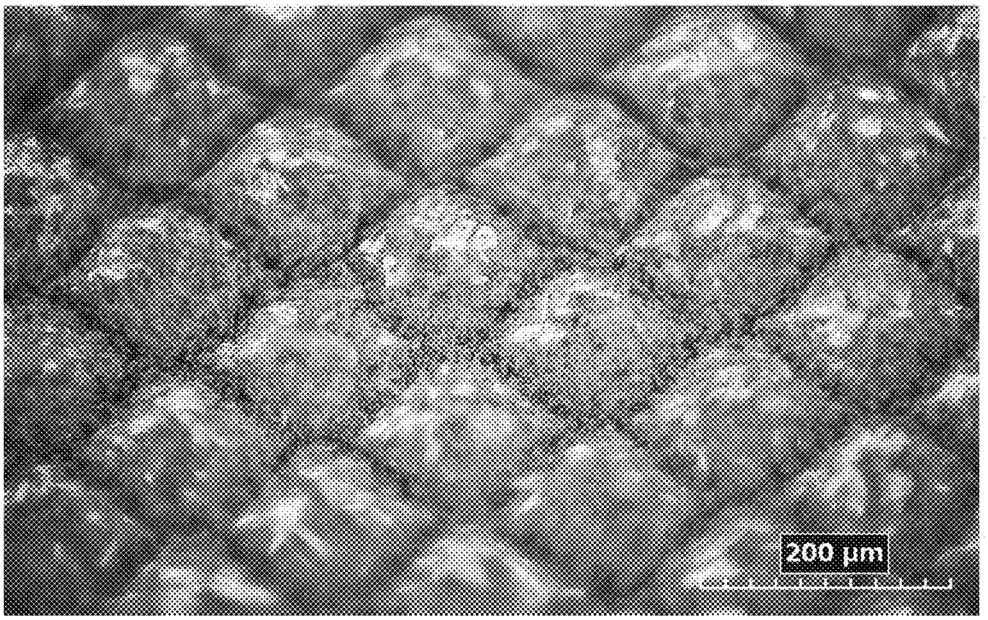
FIG. 6 is an enlarged photograph (magnification: ×500 times) of the colored nonwoven fabric obtained in Example 7.
Figure 7:
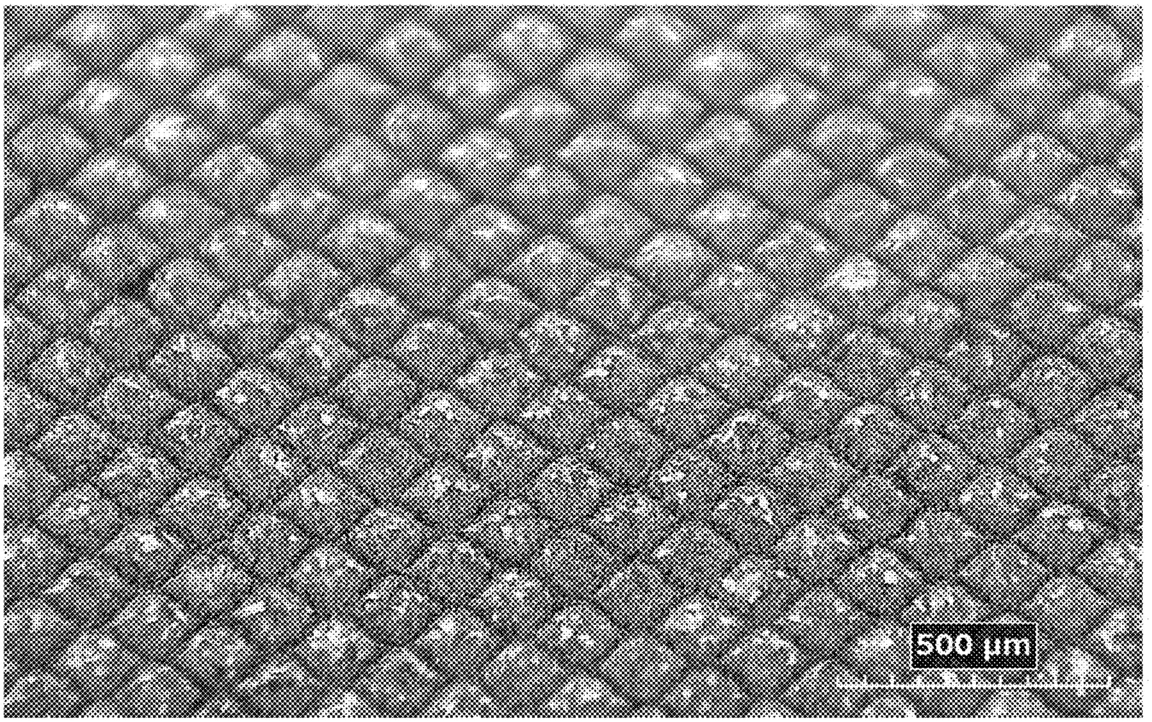
FIG. 7 is an enlarged photograph (magnification: ×200 times) of the colored nonwoven fabric obtained in Example 7.

An enlarged photos of the colored nonwoven fabric obtained in Example 7 are shown in FIGS. 6 and 7. Incidentally, one division of a scale bar shown in a right lower portion of the enlarged photo of FIG. 6 indicates 20 μm, and one division of a scale bar shown in a right lower portion of the enlarged photo of FIG. 7 indicates 50 μm.

The thus obtained colored nonwoven fabrics were subjected to the following evaluations 1 to 3. The results are shown in Table 4.

(Electrospinning Conditions)

Voltage applied: 20 kV

Distance between tip end of capillary and collector: 100 mm

Average amount of injection liquid injected: 1 mL/min

Injection environmental conditions; temperature: 25° C.; humidity: 40% RH (Pearlescent Pigment)

MBE025: Pearl agent "METASHINE MBE025RY" (titanium oxide-coated; average primary particle size: 25 μm; average thickness: 0.5 μm) available from Nippon Sheet Glass Co., Ltd.

MT1040: Pearl agent "METASHINE MT1040RYS1" (titanium oxide-coated, silica-treated; average primary particle size: 40 μm; average thickness: 1.3 μm) available from Nippon Sheet Glass Co., Ltd.

MT1080: Pearl agent "METASHINE MT1080RYS1" (titanium oxide-coated, silica-treated; average primary particle size: 80 μm; average thickness: 1.3 μm) available from Nippon Sheet Glass Co., Ltd.

[Evaluation 1: Rub Fastness]

An artificial leather "SUPULARE PBZ13001" available from IDEATEX Japan Co., Ltd., was attached onto a bottom surface (1 inch×1 inch) of a 50 g weight through a double-sided adhesive tape.

The colored nonwoven fabric obtained in the aforementioned respective Examples and Comparative Examples was peeled off from the collector, and the portion of the print pattern formed on the surface of the colored nonwoven fabric which had been opposed to the collector was reciprocatively rubbed with the SUPULARE-attached surface of the weight 10 times. After the rubbing, the rubbed surface of the sample was visually observed to ascertain whether or not any deformation, breakage or the like was present therein, as well as an appearance thereof, thereby evaluating rub fastness of the colored nonwoven fabric. In the following evaluation ratings, when the rating is 3 or 2, the colored nonwoven fabric were practically usable.

(Evaluation Ratings)

3: Neither breakage nor deformation occurred, and no change in gloss in appearance was present.

2: Although none of breakage and deformation occurred, a change in gloss in appearance was present.

1: Breakage and deformation were observed.

[Evaluation 2: Gloss Feel and Transparent Feel]

The colored nonwoven fabric obtained in the aforementioned respective Examples and Comparative Examples was peeled off from the collector, and the portion of the print pattern formed on the surface of the colored nonwoven fabric which had been opposed to the collector was measured for a glossiness thereof under a light-irradiation condition of 60° using a gloss meter "IG-330" available from HORIBA Ltd., to evaluate a gloss feel and a transparent feel of the colored nonwoven fabric.

(Evaluation Ratings)

Glossiness of less than 40: Having a gloss of makeup skin with elegant glossy feel, and creating a luxury finish.

Glossiness of not less than 40 and less than 60: Having a higher gloss feel as makeup skin, looking like applying a thick makeup with deteriorated bare skin feel, and in particular, when attaching the colored nonwoven fabric, causing a large difference in appearance between the skin portion treated with the colored nonwoven fabric and the untreated skin portion.

Glossiness of not less than 60: Having a strong luster feel over a whole portion as makeup skin, imparting glistering unnatural impression, looking like applying a thick makeup with a low character, also creating flat finish with featureless skin feel, and when forming wrinkles on the colored nonwoven fabric in association with deformation of the face, seeming to emphasize the deformation.

[Evaluation 3: Resilient Feel of Skin and Skin Age]

A 30 years old female (one person) was selected as a subject. A whole part of the face of the subject was washed with a facial cleaner generally available on the market, and then the water droplets remained attached onto the face were removed by wiping off the droplets with a towel. Thereafter, the left cheek and its surrounding portions of the subject were wet with a milky lotion containing the following formulation components.

Next, the colored nonwoven fabric obtained in the aforementioned respective Examples and Comparative Examples in the state before being peeled off from the collector was attached onto the left cheek of the subject. Then, the collector was peeled off and removed from the colored nonwoven fabric, so that the colored nonwoven fabric remained attached to the let cheek.

Then, the left cheek of the subject onto which the colored nonwoven fabric was attached was presented to 10 expert panelists for cosmetics, and observed by these expert panelists to comparatively evaluate a resilient feel of the skin and skin age based on skin feeling according to the following evaluation ratings in comparison with the right cheek.

The total value of the evaluation points given to the colored nonwoven fabric by the 10 expert panelists was regarded as a score for the evaluation.

(Evaluation Ratings)

3 Points: The left cheek had a good resilient feel of skin in comparison with the right cheek, and the skin age looked apparently younger than the real age.

2 Points: The left cheek had a good resilient feel of skin in comparison with the right cheek, and the skin age looked younger than the real age.

1 Point: No large difference in resilient feel of skin and skin age between the left cheek and the right cheek was recognized.

0 Point: The left cheek had an extraneous feel different from that of the skin in comparison with the right cheek.

(Formulation Components (% by mass) of Milky Lotion)

| | |
|---|---|
| Oxyethylene/methyl polysiloxane copolymer*1 | 2.0 |
| Methyl polysiloxane 10CS*2 | 3.0 |
| Methyl polysiloxane 100CS*3 | 15.0 |
| Cetanol*4 | 1.5 |
| Squalane*5 | 5.0 |
| Dibutyl hydroxy toluene*6 | 0.02 |
| Propyl p-hydroxybenzoate*7 | 0.1 |
| Glycerin | 3.0 |
| 1,2-Propanediol | 3.0 |
| Ion-exchanged water | balance |
| Total | 100.0 |

Incidentally, the respective asterisked notations described above are as follows.
*1"KF6015" available from Shin-Etsu Chemical Co., Ltd.
*2"KF-96A-10CS" available from Shin-Etsu Chemical Co., Ltd.
*3"KF-96A-100CS" available from Shin-Etsu Chemical Co., Ltd.
*4, *5, *6 and *7Products available from FUJIFILM Wako Pure Chemical Corporation.

TABLE 4

| | | | Examples | | | | |
|---|---|---|---|---|---|---|---|
| | | | 1 | 2 | 3 | 4 | 5 |
| Kind of concavo-convex plate used in electrospinning | | | 1 | 1 | 1 | 2 | 2 |
| Glitter pigment | Pearlescent pigment | Kind | MBE025 | MT1040 | MT1080 | MBE025 | MT1040 |
| | | Average primary particle size (μm) | 25 | 40 | 80 | 25 | 40 |
| | | Average thickness (μm) | 0.5 | 1.3 | 1.3 | 0.5 | 1.3 |
| | | Shape | Flat plate shape | Flat plate shape | Flat plate shape | Flat plate shape | Flat plate shape |
| Preparation of injection liquid | No. of injection liquid | | 1 | 1 | 1 | 1 | 1 |
| | Formulation of injection liquid (part(s) by mass) | Colorant water dispersion 1 (yellow No. 5) | 7.2 | 7.2 | 7.2 | 7.2 | 7.2 |
| | | Colorant water dispersion 4 (Red No. 104-(1)) | 1.8 | 1.8 | 1.8 | 1.8 | 1.8 |

TABLE 4-continued

| | | | | | | | |
|---|---|---|---|---|---|---|---|
| | | Colorant water dispersion 6 (white) | 30.0 | 30.0 | 30.0 | 30.0 | 30.0 |
| | | Resin solution 1 (polyvinyl alcohol) | 61.0 | 61.0 | 61.0 | 61.0 | 61.0 |
| | Content (%) in injection liquid | Colorant yellow | 1.4 | 1.4 | 1.4 | 1.4 | 1.4 |
| | | Colorant red | 0.4 | 0.4 | 0.4 | 0.4 | 0.4 |
| | | Colorant white | 6.0 | 6.0 | 6.0 | 6.0 | 6.0 |
| | | Polymer compound A | 9.2 | 9.2 | 9.2 | 9.2 | 9.2 |
| | Content (%) of colorant based on content of polymer compound A in injection liquid | | 85.2 | 85.2 | 85.2 | 85.2 | 85.2 |
| Colored nonwoven fabric | Uneven shape | Plan view shape of convex portion | Rhombic shape | Rhombic shape | Rhombic shape | Rhombic shape | Rhombic shape |
| | | Average length (μm) of plan view shapes of convex portions | 210 | 210 | 210 | 530 | 530 |
| | | Average height (μm) of convex portions | 40 | 40 | 40 | 100 | 100 |
| | | Average maximum cross-sectional area ($mm^2$) of convex portions | 0.038 | 0.038 | 0.038 | 0.243 | 0.243 |
| | $L^*_1$ value of convex portions | | 67 | 65 | 63 | 65 | 63 |
| | $L^*_2$ value of concave portions | | 46 | 46 | 46 | 44 | 44 |
| Evaluation | Rub fastness | | 3 | 3 | 3 | 3 | 3 |
| | Glossiness | | 33 | 35 | 38 | 30 | 32 |
| | Resilient feel of skin and skin age | | 28 | 25 | 23 | 22 | 20 |

| | | | Examples | | Comparative Examples | |
|---|---|---|---|---|---|---|
| | | | 6 | 7 | 1 | 2 |
| Kind of concavo-convex plate used in electrospinning | | | 2 | 3 | LUMIRROR | C1 |
| Glitter pigment | Pearlescent pigment | Kind | MT1080 | MBE025 | MBE025 | MBE025 |
| | | Average primary particle size (μm) | 80 | 25 | 25 | 25 |
| | | Average thickness (μm) | 1.3 | 0.5 | 0.5 | 0.5 |
| | | Shape | Flat plate shape | Flat plate shape | Flat plate shape | Flat plate shape |
| Preparation of injection liquid | No. of injection liquid | | 1 | 1 | 1 | 1 |
| | Formulation of injection liquid (part(s) by mass) | Colorant water dispersion 1 (yellow No. 5) | 7.2 | 7.2 | 7.2 | 7.2 |
| | | Colorant water dispersion 4 (Red No. 104-(1)) | 1.8 | 1.8 | 1.8 | 1.8 |
| | | Colorant water dispersion 6 (white) | 30.0 | 30.0 | 30.0 | 30.0 |
| | | Resin solution 1 (polyvinyl alcohol) | 61.0 | 61.0 | 61.0 | 61.0 |
| | Content (%) in injection liquid | Colorant yellow | 1.4 | 1.4 | 1.4 | 1.4 |
| | | Colorant red | 0.4 | 0.4 | 0.4 | 0.4 |
| | | Colorant white | 6.0 | 6.0 | 6.0 | 6.0 |
| | | Polymer compound A | 9.2 | 9.2 | 9.2 | 9.2 |
| | Content (%) of colorant based on content of polymer compound A in injection liquid | | 85.2 | 85.2 | 85.2 | 85.2 |
| Colored nonwoven fabric | Uneven shape | Plan view shape of convex portion | Rhombic shape | Rhombic shape | None | None |
| | | Average length (μm) of plan view shapes of convex portions | 530 | 110 | — | — |
| | | Average height (μm) of convex portions | 100 | 20 | — | — |
| | | Average maximum cross-sectional area ($mm^2$) of convex portions | 0.243 | 0.010 | — | — |
| | $L^*_1$ value of convex portions | | 61 | 68 | — | — |
| | $L^*_2$ value of concave portions | | 44 | 48 | — | — |
| Evaluation | Rub fastness | | 3 | 3 | 1 | 1 |
| | Glossiness | | 34 | 36 | 61 | 63 |
| | Resilient feel of skin and skin age | | 17 | 29 | 2 | 4 |

From Table 4, it was confirmed that the colored nonwoven fabrics obtained in Examples 1 to 7 were excellent in rub fastness, exhibited a gloss of makeup skin with an elegant glossy feel, a luxury finish, and a gloss feel and a transparent feel close to those of a human skin, and further were capable of improving a resilient feel of skin for well controlling a skin age, as compared to the colored nonwoven fabrics obtained in Comparative Examples 1 and 2.

In addition, as shown in the enlarged photographs of FIGS. 6 and 7, it was confirmed that the resulting colored nonwoven fabric had a rhombic grid-like uneven shape on the surface thereof.

Also, from FIG. 6, it was confirmed that the uneven shape of the colored nonwoven fabric had portions respectively swelled into a rounded shape toward a center of each convex portion so as to form the convex portions corresponding to skin hills and the concave portions corresponding to skin grooves.

Furthermore, from FIG. 7, it was confirmed that the pearlescent pigment was applied only to the convex portions corresponding to skin hills, and substantially no pearlescent pigment was applied to the concave portions corresponding to skin grooves.

Examples 8 to 14

[Step 1-1]

The same procedure as in Example 1 was repeated except for using the combination of the two kinds of concavo-convex plates shown in Table 5 as the collector, thereby obtaining a colored nonwoven fabric (1-1) and a colored nonwoven fabric (1-2) each laminated on the surface of the collector. The thicknesses of the resulting colored nonwoven fabrics were respectively 30 μm, the thickness of the respective nanofibers therein was from 100 to 800 nm, and the content of the colorants on the basis of the nanofibers in the respective colored nonwoven fabric was 85% in total. The thus obtained colored nonwoven fabric (1-1) and colored nonwoven fabric (1-2) were subjected to the following evaluation 4. The results are shown in Table 5.

[Evaluation 4: Three-Dimensional Feel (1)]

A 30 years old female (one person) was selected as a subject. A whole part of the face of the subject was washed with a facial cleaner generally available on the market, and then the cleaner droplets remained attached onto the face were removed by wiping off the droplets with a towel. Thereafter, the skin of the whole part of the face was wet with the aforementioned milky lotion.

Next, the colored nonwoven fabric (1-1) and the colored nonwoven fabric (1-2) obtained in each of Examples 8 to 14 in the state before being peeled off from the collector were attached onto the forehead and jaw of the subject, respectively. Then, the collector was peeled off and removed from the respective colored nonwoven fabrics, so that the colored nonwoven fabric (1-1) and the colored nonwoven fabric (1-2) remained attached to the forehead and jaw of the subject, respectively.

Then, the whole part of the face of the subject after attaching the colored nonwoven fabrics thereto was observed by 10 expert panelists for cosmetics at the position spaced away by 1 m therefrom to comparatively evaluate an impression of the whole part of the face according to the following evaluation ratings. The total value of the evaluation points given by the 10 expert panelists was regarded as a score for the evaluation.

(Evaluation Ratings)

3 Points: The forehead portion of the face seemed to be in the distance, whereas the lip portion of the face seemed to be close, thereby imparting a passionate impression.

2 Points: No change in impression of the face was recognized.

1 Point: The forehead portion of the face seemed to be close, whereas the lip portion of the face seemed to be in the distance, thereby imparting a rational impression.

TABLE 5-1

| | | | Examples | | | | | | |
|---|---|---|---|---|---|---|---|---|---|
| | | | 8 | 9 | 10 | 11 | 12 | 13 | 14 |
| Colored nonwoven fabric (1-1) used for forehead portion | Kind of concavo-convex plate used in electrospinning | | 1 | 2 | 3 | 2 | 1 | 3 | 1 |
| | Uneven shape (1) | Plan view shape of convex portion | Rhombic shape | Rhombic shape | Rhombic shape | Rhombic shape | Rhombic shape | Rhombic shape | Rhombic shape |
| | | Average length (μm) of plan view shapes of convex portions | 210 | 530 | 110 | 250 | 120 | 50 | 120 |
| | | Average height (μm) of convex portions | 40 | 100 | 20 | 100 | 50 | 20 | 50 |
| | | Average maximum cross-sectional area (1) ($mm^2$) of convex portions | 0.038 | 0.243 | 0.010 | 0.243 | 0.038 | 0.010 | 0.038 |
| | $L^*_1$ value of convex portions | | 65 | 61 | 68 | 61 | 65 | 68 | 65 |
| | $L^*_2$ value of concave portions | | 46 | 44 | 48 | 44 | 46 | 48 | 46 |
| | Glitter pigment | Kind of pearlescent pigment | MT1040 | MT1080 | MBE025 | MT1080 | MT1040 | MBE025 | MT1040 |
| | | Average primary particle size (μm) | 40 | 80 | 25 | 80 | 40 | 25 | 40 |
| | | Average thickness | 1.3 | 1.3 | 0.5 | 1.3 | 1.3 | 0.5 | 1.3 |
| | | Shape | Flat plate shape | Flat plate shape | Flat plate shape | Flat plate shape | Flat plate shape | Flat plate shape | Flat plate shape |

TABLE 5-2

| | | | Examples | | | | | | |
|---|---|---|---|---|---|---|---|---|---|
| | | | 8 | 9 | 10 | 11 | 12 | 13 | 14 |
| Colored nonwoven fabric (1-2) used for jaw portion | Kind of concavo-convex plate used in electrospinning | | 1 | 3 | 2 | 1 | 3 | 1 | 2 |
| | Uneven shape (2) | Plan view shape of convex portion | Rhombic shape | Rhombic shape | Rhombic shape | Rhombic shape | Rhombic shape | Rhombic shape | Rhombic shape |
| | | Average length (μm) of plan view shapes of convex portions | 210 | 110 | 530 | 210 | 110 | 210 | 530 |
| | | Average height (μm) of convex portions | 40 | 20 | 100 | 40 | 20 | 40 | 100 |
| | | Average maximum cross-sectional area (2) ($mm^2$) of convex portions | 0.038 | 0.010 | 0.243 | 0.038 | 0.010 | 0.038 | 0.243 |
| | $L^*_1$ value of convex portions | | 65 | 68 | 61 | 65 | 68 | 65 | 61 |
| | $L^*_2$ value of concave portions | | 46 | 48 | 44 | 46 | 48 | 46 | 44 |
| | Glitter pigment | Kind of pearlescent pigment | MT1040 | MBE025 | MT1080 | MT1040 | MBE025 | MT1040 | MT1080 |
| | | Average primary particle size (μm) | 40 | 25 | 80 | 40 | 25 | 40 | 80 |
| | | Average thickness | 1.3 | 0.5 | 1.3 | 1.3 | 0.5 | 1.3 | 1.3 |
| | | Shape | Flat plate shape | Flat plate shape | Flat plate shape | Flat plate shape | Flat plate shape | Flat plate shape | Flat plate shape |
| Ratio between average heights of convex portions [average height in forehead portion/average height in jaw portion] | | | 1.0 | 5.0 | 0.2 | 2.5 | 2.5 | 0.5 | 0.5 |

TABLE 5-2-continued

| | | Examples | | | | | | |
|---|---|---|---|---|---|---|---|---|
| | | 8 | 9 | 10 | 11 | 12 | 13 | 14 |
| Ratio between average maximum cross-sectional areas of convex portions [average maximum cross-sectional area in forehead portion/average maximum cross-sectional area in jaw portion] | | 1.0 | 23.2 | 0.04 | 6.4 | 3.6 | 0.3 | 0.2 |
| Evaluation | Three-dimensional feel (1) | 20 | 10 | 30 | 13 | 14 | 26 | 27 |

From the results of Examples 8 to 14 shown in Table 5, it was confirmed that when the colored nonwoven fabrics having respective uneven shapes that were different in average height or average maximum cross-sectional area of convex portions thereof from each other were used for each part of the face, it was possible to impart a three-dimensional feel thereto, so that an impression of the face given to another person could be changed.

Examples 15 to 21

[Step 1-1]

The same procedure as in Example 1 was repeated except for using the combination of the two kinds of concavo-convex plates shown in Table 6 as the collector, thereby obtaining a colored nonwoven fabric (2-1) and a colored nonwoven fabric (2-2) each laminated on the surface of the collector. The thicknesses of the resulting colored nonwoven fabrics were respectively 30 μm, the thickness of the respective nanofibers therein was from 100 to 800 nm, and the content of the colorants on the basis of the nanofibers in the respective colored nonwoven fabrics was 85% in total. The thus obtained colored nonwoven fabric (2-1) and colored nonwoven fabric (2-2) were subjected to the following evaluation 5. The results are shown in Table 6.

[Evaluation 5: Three-Dimensional Feel (2)]

A 30 years old female (one person) was selected as a subject. A whole part of the face of the subject was washed with a facial cleaner generally available on the market, and then the water droplets remained attached onto the face were removed by wiping off the droplets with a towel. Thereafter, the skin of the whole part of the face was wet with the aforementioned milky lotion.

Next, the colored nonwoven fabric (2-1) and the colored nonwoven fabric (2-2) obtained in each of Examples 15 to 21 in the state before being peeled off from the collector were attached onto the nose and both cheeks of the subject, respectively. Then, the collector was peeled off and removed from the respective colored nonwoven fabrics, so that the colored nonwoven fabric (2-1) and the colored nonwoven fabric (2-2) remained attached to the nose and both cheeks of the subject, respectively.

Then, the whole part of the face of the subject after attaching the colored nonwoven fabrics thereto was observed by 10 expert panelists for cosmetics at the position spaced away by 1 m therefrom to comparatively evaluate an impression of the whole part of the face according to the following evaluation ratings. The total value of the evaluation points given by the 10 expert panelists was regarded as a score for the evaluation.

(Evaluation Ratings)

3 Points: The face looked more chiseled and deep, and an impression of the face was considerably changed.

2 Points: No change in impression of the face was recognized.

1 Point: The face looked flat, and an impression of the face was considerably changed.

TABLE 6-1

| | | | Examples | | | | | | |
|---|---|---|---|---|---|---|---|---|---|
| | | | 15 | 16 | 17 | 18 | 19 | 20 | 21 |
| Colored nonwoven fabric (2-1) used for nose portion | Kind of concavo-convex plate used in electrospinning | | 1 | 2 | 3 | 2 | 1 | 3 | 1 |
| | Uneven shape (1) | Plan view shape of convex portion | Rhombic shape | Rhombic shape | Rhombic shape | Rhombic shape | Rhombic shape | Rhombic shape | Rhombic shape |
| | | Average length (μm) of plan view shapes of convex portions | 210 | 530 | 110 | 250 | 120 | 50 | 120 |
| | | Average height (μm) of convex portions | 40 | 100 | 20 | 100 | 50 | 20 | 50 |
| | | Average maximum cross-sectional area ($mm^2$) of convex portions | 0.038 | 0.243 | 0.010 | 0.243 | 0.038 | 0.010 | 0.038 |
| | $L^*_1$ value of convex portions | | 65 | 61 | 68 | 61 | 65 | 68 | 65 |
| | $L^*_2$ value of concave portions | | 46 | 44 | 48 | 44 | 46 | 48 | 46 |
| | Glitter pigment | Kind of pearlescent pigment | MT1040 | MT1080 | MBE025 | MT1080 | MT1040 | MBE025 | MT1040 |
| | | Average primary particle size (μm) | 40 | 80 | 25 | 80 | 40 | 25 | 40 |
| | | Average thickness | 1.3 | 1.3 | 0.5 | 1.3 | 1.3 | 0.5 | 1.3 |
| | | Shape | Flat plate shape | Flat plate shape | Flat plate shape | Flat plate shape | Flat plate shape | Flat plate shape | Flat plate shape |

TABLE 6-2

| | | | Examples | | | | | | |
|---|---|---|---|---|---|---|---|---|---|
| | | | 15 | 16 | 17 | 18 | 19 | 20 | 21 |
| Colored nonwoven fabric (2-2) used for cheek portion | Kind of concavo-convex plate used in electrospinning | | 1 | 3 | 2 | 1 | 3 | 1 | 2 |
| | Uneven shape (2) | Plan view shape of convex portion | Rhombic shape | Rhombic shape | Rhombic shape | Rhombic shape | Rhombic shape | Rhombic shape | Rhombic shape |
| | | Average length (μm) of plan view shapes of convex portions | 210 | 110 | 530 | 210 | 110 | 210 | 530 |
| | | Average height (μm) of convex portions | 40 | 20 | 100 | 40 | 20 | 40 | 100 |
| | | Average maximum cross-sectional area (mm$^2$) of convex portions | 0.038 | 0.010 | 0.243 | 0.038 | 0.010 | 0.038 | 0.243 |
| | $L*_1$ value of convex portions | | 65 | 68 | 61 | 65 | 68 | 65 | 61 |
| | $L*_2$ value of concave portions | | 46 | 48 | 44 | 46 | 48 | 46 | 44 |
| | Glitter pigment | Kind of pearlescent pigment | MT1040 | MBE025 | MT1080 | MT1040 | MBE025 | MT1040 | MT1080 |
| | | Average primary particle size (μm) | 40 | 25 | 80 | 40 | 25 | 40 | 80 |
| | | Average thickness | 1.3 | 0.5 | 1.3 | 1.3 | 0.5 | 1.3 | 1.3 |
| | | Shape | Flat plate shape | Flat plate shape | Flat plate shape | Flat plate shape | Flat plate shape | Flat plate shape | Flat plate shape |
| Ratio between average heights of convex portions [average height in nose portion/average height in cheek portion] | | | 1.0 | 5.0 | 0.2 | 2.5 | 2.5 | 0.5 | 0.5 |
| Ratio between average maximum cross-sectional areas of convex portions [average maximum cross-sectional area in nose portion/average maximum cross-sectional area in cheek portion] | | | 1.0 | 23.2 | 0.04 | 6.4 | 3.6 | 0.3 | 0.2 |
| Evaluation results | Three-dimensional feel (2) | | 20 | 28 | 12 | 24 | 26 | 16 | 14 |

From the results of Examples 15 to 21 shown in Table 6, it was confirmed that when the colored nonwoven fabrics having respective uneven shapes that were different in average height or average maximum cross-sectional area of convex portions thereof from each other were used for each part of the face, it was possible to impart a three-dimensional feel thereto.

Examples 22 to 25

[Step 1-1]

The same procedure as in Example 1 was repeated except for using the combination of the two kinds of concavo-convex plates shown in Table 7 as the collector, thereby obtaining a colored nonwoven fabric (3-1) and a colored nonwoven fabric (3-2) each laminated on the surface of the collector. The thicknesses of the resulting colored nonwoven fabrics were respectively 30 μm, the thickness of the respective nanofibers therein was from 100 to 800 nm, and the content of the colorants on the basis of the nanofibers in the respective colored nonwoven fabrics was 85% in total.

[Step 3]

Ink-jet printing was conducted on the surface of the respective colored nonwoven fabrics obtained in the step 1-1 on which the uneven shape was formed, using the below-mentioned water-based ink 1 for ink-jet printing.

The water-based ink 1 for ink-jet printing as shown in Table 7 which was prepared by the following method was filled into a handy printer cartridge "HC-01K" available from Ricoh Company, Ltd., whose interior was previously fully rinsed with ion-exchanged water and dried, and then using the "Ricoh Handy Printer" (tradename) available from Ricoh Company, Ltd., ink-jet printing (resolution: 600 dpi× 600 dpi; amount of ink droplets ejected: 10 pL) was conducted on the respective colored nonwoven fabrics obtained in the step 1-1.

The print image on the respective colored nonwoven fabrics was printed such that the ink 1 applied was arranged along the convex portions of the concavo-convex plate so as to comply with the uneven structure of the concavo-convex plate, and the convex portions of the colored nonwoven fabrics after peeling off and removing the concavo-convex plate therefrom were rimmed by the ink 1.

The line width for the printing was determined as follow. The region extending from an end of the nose to the ear on each cheek of the face was divided into four angular stages along a circular profile of the face assuming that the head portion of a human was regarded as being of a cylindrical shape, in which no printing was conducted in the 1st stage region extending from the nose (starting point: 0°) to a front side portion of the cheek (30° from the starting point); the line width of the region extending from the front side portion of the cheek (30° from the starting point) to a central portion of the cheek (45° from the starting point) was set to 1 dot (line width: about 34 μm); the line width of the region extending from the central portion of the cheek (45° from the starting point) to a rear side portion of the cheek (60° from the starting point) was set to 2 dote (line width: about 68 μm); and the line width of the region extending from the rear side portion of the cheek (60° from the starting point) to the ear (end point; 90° from the starting point) was set to 3 dots (line width: about 100 μm).

Immediately after the printing, while measuring the temperature of the printed surface using a radiation thermometer "IT-540S" available from HORIBA Ltd., so as not to raise the temperature of the printed surface to 50° C. or higher, the resulting print image was dried for 5 minutes by a hot air dryer while repeating On and OFF of blowing of hot air therefrom, thereby obtaining a colored nonwoven fabric (3'-1) and a colored nonwoven fabric (3'-2) each laminated on the surface of the collector. Using the thus obtained colored nonwoven fabric (3'-1) and colored nonwoven fabric (3'-2), the following evaluation 6 was conducted. The results are shown in Table 7.

(Preparation of Water-Based Ink 1 for Ink-Jet Printing)

The colorant water dispersion, polyethylene glycol 400 (hereinafter also referred to merely as "PEG400"), 1,2-hexanediol, 1,2-propanediol, a modified glycerin "Liponic EG-1" (ethyleneoxide 26 mol adduct of glycerin) available from Vantage Speciality Ingredients Inc., (hereinafter also referred to merely as "Liponic EG-1") and ion-exchanged water as shown in Table 7 were added and mixed with each other, and the resulting mixed solution was subjected to filtration treatment through a 0.45 μm-mesh membrane filter "Minisart" available from Sartorius Inc., thereby obtaining a water-based ink 1. The static surface tension of the thus obtained water-based ink 1 as measured at 20° C. was 36 mN/m.

[Evaluation 6: Three-Dimensional Feel (3)]

A 30 years old female (one person) was selected as a subject. A whole part of the face of the subject was washed with a facial cleaner generally available on the market, and then the cleaner droplets remained attached onto the face were removed by wiping off the droplets with a towel. Thereafter, the skin of the whole part of the face was wet with the aforementioned milky lotion.

Next, the colored nonwoven fabric (3'-1) and the colored nonwoven fabric (3'-2) obtained in each of Examples 22 to 25 in the state before being peeled off from the collector were attached onto the forehead and the jaw of the subject, respectively.

Then, the collector was peeled off and removed from the respective colored nonwoven fabrics, so that the colored nonwoven fabric (3'-1) and the colored nonwoven fabric (3'-2) remained attached to the forehead and the jaw of the subject, respectively.

Then, the whole part of the face of the subject after attaching the colored nonwoven fabrics thereto was observed by 10 expert panelists for cosmetics at the position spaced away by 1 m therefrom to comparatively evaluate an impression of the whole part of the face according to the following evaluation ratings. The total value of the evaluation points given by the 10 expert panelists was regarded as a score for the evaluation.

(Evaluation Ratings)

3 Points: The depth feel of the face was emphasized, and an impression of the face was considerably changed.

2 Points: No change in impression of the face was recognized.

1 Point: The face looked flat, and an impression of the face was considerably changed for the worse.

TABLE 7-1

| | | | Examples | | | |
|---|---|---|---|---|---|---|
| | | | 22 | 23 | 24 | 25 |
| Colored nonwoven fabric (3-1) used for nose portion | Kind of concavo-convex plate used in electrospinning | | 1 | 2 | 2 | 1 |
| | Uneven shape (1) | Plan view shape of convex portion | Rhombic shape | Rhombic shape | Rhombic shape | Rhombic shape |
| | | Average length (μm) of plan view shapes of convex portions | 210 | 530 | 530 | 210 |
| | | Average height (μm) of convex portions | 40 | 100 | 100 | 40 |
| | | Average maximum cross-sectional area ($mm^2$) of convex portions | 0.038 | 0.243 | 0.243 | 0.038 |
| | $L^*_1$ value of convex portions | | 65 | 61 | 61 | 65 |
| | $L^*_2$ value of concave portions | | 46 | 44 | 44 | 46 |
| | Glitter pigment | Kind of pearlescent pigment | MT1040 | MT1080 | MT1080 | MT1040 |
| | | Average primary particle size (μm) | 40 | 80 | 80 | 40 |
| | | Average thickness | 1.3 | 1.3 | 1.3 | 1.3 |
| | | Shape | Flat plate shape | Flat plate shape | Flat plate shape | Flat plate shape |
| Colored nonwoven fabric (3-2) used for cheek portion | Kind of concavo-convex plate used in electrospinning | | 1 | 3 | 1 | 3 |
| | Uneven shape (2) | Plan view shape of convex portion | Rhombic shape | Rhombic shape | Rhombic shape | Rhombic shape |
| | | Average length (μm) of plan view shapes of convex portions | 210 | 110 | 210 | 110 |
| | | Average height (μm) of convex portions | 40 | 20 | 40 | 20 |
| | | Average maximum cross-sectional area ($mm^2$) of convex portions | 0.038 | 0.010 | 0.038 | 0.010 |
| | $L^*_1$ value of convex portions | | 65 | 68 | 65 | 68 |
| | $L^*_2$ value of concave portions | | 46 | 48 | 46 | 48 |
| | Glitter pigment | Kind of pearlescent pigment | MT1040 | MBE025 | MT1040 | MBE025 |
| | | Average primary particle size (μm) | 40 | 25 | 40 | 25 |
| | | Average thickness | 1.3 | 0.5 | 1.3 | 0.5 |
| | | Shape | Flat plate shape | Flat plate shape | Flat plate shape | Flat plate shape |

TABLE 7-2

| | | | Examples | | | |
|---|---|---|---|---|---|---|
| | | | 22 | 23 | 24 | 25 |
| Preparation of injection liquid | No. of injection liquid | | 1 | 1 | 1 | 1 |
| | Formulation of injection liquid (part(s) by mass) | Colorant water dispersion 1 (Yellow No. 5) | 7.2 | 7.2 | 7.2 | 7.2 |
| | | Colorant water dispersion 4 (Red No. 104-(1)) | 1.8 | 1.8 | 1.8 | 1.8 |
| | | Colorant water dispersion 6 (White) | 30.0 | 30.0 | 30.0 | 30.0 |
| | | Resin solution 1 (polyvinyl alcohol) | 61.0 | 61.0 | 61.0 | 61.0 |
| | Content (%) in injection liquid | Colorant yellow | 1.4 | 1.4 | 1.4 | 1.4 |
| | | Colorant red | 0.4 | 0.4 | 0.4 | 0.4 |
| | | Colorant white | 6.0 | 6.0 | 6.0 | 6.0 |
| | | Polymer compound A | 9.2 | 9.2 | 9.2 | 9.2 |
| | Content (%) of colorant based on content of polymer compound A in injection liquid | | 85 | 85 | 85 | 85 |

TABLE 7-2-continued

| | | | Examples | | | |
|---|---|---|---|---|---|---|
| | | | 22 | 23 | 24 | 25 |
| Preparation of water-based ink | Formulation of water-based ink (part(s) by mass) | No. of ink | 1 | 1 | 1 | 1 |
| | | Colorant water dispersion 2 (Yellow) | 5.4 | 5.4 | 5.4 | 5.4 |
| | | Colorant water dispersion 3 (Blue) | 3.2 | 3.2 | 3.2 | 3.2 |
| | | Colorant water dispersion 5 (Red) | 4.2 | 4.2 | 4.2 | 4.2 |
| | | PEG400 | 4 | 4 | 4 | 4 |
| | | 1,2-Hexanediol | 3.8 | 3.8 | 3.8 | 3.8 |
| | | 1,2-Propanediol | 7.2 | 7.2 | 7.2 | 7.2 |
| | | Liponic EG-1 | 4 | 4 | 4 | 4 |
| | | Ion-exchanged water*[1] | Balance | Balance | Balance | Balance |
| Evaluation results | | Three-dimensional feel (3) | 23 | 30 | 26 | 28 |

Note
*[1]Balance in 100 parts by mass in total of water-based ink

From the results of Examples 22 to 25 shown in Table 7, it was confirmed that by obtaining the colored nonwoven fabrics having respective uneven shapes that were different in average height or average maximum cross-sectional area of convex portions thereof from each other and then further applying the ink to these colored nonwoven fabrics by an ink-jet printing method to print them such that convex portions thereof were rimmed by ink, and further by using the resulting colored nonwoven fabrics for each part of the face, it was possible to emphasize a three-dimensional feel of the face.

INDUSTRIAL APPLICABILITY

The colored nonwoven fabric of the present invention is excellent in rub fastness, can exhibit a gloss feel and a transparent feel close to those of a human skin, and further is excellent in a sense of unity with the skin in appearance when attached thereto and can improve a resilient feel of the skin and a skin age, and furthermore can impart a three-dimensional feel, such as a depth feel, chiseled features, etc., to the face. Therefore, the colored nonwoven fabric can be used as a skin patch sheet which is used by attaching to the skin. More concretely, the colored nonwoven fabric can be used in the applications, such as a skin protective sheet, an UV protective sheet, etc. Moreover, the colored nonwoven fabric can be used as a makeup seal by further applying precise makeup on the colored nonwoven fabric attached to a skin.

REFERENCE SIGNS LIST

10: Colored nonwoven fabric
11: Convex portions
12: Concave portions
20, 30: Concavo-convex plate
40: Resin solution-type electrospinning apparatus
50: Resin melt-type electrospinning apparatus
41, 51: Syringe
42, 52: High voltage supply
43, 53: Collector
54: Heater
41*a*, 51*a*: Cylinder
41*b*, 51*b*: Plunger
41*c*, 51*c*: Capillary
42*a*, 52*a*: Positive electrode
42*b*, 52*b*: Negative electrode

The invention claimed is:

1. A colored nonwoven fabric, comprising a colorant and nanofibers, wherein:

the colored nonwoven fabric comprises an uneven shape on at least a part of a surface thereof, the uneven shape has an uneven shape imitating a surface configuration of skin, and an $L^*_1$ value of convex portions of the uneven shape is higher than an $L^*_2$ value of concave portions of the uneven shape, wherein a difference between the $L^*_1$ value of the convex portions and the $L^*_2$ value of the concave portions is not less than 5 and not more than 60, and wherein an average height of the convex portions of the uneven shape is not less than 10 μm and not more than 250 μm, and an average maximum cross-sectional area of the convex portions is not less than 0.01 $mm^2$ and not more than 0.25 $mm^2$.

2. The colored nonwoven fabric according to claim 1, wherein the colored nonwoven fabric comprises a glitter pigment in the convex portions of the uneven shape thereof.

3. The colored nonwoven fabric according to claim 1, wherein the colored nonwoven fabric comprises two or more uneven shapes that are different in the average height or average maximum cross-sectional area of the convex portions from each other.

4. The colored nonwoven fabric according to claim 3, wherein the two or more uneven shapes are configured for use on a forehead portion and a jaw portion of a face, respectively.

5. The colored nonwoven fabric according to claim 3, wherein the two or more uneven shapes are configured for use on a nose portion and a face side portion of a face, respectively.

6. The colored nonwoven fabric according to claim 1, wherein the nanofibers comprise at least a water-insoluble polymer compound.

7. The colored nonwoven fabric according to claim 6, wherein the water-insoluble polymer compound is at least one compound selected from the group consisting of completely saponified polyvinyl alcohol that can be rendered water-insoluble by water-insolubilizing treatment, a partially saponified polyvinyl alcohol that can be rendered water-insoluble by water-insolubilizing treatment by cross-linking, an alkali-soluble cellulose, an oxazoline-modified silicone, zein, and a water-soluble polyester resin.

8. The colored nonwoven fabric according claim 1, wherein the colorant is in the form of colorant-containing polymer particles.

9. The colored nonwoven fabric according to claim 1, wherein a content of the colorant based on the nanofibers in the colored nonwoven fabric as calculated in terms of a ratio thereof assuming that a content of the nanofibers in the colored nonwoven fabric is 100% by mass, is not less than 50% by mass and not more than 110% by mass.

10. A colored nonwoven fabric set comprising two or more colored nonwoven fabrics according claim 1, wherein:

the two or more colored nonwoven fabrics comprise respective uneven shapes that are different in the average height or average maximum cross-sectional area of the convex portions from each other.

11. The colored nonwoven fabric set according to claim 10, wherein the colored nonwoven fabrics comprise respective uneven shapes that are different in the average height or average maximum cross-sectional area of the convex portions from each other, and are used for a forehead portion and a jaw portion, respectively.

12. The colored nonwoven fabric set according to claim 10, wherein the colored nonwoven fabrics comprise respective uneven shapes that are different in the average height or average maximum cross-sectional area of the convex portions from each other, and are used for a nose portion and a face side portion, respectively.

13. The colored nonwoven fabric according to claim 1, wherein the uneven shape is an uneven shape capable of reproducing the 5th relief of the skin or an uneven shape capable of reproducing the 2nd relief of the skin.

14. The colored nonwoven fabric according to claim 1, wherein the average height of the convex portions of the uneven shape is not less than 0.5 μm and not more than 7 μm, and an average maximum cross-sectional area of the convex portions is not less than 40 $\mu m^2$ and not more than 3,600 $\mu m^2$.

15. A process for producing a colored nonwoven fabric that comprises a colorant and nanofibers in which a surface of the colored nonwoven fabric is at least partially formed into an uneven shape, the process comprising:

injecting a polymer compound A by an electrospinning method to deposit the nanofibers on a surface of a collector; and adjusting an L* value by coloring the nanofibers such that an $L^*_1$ value of convex portions of the resulting colored nonwoven fabric is higher than an $L^*_2$ value of concave portions thereof.

16. The process for producing a colored nonwoven fabric according to claim 15, wherein the L* value adjusting step comprises applying a glitter pigment such that the $L^*_1$ value of the convex portions of the resulting colored nonwoven fabric is higher than the $L^*_2$ value of the concave portions thereof.

17. The process for producing a colored nonwoven fabric according to claim 16, wherein in the L* value adjusting step, coloring is conducted by an ink-jet printing method or by an electrostatic powder spray-coating method.

18. The process for producing a colored nonwoven fabric according to claim 15, wherein the collector has an uneven structure on at least a part of a surface thereof.

* * * * *